United States Patent [19]

Jones et al.

[11] Patent Number: 5,446,158

[45] Date of Patent: Aug. 29, 1995

[54] PROCESS FOR SYNTHESIS OF FK-506 AND TRICARBONYL INTERMEDIATES

[75] Inventors: Todd K. Jones, Edison; Sander G. Mills, Woodbridge; David Askin, Edison; Robert A. Reamer, Bloomfield; Richard Desmond, Metuchen; David M. Tschaen, Aberdeen; Ralph P. Volante, East Windsor; Ichiro Shinkai, Westfield, all of N.J.

[73] Assignee: Merck & Co., Inc., Rahway, N.J.

[21] Appl. No.: 596,847

[22] Filed: Oct. 12, 1990

Related U.S. Application Data

[63] Continuation of Ser. No. 375,091, Jun. 30, 1989, abandoned, and a continuation-in-part of Ser. No. 295,877, Jan. 11, 1989, abandoned.

[51] Int. Cl.⁶ ............................................... C07F 7/18
[52] U.S. Cl. .................................... 546/14; 546/245; 548/110; 548/229; 556/12; 564/463; 564/305; 560/45; 560/174; 560/51; 549/4; 540/456; 540/452
[58] Field of Search ............... 540/456, 452; 546/14, 546/245; 548/110, 229; 556/12; 564/463, 305; 560/45, 174, 51; 549/4

[56] References Cited

PUBLICATIONS

Jones et al. "J. Am. Chem. Soc." vol. 112, pp. 2998–3017 (1990).

*Primary Examiner*—Robert T. Bond
*Attorney, Agent, or Firm*—Mollie M. Yang; David L. Rose

[57] ABSTRACT

A process is described for the total synthesis of the macrolide immunosuppressant, FK-506, and important tricarbonyl process intermediates thereof. The tricarbonyl intermediates can be produced by the mild oxidation of 2,3-dihydroxy carboxylate compounds containing olefin moieties.

10 Claims, No Drawings

PROCESS FOR SYNTHESIS OF FK-506 AND TRICARBONYL INTERMEDIATES

CROSS REFERENCE TO RELATED APPLICATIONS

This is a continuation-in-part application of Ser. No. 07/295,877 (Case Docket No. 17853) filed Jan. 11, 1989, and hereby incorporated by reference. This is also a continuation of Ser. No. 07/375,091, filed 30 Jun. 1989. Both related applications are now abandoned.

BACKGROUND OF THE INVENTION

1) Field of the Invention

This invention relates to a total synthetic process for producing the macrolide immunosuppressant FK-506 and important tricarbonyl process intermediates thereof.

2) Brief Disclosures in the Art

The novel 23-membered tricyclo-macrolide FK-506 isolated and characterized by Tanaka, Kuroda, and co-workers, see JACS, 109, pp. 5031, 1987, and EPO Publication No. 0,184,162, has been shown to possess exceptional immunosuppressive activity. The potential usefulness of such an agent in bone marrow and organ transplantations coupled with its unique structural features has prompted many in the field to initiate an effort towards the total synthesis of FK-506 (1).

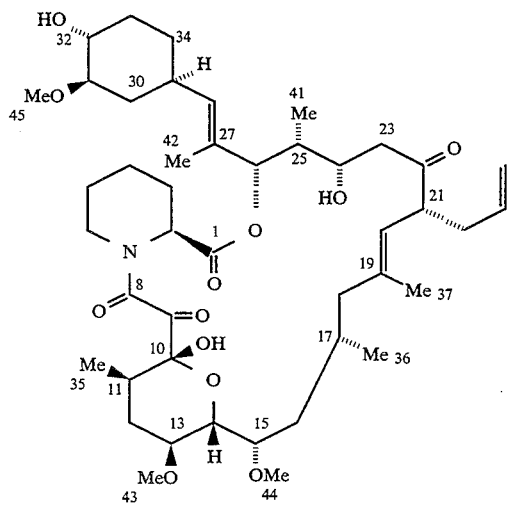

A formidable problem in the general and specific solution to the synthesis of FK-506, is the formation of the tricarbonyl lactol moiety of FK-506, (the $C_8$-$C_9$-$C_{10}$ tricarbonyl moiety in lactol form) particularly in the presence of olefin moieties. For example, there are no examples for the preparation of 2,3-diketo carboxylates, carboxamides, carboxamides, or their corresponding lactol derivatives by the oxidation of 2,3-dihydroxy carboxylates and concomitant lactolization in a macrolide molecule also possessing an olefin moiety (for a review on the preparation of the tricarbonyl functionality see M. B. Rubin, Chemical Reviews, 75, 177, 1975, and references therein).

Prior preparations of the 2,3-diketocarboxyl functionality have involved either oxidation of beta-keto esters (H. H. Wasserman, W. T. Han, Tetrahedron Letters, 25, 3743, 1984; or Williams, D. R., Benbow, J. W., J. Org. Chem., 1988, 53, 4643) or the acylation of oxalate anion equivalents, e.g. 1,2-diethoxy-1,2-bis-(trimethylsilyloxy) ethylene with an appropriate electrophile such as an acid chloride or an active ester derivative thereof (see M. T. Reetz, S. H. Kyung, Tetrahedron Letters, 26, 6333, 1985).

These procedures would be inapplicable for the FK-506 system due to the harshness of the reaction conditions in each approach. The oxidation of beta-ketoesters to 2,3-diketoesters would not be compatible with the olefinic linkages present in FK-506 systems because they would also be susceptible to oxidation. Similarly, the strong Lewis acid conditions necessary for the addition of oxalate equivalents to acid chlorides as used in the Reetz approach would not be applicable in the presence of the many sensitive hydroxyl or protected hydroxyl functional groups of FK-506.

What is needed in the art is an overall general synthesis for FK-506 utilizing readily available starting materials which would allow the synthesis of the tricarbonyl moiety of FK-506 in the presence of olefin functionality.

SUMMARY OF THE INVENTION

We have found a process for the selective high-yield synthesis of 2,3-diketoesters, amides, or imides, (as shown below in Scheme i) Ia-c (as exists in the macrocyclic tricarbonyl lactol FK-506 (1), starting from the corresponding aldehydes II. The aldehydes II are first converted to the homologous 2,3-dihydroxyamides or esters IV by addition of an appropriately protected 2-hydroxy acetic acid derived ester enolate equivalent III. Compounds III can be prepared by a sequential series of reactions consisting of imide hydrolysis, carbonyl activation, and amide or ester formation. The resulting 2-alkoxy-3-hydroxy-amide or ester IV is then deprotected to give the desired 2,3-dihydroxy compound V. Oxidation of the hydroxyl functionalities with dimethylsulfoxide and oxalyl chloride at $-78°$ yields the desired 2,3-diketoester or amide I.

We have also found a mild and highly selective method for the subsequent conversion of I to the corresponding 6-membered ring lactol array by treatment with trifluoroacetic acid or hydrofluoric acid at room temperature. The process allows for clean, high yield conversions thereby eliminating complicated mixtures of by-products which severely reduces the yield and purity of the desired 6-membered ring lactol derived tricarbonyl product.

A particular embodiment of this lactolization procedure is the selective conversion of the FK-506 fragment, 2,3-diketo-7-hydroxyl (or protected hydroxyl) heptanoates VI or longer chain alkanoates to the corresponding 2-hydroxy-2-(2'-oxo-2'-acetyl)-tetrahydropyrans VII, by treatment with trifluoroacetic acid in THF at room temperature.

In accordance with this invention there is provided a process for synthesizing 2,3-dicarboxylate compounds of structure I, comprising the steps of:

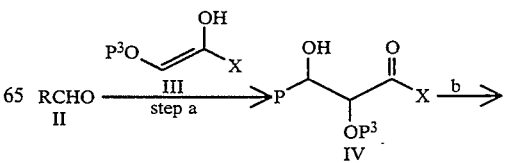

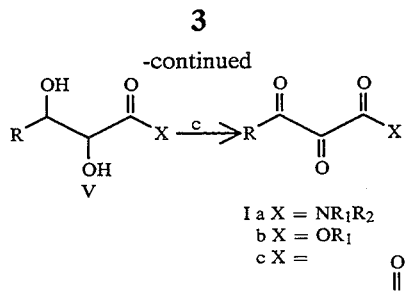

Ia X = NR₁R₂
b X = OR₁
c X =

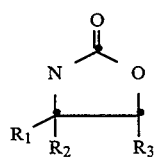

(a) contacting aldehyde II with hydroxyl protected acetate enolate equivalent III under an inert atmosphere in the temperature range of −100° C. to 20° C. in an anhydrous, inert, non-hydroxylic organic solvent for a sufficient time to produce the addition product IV;

(b) deprotecting the 2-hydroxyl function of product IV from step (a) to form V;

(c) treating the hydroxyl-deprotected product V from step (b) in an inert, anhydrous, non-hydroxylic solvent in the presence of both oxalyl chloride and dimethyl sulfoxide under an inert atmosphere at −78° C. to 0° C., followed by triethylamine, for a sufficient time to effect formation of the 2,3-dicarboxylate compound I; wherein: R is substituted or unsubstituted linear or branched $C_1$-$C_{40}$ alkyl, wherein the substituents can be OH, $C_1$-$C_4$ alkoxy, $C_6$-$C_8$ phenoxy, SH, $C_1$-$C_4$ alkylthio, $C_6$-$C_8$ arylthio, $NH_2$, $N(C_1$-$C_4$ alkyl$)_2$, the $C_{11}$-$C_{34}$ carbon framework of FK-506; $P^3$ is linear or branched $C_1$-$C_{10}$ alkyl, $C_6$-$C_{10}$ aryl or benzyl, which can be substituted by halo or $C_1$-$C_4$ alkoxy; trihydrocarbosilyl, wherein said hydrocarbosilyl groups are independently chosen from $C_1$-$C_4$ linear or branched alkyl, phenyl or benzyl; X is $NR_1R_2$, $OR_1$, $SR_1$, pipecolinic acid or ester, where $R_1/R_2/R_3$ are independently chosen from: H, $C_1$-$C_4$ linear or branched alkyl, benzyl, phenyl, which may be substituted with halo or $C_1$-$C_4$ alkoxy; and wherein cation M is Li, Na, K, Cs, Ca, Al, Zn, Ti, Sn or B(alkyl)$_2$, wherein the alkyl is $C_1$-$C_4$ linear or branched.

Further provided is a lactolization process comprising the step of treating VI

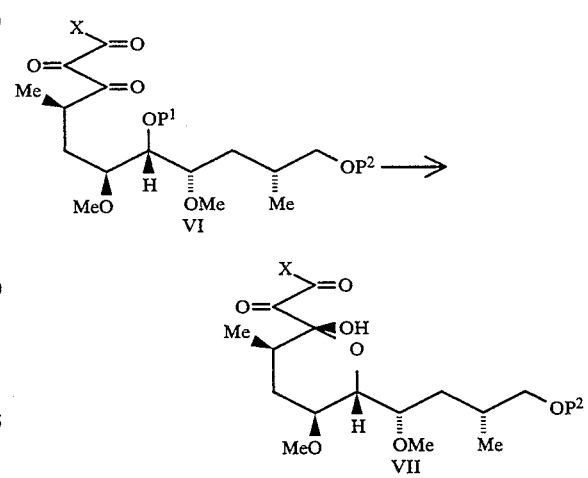

with aqueous hydrofluoric acid or aqueous trifluoroacetic acid in an inert organic solvent at −10° to 50° C. for a sufficient time to produce the lactol VII, wherein X is selected from the above indicated substituents.

$P^1$ and $P^2$ are selected from conventional trihydrocarbosilyl protecting groups, wherein $P^1$ can be selectively removed in the presence of $P^2$ by appropriate choice of deprotection reaction conditions as is standard in the art (e.g. choice of reaction temperature, reaction solvent, reagent concentration, reaction time, or strength of reagent in cases of acid catalyzed hydrolysis.

Furthermore there are provided the following compounds of the formulae which dan be converted by methods described herein into intermediates for the synthesis of the immunosuppressant FK-506 (1):

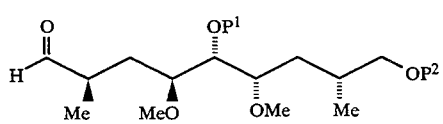

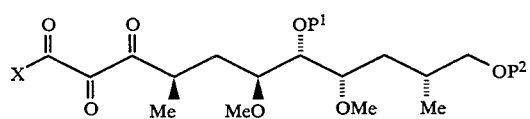

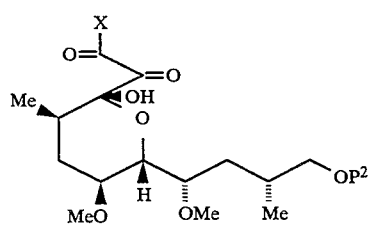

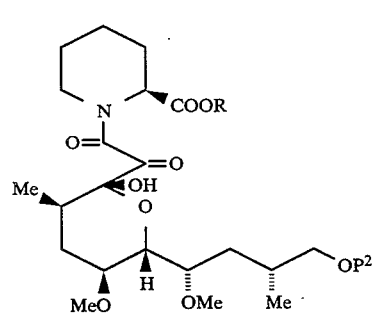

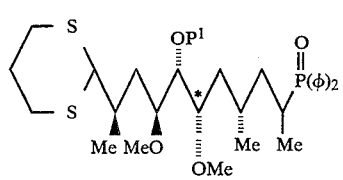
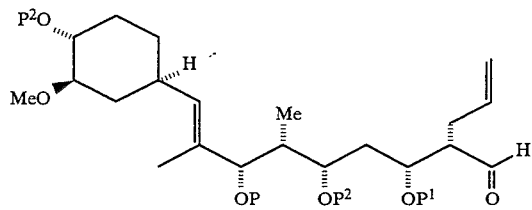

-continued

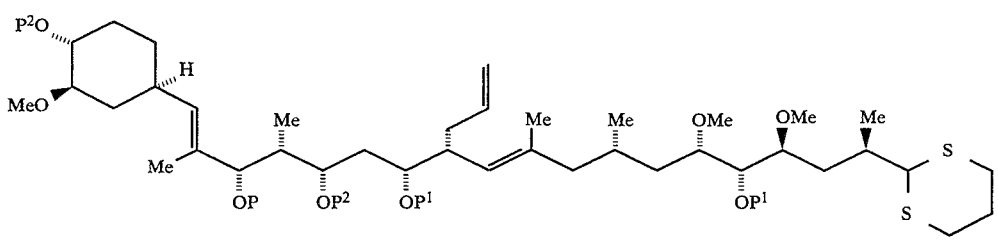

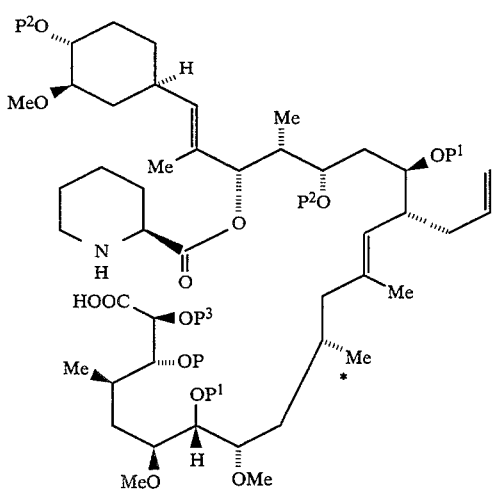
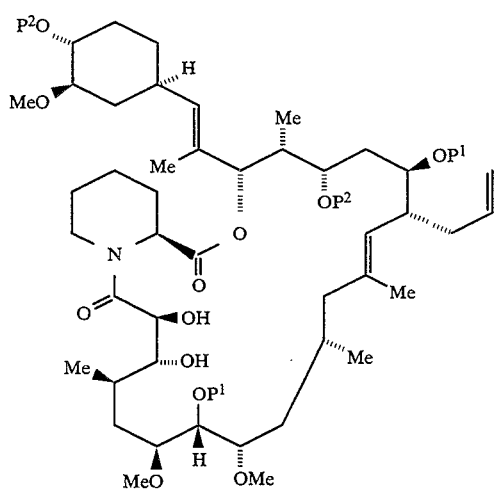
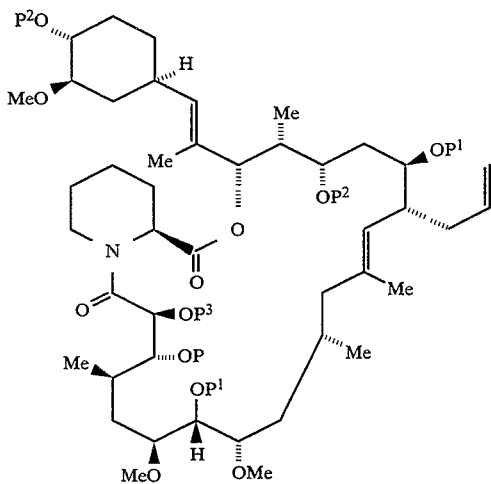
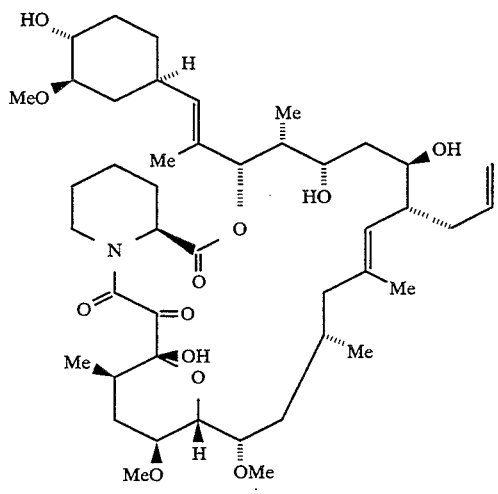

wherein each X and P is independently as defined above with the stipulation that P, $P^1$, and $P^2$ can be removed in the following order: P can be selectively removed in the presence of $P^1$ and $P^2$; $P^1$ can be selectively removed in the presence of $P^2$. Furthermore, $P^3$ is defined such that it can be selectively removed in the presence of P, $P^1$, and $P^2$ by variation of reagent and/or hydrolyzing conditions. $P^3$ is preferably not trihydrocarbosilyl; P, $P^1$ $P^2$ are preferably trihydrocarbosilyl.

In addition there is provided a process comprising the step of contacting LII, wherein $P^1/P^2$ are independently defined as H or tri(hydrocarbo)silyl, wherein said hydrocarbo groups are independently chosen from $C_1$–$C_4$ linear or branched alkyl, phenyl or benzyl, such that $P^1$ can be selectively removed in the presence of $P^2$, and R is selected from allyl, propyl, ethyl or methyl, and $R_1$ is methyl or ethyl,

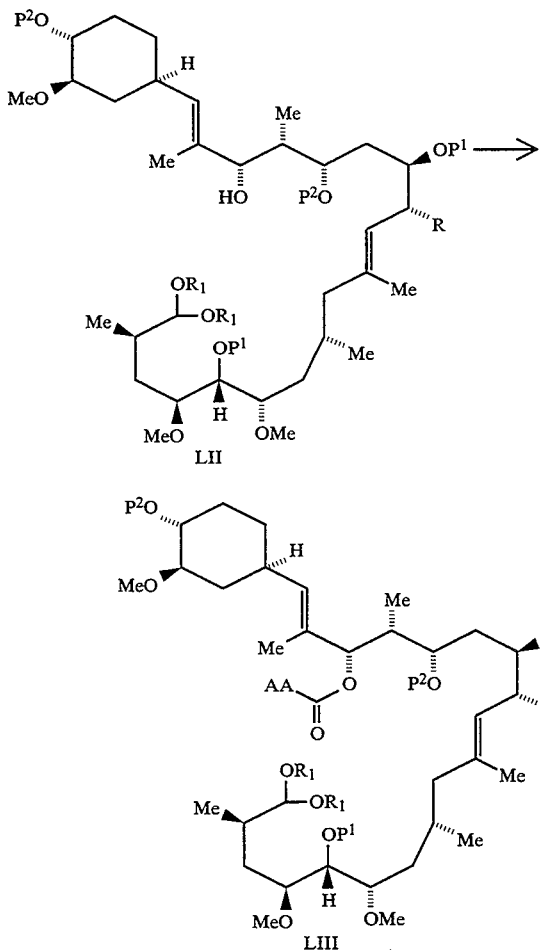

LII

LIII with an N-protected secondary amino acid AA-COOH of the structure:

Acyclic Secondary Amino Acids:

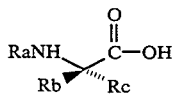

where $R_a = C_1$-$C_{10}$ alkyl, aryl, or substituted alkyl; $R_b = H$, $C_1$-$C_{10}$ alkyl, aryl, or substituted alkyl; and $R_c = H$, $C_1$-$C_{10}$ alkyl, aryl, or substituted alkyl, said substituents, including halo, $C_1$-$C_4$ alkoxy, said acyclic amino acids also including N-methyl, N-ethyl, N-benzyl, N-phenyl substituted L- and D-forms (and racemates) of alanine, valine, leucine, isoleucine, phenylalanine, tyrosine, diiodotyrosine, thyroxine, serine, threonine, methionine, cysteine, cystine, aspartic acid, glutamic acid, lysine, arginine, known synthetic variants thereof, and sarcosine;

Cyclic Secondary Amino Acids of the formula:

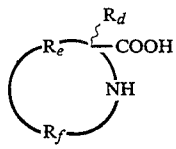

where $R_d = H$, $C_1$-$C_{10}$ alkyl, aryl or branched alkyl, which may be in the alpha or beta configuration; $R_e$ and $R_f$ are carbon-containing chains joined with NH to form a 4–10 membered carbon-nitrogen ring, which can be saturated, unsaturated or partially unsaturated, and can contain one or more O, S or N heteroatoms and which can be ring substituted, said cyclic amino acids also including L-, D- and racemic forms of proline, hydroxyproline, N-methyltryptophan, N-methylhistidine, 2-pipecolinic acid, known synthetic variants thereof, wherein said substituents include halo and $C_1$-$C_4$ alkoxy; said contacting occurring in an inert, anhydrous solvent, under a nitrogen atmosphere, at $-40°$ to $-60°$ C., in the presence of dicyclohexylcarbodiimide and a tertiary amine proton acceptor for a sufficient time to form LIII.

Also there is provided a compound of the formula:

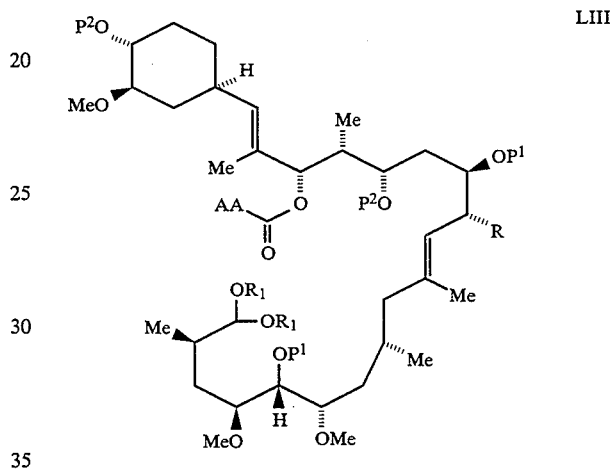

LIII wherein $P^2$, $P^1$, R, $R_1$, and AA are as defined hereinabove.

There is also furthermore provided a process comprising the steps of:

(a) contacting LII, wherein $P^1/P^2$ are independently defined as H or tri(hydrocarbo)silyl, wherein said hydrocarbo groups are independently chosen from $C_1$-$C_4$ linear or branched alkyl, phenyl or benzyl, such that $P^1$ can be selectively removed in the presence of $P^2$, and R is selected from allyl, propyl, ethyl or methyl, and $R_1$ is methyl or ethyl, with an N-protected secondary amino acid AA-COOH of the structure:

Acyclic Secondary Amino Acids:

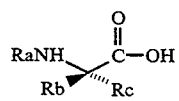

where $R_a = C_1$-$C_{10}$ alkyl, aryl, or substituted alkyl; $R_b = H$, $C_1$-$C_{10}$ alkyl, aryl, or substituted alkyl; and $R_c = H$, $C_1$-$C_{10}$ alkyl, aryl, or substituted alkyl, said substituents, including halo, $C_1$-$C_4$ alkoxy, said acyclic amino acids also including N-methyl, N-ethyl, N-benzyl, N-phenyl substituted L- and D-forms (and racemates) of alanine, valine, leucine, isoleucine, phenylalanine, tyrosine, diiodotyrosine, thyroxine, serine, threonine, methionine, cysteine, cystine, aspartic acid, glutamic acid, lysine, arginine, known synthetic variants thereof, and sarcosine;

Cyclic Secondary Amino Acids of the formula:

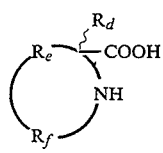

where $R_d$=H, $C_1$-$C_{10}$ alkyl, aryl or branched alkyl, which may be in the alpha or beta configuration; $R_e$ and $R_f$ are carbon-containing chains joined with NH to form a 4–10 membered carbon-nitrogen ring, which can be saturated, unsaturated or partially unsaturated, and can contain one or more O, S or N heteroatoms and which can be ring substituted, said cyclic amino acids also including L-, D- and racemic forms of proline, hydroxyproline, N-methyltryptophan, N-methylhistidine, 2-pipecolinic acid, known synthetic variants thereof, wherein said substituents include halo and $C_1$-$C_4$ alkoxy; said contacting occurring in an inert, anhydrous solvent, under a nitrogen atmosphere, at −40° to 60° C., in the presence of dicyclohexylcarbodiimide and a tertiary amine proton acceptor for a sufficient time to form LIII;

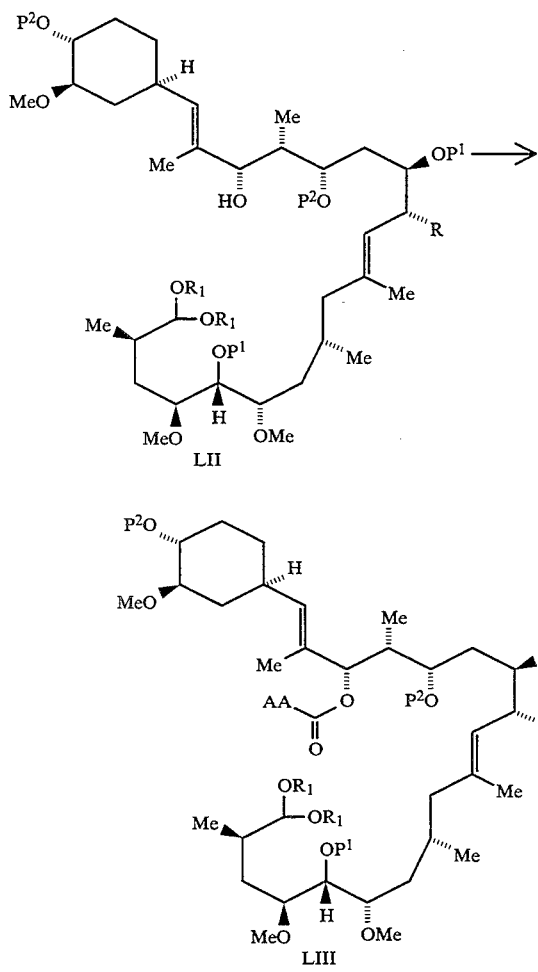

(b) contacting structure LIII in an anhydrous inert organic solvent, under an inert atmosphere, at 10°–40° C., with glyoxylic acid and acetic acid for a sufficient time to form aldehyde LIV;

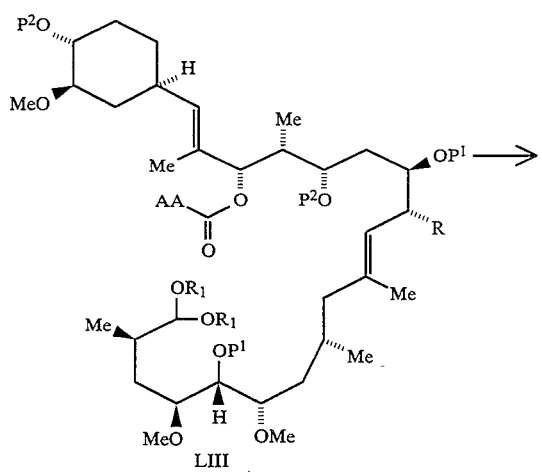

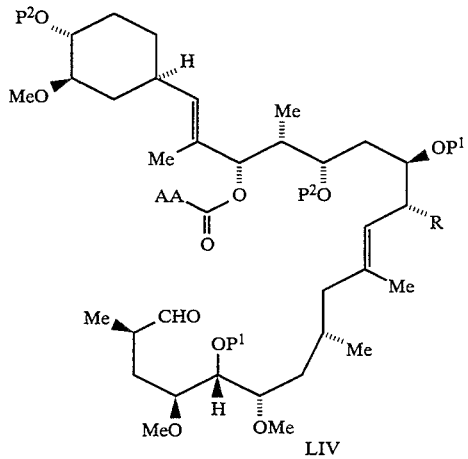

(c) contacting aldehyde LIV with substituted acetimide XV, an organic amine proton acceptor and dialkylboron salt in an anhydrous inert solvent at −40° to −60° C., in an inert atmosphere, for a sufficient time to form the imide LV;

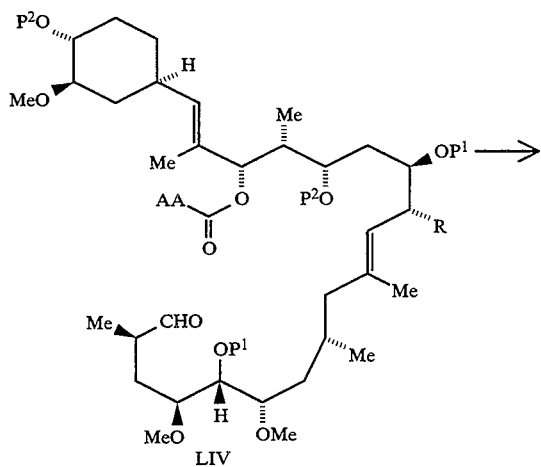
LIV
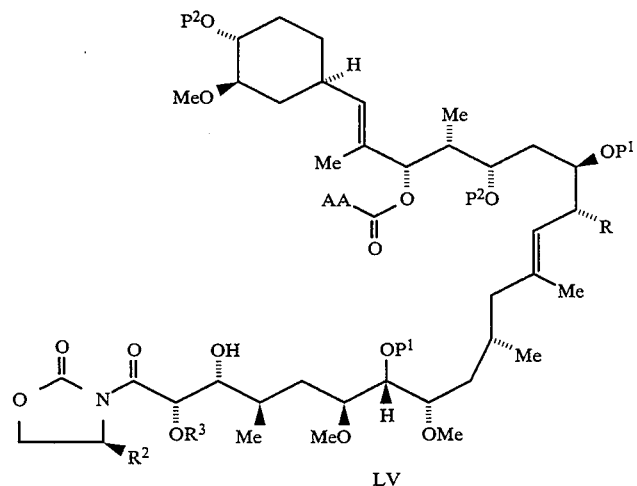
LV
(d) contacting imide LV with aqueous hydrogen peroxide in aqueous organic water miscible solvent containing alkali metal hydroxide at 0°–5° C. for a sufficient time to form the carboxylic acid LVI;
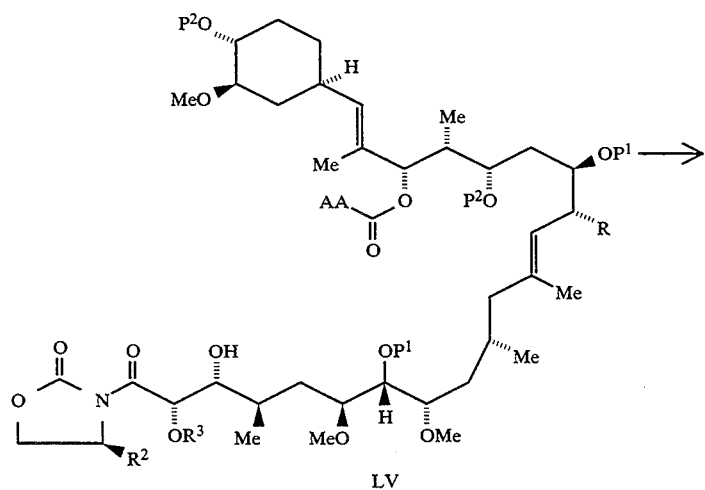
LV -continued

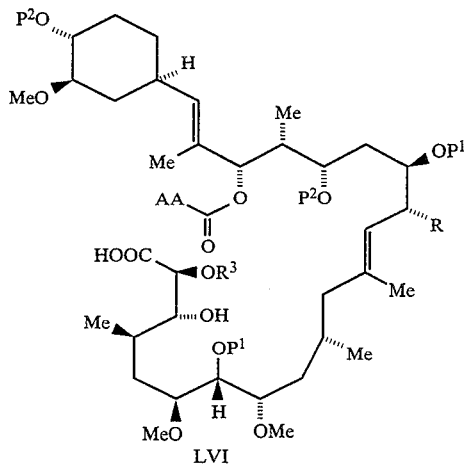
LVI (e) contacting carboxylic acid LVI with a P-silylating agent in an anhydrous inert organic solvent containing an amine proton acceptor at 0°–10° C. for a sufficient time to form the protected amino acid LVIA;

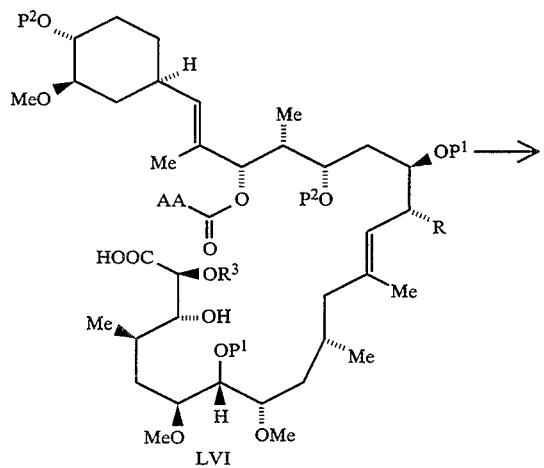
LVI

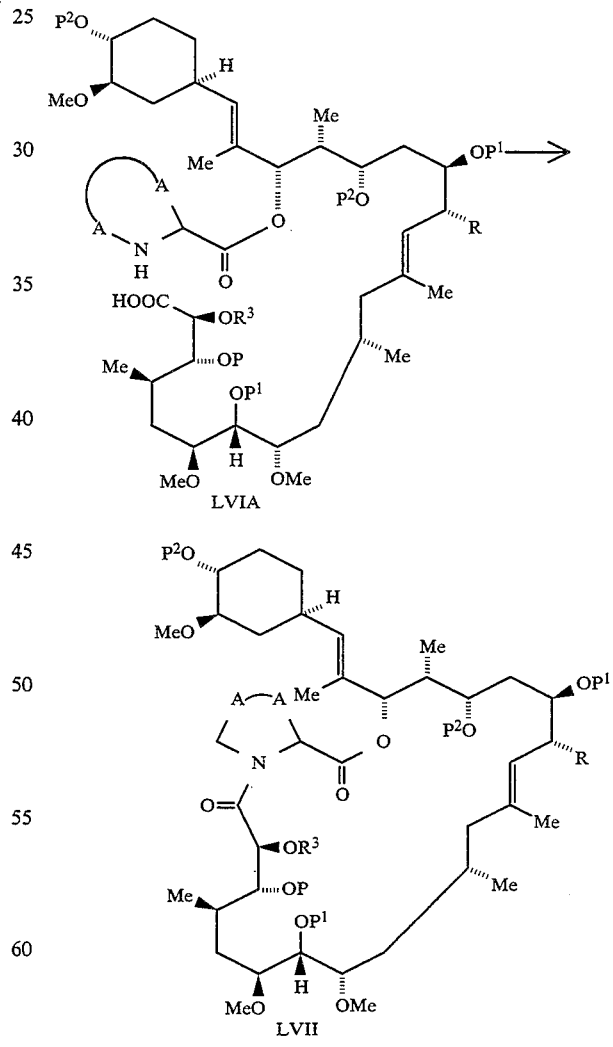

(f) contacting LVIA with a cyclizing agent in an anhydrous inert organic solvent containing a tertiary amine, an inert atmosphere, at 20°–30° C., for a sufficient time to allow the secondary amine of AA to condense with the free carboxylic acid to form LVII;

(g) contacting LVII in an anhydrous inert organic solvent with 2,3-dichloro-5,6-dicyano-1,4-benzoquinone at 20°–30° C. for a sufficient time to form LVIII and then contacting the resulting mixture with trifluoroacetic acid/H₂O at 20°–30° C. for a sufficient time to form the diol LIX;

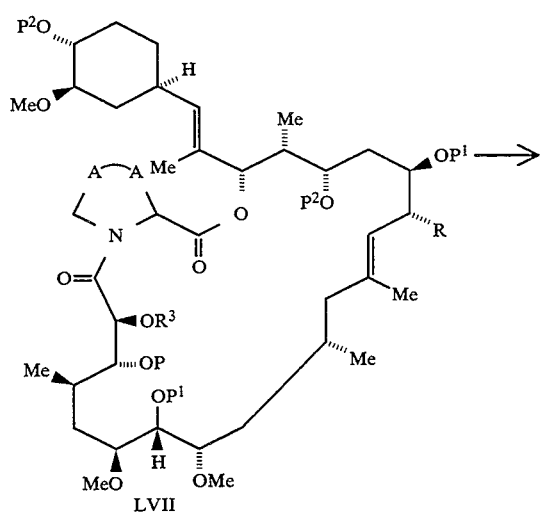
LVII

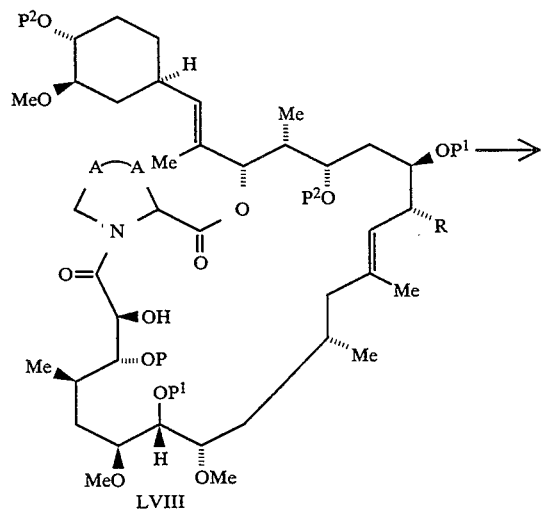
LVIII

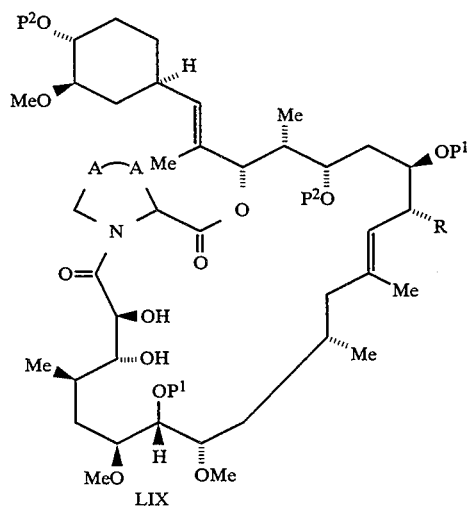
LIX (h) contacting diol LIX with oxalyl chloride, dimethyl sulfoxide, triethylamine, in an anhydrous inert organic solvent at −70° to −80° C., in an inert atmosphere, for a sufficient time to form the diketo LX:

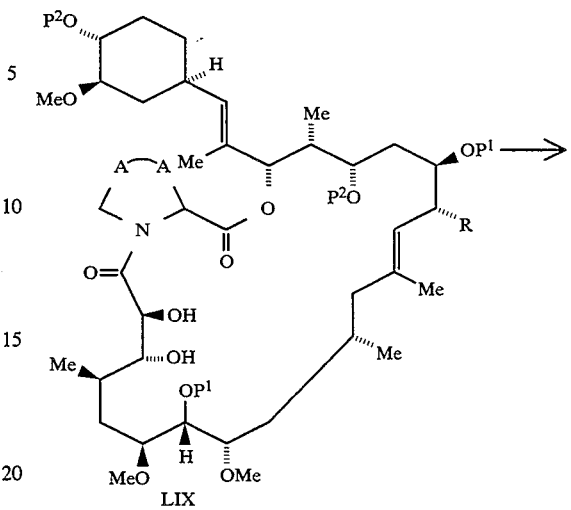
LIX

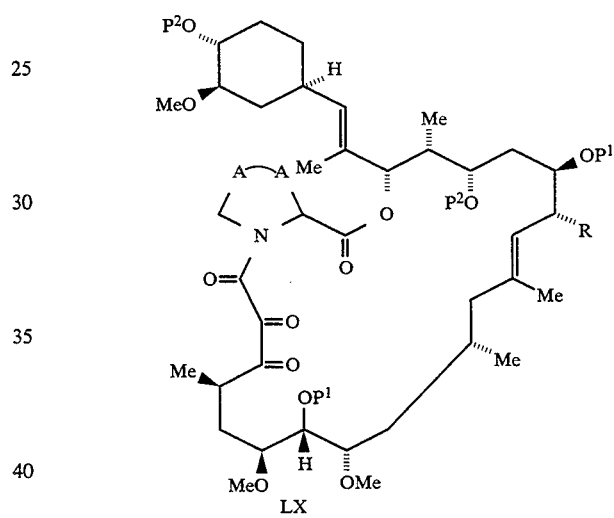
LX (i) contacting diketo LX with aqueous HF in an inert organic solvent at 0°–10° C. for a sufficient time to form the C-22 dihydro analog LXI;

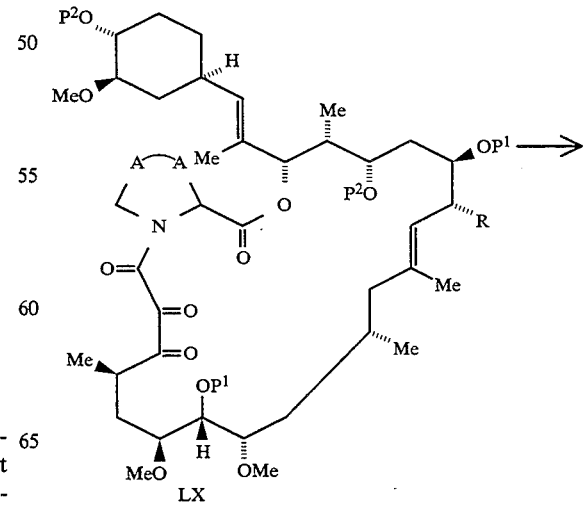
LX

-continued

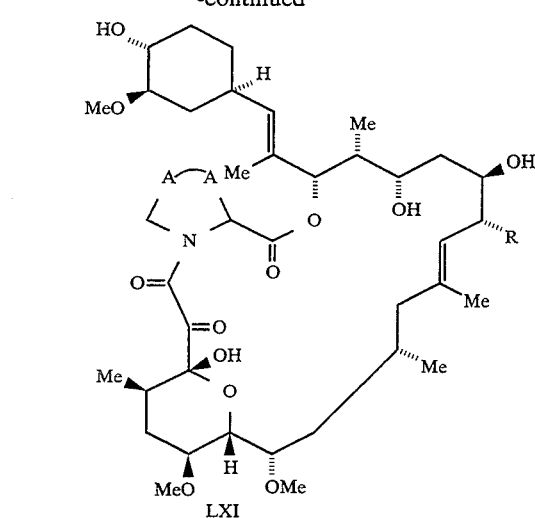
LXI (j) contacting compound LXI with a P-silylating agent in an anhydrous organic solvent, in the presence of an amine proton acceptor at 0°–5° C., in an inert atmosphere, for a sufficient time to form the bis-P-silylated compound LXII;

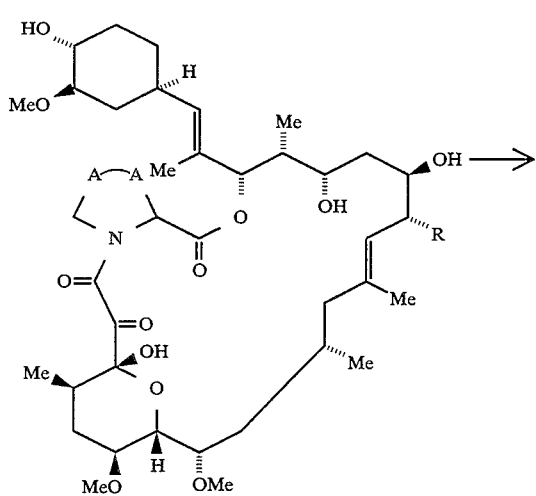
LXI

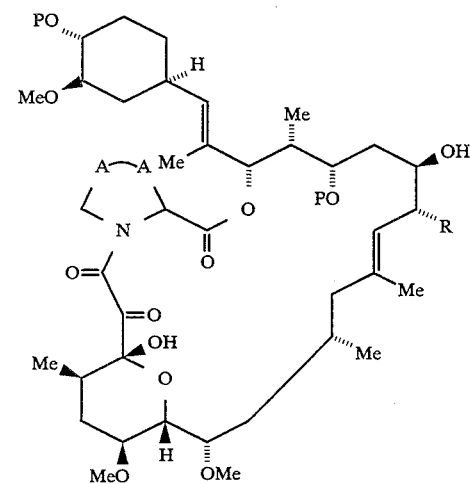
LXII (k) contacting LXII with perioindane in an anhydrous organic solvent and a tertiary amine under nitrogen at 20°–30° C. for a sufficient time to form the ketone LXIII;

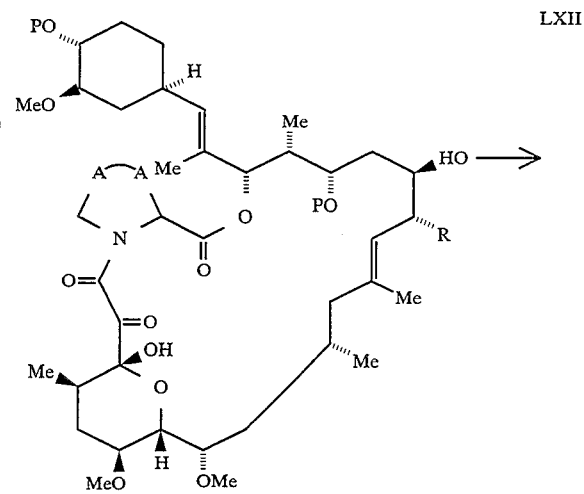
LXII

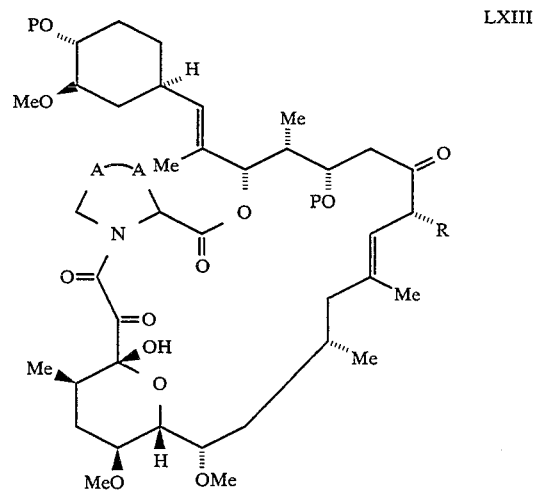
LXIII (l) contacting LXIII with aqueous HF in an inert organic solvent at 0°–5° C. for a sufficient time to form the FK-506 type macrolide LXIV;

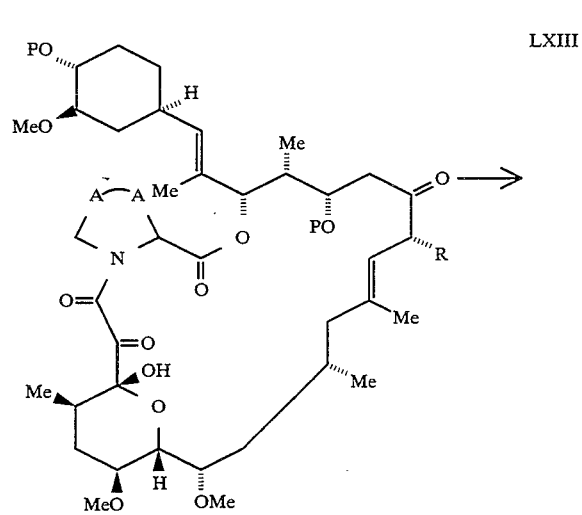
LXIII

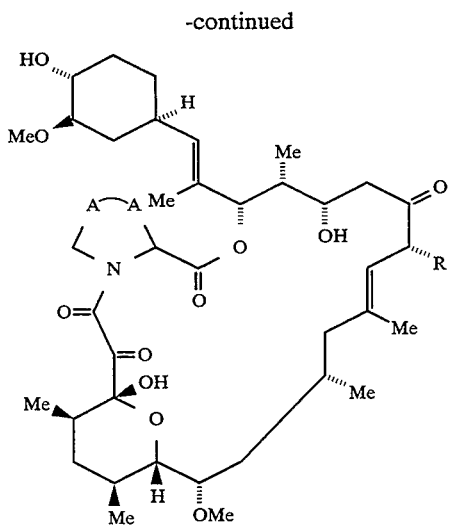

LXIV

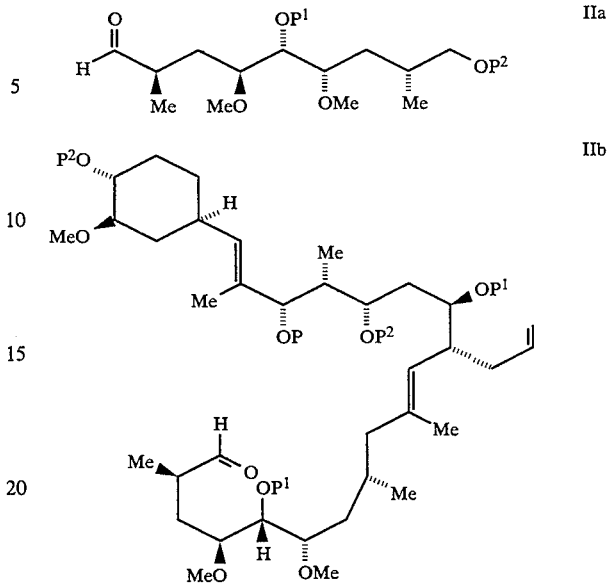

IIa

IIb

BRIEF DESCRIPTION OF THE INVENTION AND PREFERRED EMBODIMENTS

The invention can be readily understood by reference to Scheme i.

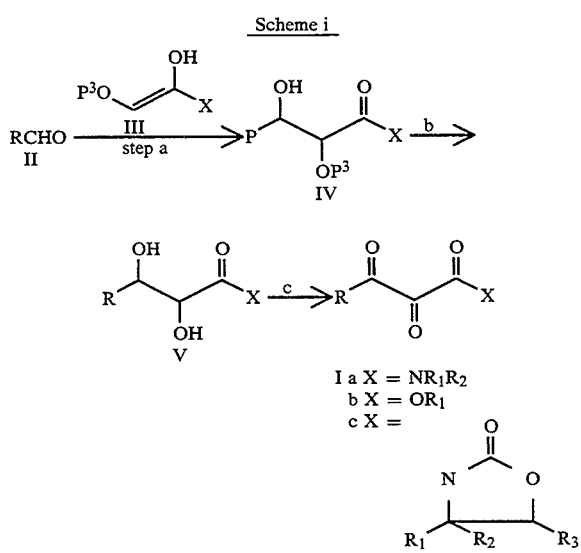

Scheme i

I a X = $NR_1R_2$
b X = $OR_1$
c X =

As is seen, aldehyde II is reacted in step (a) with a hydroxyl protected acetate enolate equivalent III to form the addition product IV, in which the 2-hydroxyl is protected.

The R group of the aldehyde is substituted or unsubstituted, linear or branched $C_1$-$C_{48}$ alkyl, wherein the substituent, inert under the reaction conditions, can be OH, $C_1$-$C_4$ alkoxy, $C_6$-$C_8$ phenoxy, SH, $C_1$-$C_4$ alkylthio, $C_6$-$C_8$ acylthio, $NH_2$, $N(C_1$-$C_4$ alkyl$)_2$, or the $C_{11}$-$C_{34}$ carbon framework of the FK-506 molecule.

Representative examples of R are isopropyl, n-butyl, isobutyl, and the like. Preferred are aldehydes IIa and IIb below. $P^3$ in IV is chosen from standard protecting groups, e.g. p-methoxybenzyl and is preferably not trihydrocarbosilyl.

The enolate III contains an X group which can be $NR_1R_2$, $OR_1$, $SR_1$,

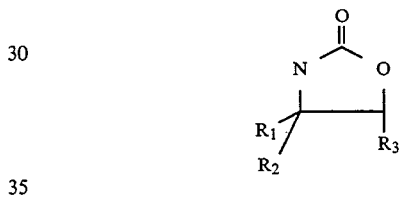

pipecolinic acid or ester; wherein $R_1/R_2/R_3$ are independently selected from: H, $C_1$-$C_4$ linear or branched alkyl, phenyl or benzyl, which may be substituted by halo or $C_1$-$C_4$ alkoxy.

Representative examples include p-methoxybenzyl, benzyl, phenyl, 2,4-dimethoxybenzyl, butyl, and the like. Preferred is the oxazolidinone moiety, where $R_1$=alpha H, and $R_2$=beta benzyl, $R_3$=H.

The protecting groups $P^1$ and $P^2$ can be conventional in the art and include linear or branched $C_1$-$C_{10}$ alkyl, $C_6$-$C_{10}$ acyl or benzyl, which can be substituted by one or more halo or $C_1$-$C_4$ alkoxy; tzihydrocarbosilyl, wherein said hydrocarbo group is independently chosen from $C_1$-$C_4$ linear or branched alkyl, phenyl or benzyl, including mixtures thereof.

Representative examples of trihydrocarbosilyl groups include trimethyl-, triethyl-, isopropyldimethyl-, t-butyldimethyl-, triisopropyl-, triphenyl-, tribenzyl-, phenyldimethyl-, benzyldimethyl-, diethylisopropylsilyl, and the like with the stipulation that $P^1$ can be removed in the presence of $P^2$.

Representative examples of $P^3$ groups include p-methoxybenzyl, trichloroethyl; 2,4-dimethoxybenzyl and the like. Preferred is p-methoxybenzyl.

The cation M is selected from Li, Na, K, Cs, Ca, Al, Zn, Ti, Sn and B(alkyl)$_2$. Representative examples of B(alkyl)$_2$ are $BMe_2$, $B(nBu)_2$, $B(Et)_2$, and the like. Preferred as cation M in the process is $B(nBu)_2$, where nBu is n-butyl.

The starting aldehydes II are known and can be prepared by conventional techniques in the literature. The $C_{11}$-$C_{34}$ FK-506 carbon framework is described herein.

The starting enolates III can be prepared as described in the literature reference: Evans, D. A.; Kaldor, S. W., and Jones, T. K., Presentation 196th ACS National Meeting, ORGN 177, 178, Los Angeles, 1988; Evans, D. A.; Bender, S. L.; Morris, J.; J. Am. Chem. Soc., 1988, 110, 2506.

The conditions under which step (a) is conducted includes reacting aldehyde II and enolate III together under an inert atmosphere, e.g. dry nitrogen or argon, in an anhydrous, inert organic solvent, e.g. a $C_2$-$C_6$ ether, i.e. tetrahydrofuran, methylene chloride, toluene, in the temperature range of $-100°$ C. to $20°$ C., preferably $-50°$ to $0°$ C., for a sufficient time to produce the addition product IV. Time required is generally in the range of 3 to 24 hours. Isolation is generally accomplished by quenching with aqueous hydrogen peroxide followed by extraction. Purification is generally accomplished by chromatography on Silica gel.

Yields are generally in the range of 70–95% based on II.

Step (b) of the process is the deprotection of the 2-hydroxyl group, which is a conventional step in the art.

If $P^3$ is p-methoxybenzyl (PMB), then IV is treated at $0°$–$100°$ C., preferably $25°$ to $50°$ C., in a solvent such as (generic), preferably ethyl acetate, with a hydrogen atmosphere at a pressure of 1–10 atmospheres, preferably 1 atmosphere, in the presence of 5–15% palladium hydroxide on carbon, for a sufficient time, e.g. 1 to 24 hours, to form diol V.

However, if olefin moiety is present, as with FK-506, then IV is silylated, e.g. with triethylsilyloxy triflate (TESOTf)/2,6-lutidine, then treated with dichlorodicyanoquinone, dichloromethane, water (18:1) at $20°$ C. for 1 to 20 hours, preferably 4 hours, to remove the PMB group, then followed by trifluoroacetic acid (TFA)/$H_2O$/THF to produce V.

Where $P^3$="troc" (2,2,2-trichloroethyl), step (b) consists of treating IV with a 1–10-fold excess, preferably 10-fold, of zinc powder in an anhydrous organic solvent, e.g. THF, dimethoxyethane, isopropylacetate, ethyl ether, in the presence of 1–100 equivalents, preferably 16 equivalents, of a carboxylic acid such as acetic acid, under an inert atmosphere, at a temperature of $20°$–$100°$ C., preferably with ultrasound irradiation, preferably at $20°$ C., for sufficient time, e.g. 2 hours, to produce the desired diol V.

Yields of step (b) product are generally 64% based on IV. Isolation and purification are accomplished by $NaHCO_3$ neutralization, extraction and silica gel chromatography, and are conventional.

Step (c) is conducted by treating the product V from step (b) under Swern oxidation conditions, with about 2–20 equivalents both of oxalyl chloride and dimethyl sulfoxide in an anhydrous organic solvent, e.g. dichloromethane, 1,1,2,2-tetrachloroethane, preferably dichloromethane at a temperature in the range of $-78°$ C. to $0°$ C., preferably $-78°$ to $-60°$ C., for a sufficient time, e.g. 1 to 5 hours, then adding 5 to 10 equivalents of $Et_3N$ and holding at $-30°$ C. for 1 hour to form the tricarbonyl compound I in yields which can range from 20 to 90% based on V.

The utility of compounds of Structure I is they are intermediates for FK-506 type immunosuppressants.

Isolation, purification of the above compounds as well as apparatus for carrying out the reactions are conventional.

In the case of the synthesis of the FK-506 23-membered macrocyclic system (1), a slight modification of the order of the above reactions is necessary to minimize interactions of the many functional groups present and to permit efficient construction of the macrocyclic ring prior to liberation of the C.1–C.10 pipecolinic acid derived tricarbonyl array (this array has been shown to be unstable under nucleophilic hydroxide mediated conditions and thus its introduction must be postponed until later in the synthesis; see U.S. patent application 256,784, filed Oct. 12, 1988 (Case Docket number 17820) by D. Askin et al and assigned to Merck & Co. Inc., hereby incorporated by reference for this particular purpose.

For this example, see the following Scheme ii, in which the order of reactions is presented.

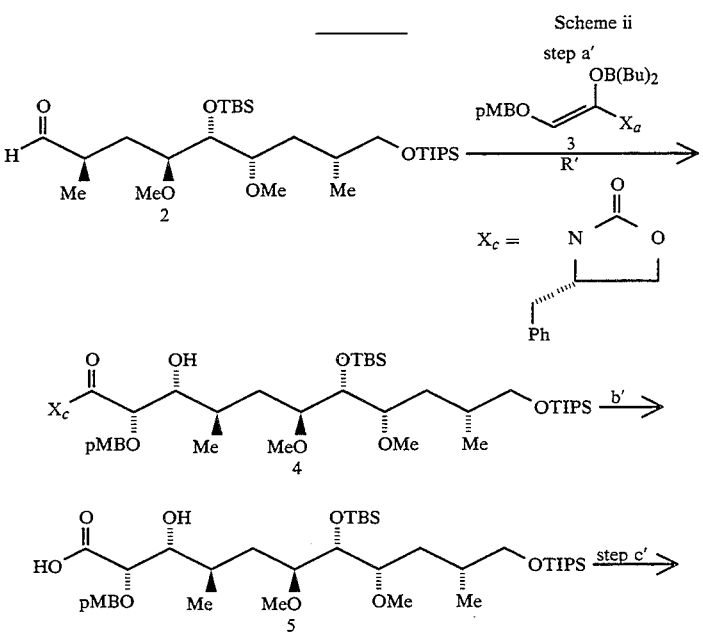

Scheme ii

-continued
Scheme ii

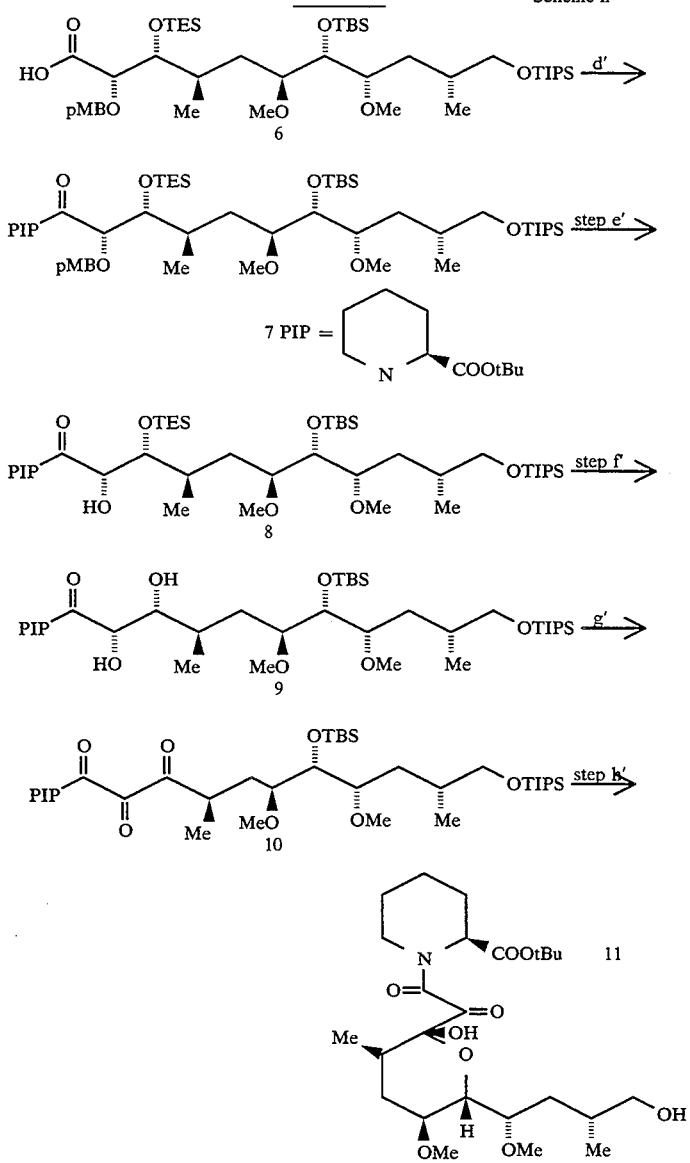

Step (a') comprises treating aldehyde 2 prepared from alcohol 21, Example 6, (D. Askin, R. P. Volante, R. A. Reamer, K. M. Ryan, I. Shinkai; Tett. Lett., 1988, 29, 277) by procedures described herein (Examples 6A–6I, Example 7) with the 2-p-methoxy-benzyl acetate dialkylborane derived enolate equivalent 3 (Example 1, within) to give the 2-p-methoxy-benzyl-3-hydroxyimide 4 as a single isomer. The conditions are generally the same as described above for step (a).

Step (b') comprises treating 4 with 1–10 equivalents of lithium hydroperoxide at 0°–10° C. in an organic solvent miscible with water, i.e. tetrahydrofuran, for 0.5–5 hr. to produce the hydroxy acid 5.

Step (c') comprises treating hydroxy acid 5 with 2–5 equivalents of triethylsilyltriflate/2,6-lutidine in an inert organic solvent, e.g. methylene chloride, at −50° to 0° C. to give the 3-triethylsilyloxy acid 6, isolated and purified after silica gel chromatography.

Step (d') comprises treating acid 6 with N-methyl 2-chloro-pyridinium iodide (1–5 equivalents) and the t-butyl ester of R-pipecolinic acid in an inert organic solvent, e.g. $CH_2Cl_2$, at −20° to 25° C. for 1–24 hr. to give the pipecolinic acid derived amide 7.

Amide 7 is deprotected in step (e') with 1–5 equivalents of dichlorodicyano-1,4-quinone in an inert organic solvent, e.g. $CH_2Cl_2$ plus water, at 0°–25° C. for 1–5 hr. to give the 2-hydroxy-3-triethylsilyloxy amide 8.

Step (f') comprises treating amide 8 with trifluoroacetic acid in an aqueous miscible organic solvent at 0°–25° C. to give the diol 9.

Step (g') comprises oxidizing diol 9 to the 2,3-diketoamide 10 by generally the same conditions as in step (c) above.

Deprotection of 10 by treatment with hydrofluoric acid in an organic solvent miscible with water, e.g. $CH_3CN$, yields the corresponding acyclic FK-506 analog 11.

In the case of 2,3-diketo-4,10-dimethyl-6,8-dimethoxy-7-triethylsilyloxy-1-triisopropylsilyloxy undecanoyl imide VI, the lactolization comprises treating VI with 1–10 equivalents of trifluoroacetic acid in an anhydrous inert organic solvent, preferably THF, at −10° to 50° C., preferably 20° to 25° C., for sufficient time, e.g. 1 hour, to produce the lactol VII.

Other FK-506 type macrolides can be prepared via this invention process starting with intermediate 52. (See preparation of 52 from 38 in Example 24).

Condensation of 52 with N-protected secondary amino acids, e.g. N-t-Boc-sarcosine and N-t-Boc-proline, in an anhydrous inert organic solvent such as a $C_2$-$C_6$ ether, i.e. diethylether, or $C_1$-$C_2$ halogenated alkane, i.e. dichloromethane, at temperatures in the range of $-60°$ to $-20°$ C., in the presence of a dehydrating agent, i.e. dicyclohexylcarbodiimide, and an organic nitrogen proton acceptor, i.e. dimethylaminopyridine, produce condensation products, e.g. 53, 66, which lead to FK-506 type macrolides differing in the $C_1$-$C_{10}$ segment.

N-t-Boc-sarcosine, when condensed with 52 as in Example 25, leads to the $C_1$-$C_{10}$ sarcosine FK-506 derivative as illustrated through Examples 26-36. Note that after the condensation in Example 25, the compound 53 is analogous to the N-t-Boc-pipecolinic analog 40, which leads to the synthesis of FK-506 through the reaction steps outlined in Examples 12-22.

Similarly, N-t-Boc-L-proline, when condensed with 52 as in Example 37, leads to FK-525 through the same series of reaction steps as described specifically in Examples 37-48.

Further, where the generic form of 52 is used, i.e. structure XI, where R can be allyl, propyl, ethyl or methyl as described in Ser. No. 07/374,608 (Case 17931), filed 30 Jun. 1959, now U.S. Pat. No. 5,164,525 and hereby incorporated by reference for this particular purpose, the proline and sarcosine analogs, inter alia, can be prepared. For example, where R=ethyl, the corresponding FK-520 analogs can be obtained.

Other secondary amino acids (e.g. in their N-protected form, e.g. N-t-Boc) can also be employed in the synthesis starting with the compound 52 condensation step and includes all naturally occurring amino acids and those known synthetic variations in the art which include those of the following formulae:

Acyclic Secondary Amino Acids

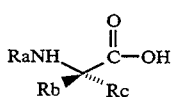

where $R_a$=$C_1$-$C_{10}$ alkyl, aryl, or substituted alkyl; $R_b$=H, $C_1$-$C_{10}$ alkyl, aryl, or substituted alkyl; and $R_c$=H, $C_1$-$C_{10}$ alkyl, aryl, or substituted alkyl, said substituents, including halo, $C_1$-$C_4$ alkoxy, e.g. chloro, methoxy, and the like.

Representative examples include N-methyl, N-ethyl, N-benzyl, N-phenyl substituted L- and D-forms (and racemates) of alanine, valine, leucine, isoleucine, phenylalanine, tyrosine, diiodotyrosine, thyroxine, serine, threonine, methionine, cysteine, cystine, aspattic acid, glutamic acid, lysine, arginine, known synthetic variants thereof, sarcosine, and the like;

Cyclic Secondary Amino Acids

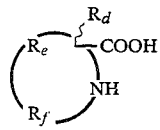

where $R_d$=H, $C_1$-$C_{10}$ alkyl, aryl or branched alkyl, which may be in the alpha or beta configuration; $R_e$ and $R_f$ are carbon-containing chains joined with NH to form a 4-10 membered carbon-nitrogen ring, which can be saturated, unsaturated or partially unsaturated, can contain one or more O, S or N heteroatoms and which can be ring substituted.

The above secondary amino acids are converted to their N-t-Boc protected form, by conventional procedure, and can be utilized in the place of sarcosine, proline, or pipecolinic acid.

Representative examples include L- and D-forms of proline, hydroxyproline, N-methyltryptophan, M-methylhistidine, 2-pipecolinic acid, known synthetic variants thereof, and the like, wherein said substituents include halo, $C_1$-$C_4$ alkoxy, i.e. chloro, methoxy, and the like.

The general synthetic scheme leading to the FK-506 type macrolide starting with the condensation product of 52 and an N-protected amino acid (e.g. products 53, 66, and 40, originally produced from the dithiane 39) can be readily seen by the synthesis of the sarcosine analog outlined in Examples 25-36.

The condensation step, as described above, leads to the dimethylacetal condensation product 53.

The dimethylacetal 53 is converted to the aldehyde 54, by treatment with glyoxylic acid and acetic acid under a dry nitrogen atmosphere at 25°-40° C. in an inert organic solvent, e.g. ether or halogenated alkanes, i.e. dichloromethane.

The aldehyde 54 is condensed with the chiral agent p-methoxybenzylacetimide in a dry organic solvent, e.g. toluene, at $-60°$ to $-30°$ C. under a $N_2$ atmosphere in the presence of an organic amine base, e.g. triethylamine and a dialkylboron reagent, e.g. dibutylboron triflate to yield the product 55.

The product 55, is oxidized with aqueous hydrogen peroxide in solvent tetrahydrofuran/$H_2O$ at 0° C. in the presence of lithium hydroxide to produce the carboxylic acid 56.

The carboxylic acid 56 is deprotected at the N-t-Boc site and hydroxyl protected by treatment with an organic amine base, e.g. 2,6-lutidine and a trialkylsilylating agent, e.g. triethylsilyltriflate, in an inert organic solvent, e.g. dichloromethane, at 0°-5° C. to yield the amine-acid 56A.

The amine-acid 56A is ring closed by treatment with 2-chloro-N-methylpyridinium iodide in an organic solvent, e.g. dichloromethane, in the presence of an organic proton acceptor, e.g. triethylamine, at room temperature, to produce the sarcosine analog of hexahydro FK-506, 57.

Deprotection of two hydroxyl groups adjacent to the sarcosine moiety in 57 is accomplished by treatment with, e.g. 2,3-dichloro-5,6-dicyano-1,4-benzoquinone, in dichloromethane/water at 25° C. and then THF/$H_2O$/trifluoroacetic treatment at 25° C. to yield the diol 59.

The diol 59 is oxidized to the triketo analog 60, by treatment under Swern conditions with oxalyl chloride and dimethylsulfoxide in methylene chloride at −75° to −80° C. in the presence of an organic proton acceptor, e.g. triethylamine.

The triketo analog 60 is converted to the analogous dihydro FK-506 analog 61 by treatment with, e.g. 50% aqueous HF in an inert organic solvent, i.e. acetonitrile, at −10° to 0° C.

The analog 61 is bis-protected by treatment with a silylating agent, e.g. triethylsilyl chloride, in the presence of an organic base, e.g. pyridine, which also serves as a solvent, at 0°–5° C. under a dry $N_2$ atmosphere to yield the bis-protected alcohol 62.

The bis-protected alcohol 62 is oxidized to the bis-protected ketone 63 by treatment with perioindane in a solvent, e.g. chloroform, and the presence of pyridine at 20°–25° C. under a dry nitrogen atmosphere.

Deprotection of 63 by treatment with 50% aqueous HF in acetonitrile at 0°–5° C. yields the sarcosine FK-506 analog 64.

Following substantially the same above-described procedure, starting with the N-t-Boc proline product 66, the FK-525 product is produced following Examples 37–48.

Note that in the described FK-506 synthesis starting in Example 11, the N-t-Boc pipecolinic acid is condensed with the dithiane analog 38 to form 39, which is then hydrolyzed to the dimethyl acetal analog 40. Alternatively, the N-t-Boc pipecolinic acid can be condensed with 52 to form 40 and then carried through Examples 13–22 to final FK-506.

Further, other N-t-Boc protected secondary amino acids described above, can be condensed with 38 to form the condensation product and then converted to the analog of 40. However, use of 52 is preferred in the condensation of the protected amino acid.

The process of producing a general FK-type macrolide of structure LXIV begins with the generalized intermediate LII produced by the degradation process of an FK-506 type macrolide as described herein.

LII is condensed with an N-protected secondary amino acid "AA-COOH", the structure defined herein, in an inert anhydrous organic solvent, e.g. $C_1$–$C_4$ halogenated alkane, i.e. methylene chloride, or $C_2$–$C_4$ cyclic or acyclic ether, i.e., dimethyl ether, diethyl ether, tetrahydrofuran, dioxane, at −40° to 60° C., under an inert atmosphere, e.g., dry nitrogen or argon, in the presence of a dehydrating agent, i.e., decyclohexylcarbodiimide, for a sufficient time, e.g. 1–4 hours, to produce LIII, in about 90–98% yield. The product LIII can be purified by conventional means, e.g. HPLC (high pressure liquid chromatography) using silica gel and eluting with hexane/ethyl acetate.

LIII is next converted from the acetal form to the aldehyde by treating with glyoxylic acid and acetic acid in an anhydrous inert organic solvent, e.g. $C_1$–$C_4$ halogenated alkane or $C_2$–$C_4$ cyclic or acyclic ether, i.e. methylene chloride, under an inert atmosphere of dry $N_2$ or argon, at a temperature in the range of 10°–40° C., for a sufficient time, e.g. ½ to 4 hours, to form the aldehyde LIV in 90–95% which can be isolated and purified by conventional means, e.g. HPLC using silica and eluting with hexanes/ethyl acetate.

The aldehyde LIV is next condensed with the substituted acetimide XV of the structure:

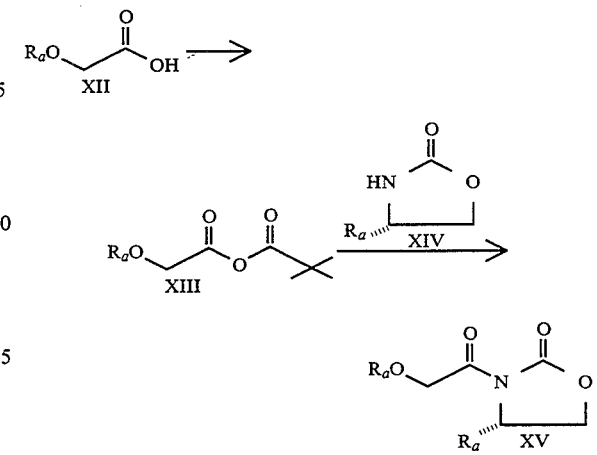

wherein $R_2$ is a chiral auxiliary group chosen from $C_1$–$C_4$ linear or branched alkyl or $C_7$–$C_9$ aralkyl, which can be substituted by halo, e.g. chloro, $C_1$–$C_4$ alkoxy, e.g. methoxy, wherein representative examples include methyl, isopropyl, t-butyl, benzyl, p-methoxybenzyl, and the like; and $R_3$ is a hydroxy protecting group, readily removable by catalytic hydrogenation, being a benzyl or substituted benzyl, wherein the substituents being halo, e.g., chloro, fluoro, $C_1$–$C_4$ alkoxy, e.g. methoxy, $C_1$–$C_4$ alkyl, e.g. methyl, and the like, preferred $R_3$ being p-methoxy benzyl.

XV can be produced by known methods in the art, for example, in the above scheme where $R_3OH$ is reacted with 2-bromoacetic acid in toluene at room temperature with sodium hydride to produce XII, which is treated with pivaloyl chloride and triethylamine in ether at −78° C. to give XIII which is then reacted with the (S)$R_2$ substituted oxazolidinone XIV in the THF at −78° C. with n-butyllithium to give XV.

The condensation of the aldehyde LV with the acetimide XV is carried out at −40° to −60° C. in an inert anhydrous solvent, e.g. $C_6$–$C_8$ aromatic hydrocarbon, i.e., benzene, toluene, xylene, and the like, an amine proton acceptor, e.g. triethylamine, tributylamine, pyridine, and the like, and a dialkylboron salt, e.g. diethylboron or dibutylboron triflate, under an inert $N_2$ or argon atmosphere, for a sufficient time, e.g. 1–4 hours to produce the imide LV in 75–85% yield, and isolated and purified by conventional means.

The imide LV is next treated with aqueous hydrogen peroxide in an aqueous-miscible organic solvent, e.g. THF, containing an alkali metal hydroxide, e.g. lithium hydroxide, at 0°–5° C., for a sufficient time, e.g. 1–4 hours, to form the carboxylic acid LVI, in 90–95% yield, which is isolated, purified by conventional HPLC means.

The carboxylic acid LVI, is next treated with a P-silylating agent, i.e. a silylating agent which places a "P" protecting group, as defined herein, onto the available unprotected 3-hydroxy group by treating LVI with a P-silylating agent, e.g. triethylsilyltriflate in an inert, anhydrous organic solvent, e.g. $C_1$–$C_4$ halogenated alkane, e.g. methylene chloride, in the presence of an amine proton acceptor, e.g. 2,6-lutidine, at 0° C. for a sufficient time, e.g. ½ to 2 hours, at 0°–10° C., to form the 3-protected LVIA structure in 50–70% yield, isolated and purified by conventional procedures. During this step, the N-protected secondary amino acid, AA, also undergoes hydrolysis of the N-protecting group preparatory to the cyclization in the next step.

The cyclization of LVIA to the FK-type macrolide LVII is carried out by treating LVIA with a cyclizing agent, e.g. 2-chloro-N-methylpyridinium iodide, in an inert, anhydrous organic solvent, e.g. $C_1$-$C_4$ halogenated alkane, e.g. methylene chloride, under a dry nitrogen or argon atmosphere, at 20°-30° C. for a sufficient time, e.g. 1-24 hours, to form LVII, in 50-70% yield, isolated and purified by conventional means.

LVII is then deprotected by hydrolyzing off $R_3$ first in $C_1$-$C_4$ halogenated alkane, e.g. methylene chloride, containing a small amount of ester, e.g. 1% by volume, at 20°-30° C. with 2,3-dichloro-5,6-dicyano-1,4-benzoquinone for a sufficient time to form a mixture of alcohols containing LVIII. The mixture is isolated and treated with trifluoroacetic acid in THF/$H_2O$ at 20°-30° C. for 1-5 hours to form the diol LIX in 80-90% yield and isolated and purified by conventional means.

LIX is then oxidized to the diketo LX macrocycle by treating LIX under Swern conditions using oxalyl chloride and dimethylsulfoxide in anhydrous, inert solvent, e.g. $C_1$-$C_4$ halogenated alkane, e.g. methylene chloride, and a tertiary amine, e.g. triethylamine, at −80° to −70° C. for a sufficient time, e.g. 1-5 hours, to form the diketo LX in 80-90% yield, isolated and purified by conventional means.

The diketo LX is cyclized to the hemiacetal form LXI by treating LX with 50% aqueous HF in an inert solvent, e.g. acetonitrile, at 0°-5° C. for a sufficient time, e.g. 1-10 hours, to replace LXI in 70-90% yield, isolated and purified by conventional means.

LXII is next produced by treating LXI with two equivalents of a P-silylating agent, e.g. triethylsilyltriflate, in the presence of an inert solvent, e.g. methylene chloride, and an amine proton acceptor, e.g. 2,6-lutidine, or in pyridine, which acts as both solvent and proton acceptor under a dry nitrogen atmosphere at 0°-5° C. for a sufficient time, e.g. 1-4 hours to yield the bis-protected LXII.

LXII is next oxidized with Dess-Martin perioindane (see *J. Org. Chem.*, 1988, Vol. 53, p. 4422) in an inert anhydrous solvent, e.g. methylene chloride, under an inert atmosphere, e.g. $R_2$, and in the presence of an amine base, e.g. pyridine, at 20°14 30° C., for a sufficient time, e.g. ½ to 3 hours to produce the bis-protected ketone LXIII, in 80-90% yield, isolated and purified by conventional means.

LXIII is then converted to final product LXIV, the FK-type macrolide, by treating with deprotection conditions, e.g. aqueous HF in acetonitrile at 0°-5° C. for 1-4 hours to yield LXIV in 80-90% yield, which is isolated and purified by conventional means.

The following examples are illustrative of carrying out the invention and should not be construed as being limitations on the scope and spirit of the instant invention.

EXAMPLE 1

Preparation of 2-P-Methoxybenzyl-Acetic Acid Phenyl Alanine Derived Oxazolidinone Imide, 15

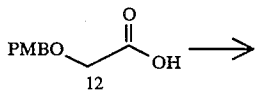

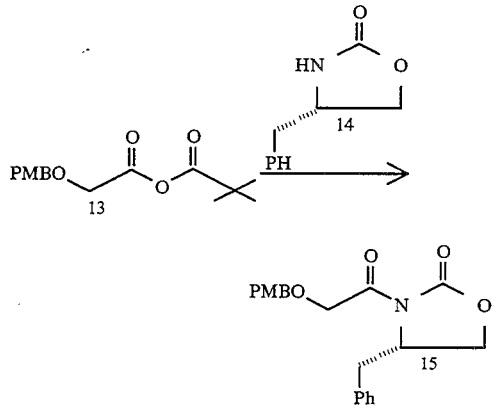

A. Preparation of 12 p-Methoxybenzyl alcohol (83.1 g) was dissolved in 75 ml of toluene and added dropwise (under a nitrogen atmosphere) over a period of 30 min. to a suspension of sodium hydride (53 g of a 60% oil dispersion, 2.20 equivalents) in 300 ml of toluene. The internal temperature rose from 24° C. to 35° C. during the addition. After hydrogen evolution had ceased (ca. 20 min), 2-bromoacetic acid (in 400 ml of toluene) was added over 1 hour dropwise under a nitrogen atmosphere keeping the internal temperature below or equal to 40° C. The addition of 2-bromoacetic acid was highly exothermic and external cooling was necessary. After 45 min., the mixture was diluted with 400 ml of toluene and heated at 95° C. for 2 hr. The mixture was cooled to 25° C. and quenched by the addition of 400 ml of water and the layers were separated. The aqueous phase was extracted with 2×200 ml of methyl-t-butyl ether. The aqueous layer was acidified with 60 ml of 1N $H_2SO_4$ and extracted with 3×400 ml of ethyl acetate. The combined organic phases were concentrated in vacuo to a yellow solid 12 (mp 49°-53° C., 103 g, 87% yield).

B. Preparation of 13, 15

2-p-Methoxybenzyl acetic acid 12 (3.92 g, 0.02 mol) was dissolved in 100 ml of ether and cooled to −78° C. under a nitrogen atmosphere. Triethylamine was added (2.86 ml, 0.0205 mol) followed by pivaloyl chloride (2.52 ml, 0.0205 mol). The mixture was warmed to 0° C. over 30 min. and then stirred at 0° C. for 2 hr. to give mixed anhydride 13. The solution was then cooled to −78° C. (SOLUTION A).

In a separate flask the (S) phenylalanine derived oxazolidinone 14 (3.45 g, 0.0195 mol) was dissolved in 30 ml of tetrahydrofuran and cooled to −78° C. under a nitrogen atmosphere. n-Butyllithium (14.3 ml of a 1.36M solution in hexane) was added via cannula, and then was stirred for 15 min at −78° C. (SOLUTION B).

Solution B was then added, via cannula, to solution A at −78° C. The resulting mixture was stirred 15 min at −78° C., warmed to 0° C. over 30 min, and then stirred for 1 hr at 0° C. Sixty ml of water was then added and the mixture was extracted with 3×50 ml of methylene chloride. The combined organic extracts were washed with 50 ml of saturated sodium bicarbonate solution and 50 ml of saturated sodium chloride solution and were dried over sodium sulfate. Concentration in vacuo and flash chromatography with silica gel (elution with 3:1, hexanes:ethyl acetate) gave the desired p-methoxybenzyl acetate derived oxazolidinone imide 15 (5.51 g).

EXAMPLE 2

(2S,3R,4R,6S,7R,8S,10R)-2-(p-methoxybenzyloxy)-3-hydroxy-4,10-dimethyl-6,8-dimethoxy-7-t-butyldimethylsilyloxy-11-triisopropylsilyloxy Undecanoate Phenyl Alanine Derived Oxazolidinone Imide, 4

EXAMPLE 3

(2S,3R,4R,6S,7R, 8S,10R) 2-(p-Methoxybenzyloxy)-3-triethylsilyloxy-6,8-dimethoxy-7-t-butyldimethylsilyloxy-11-triisopropylsilyloxy-undecanoic acid 6

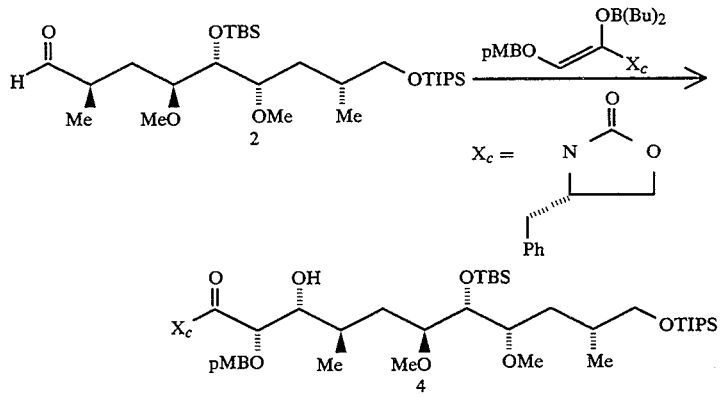

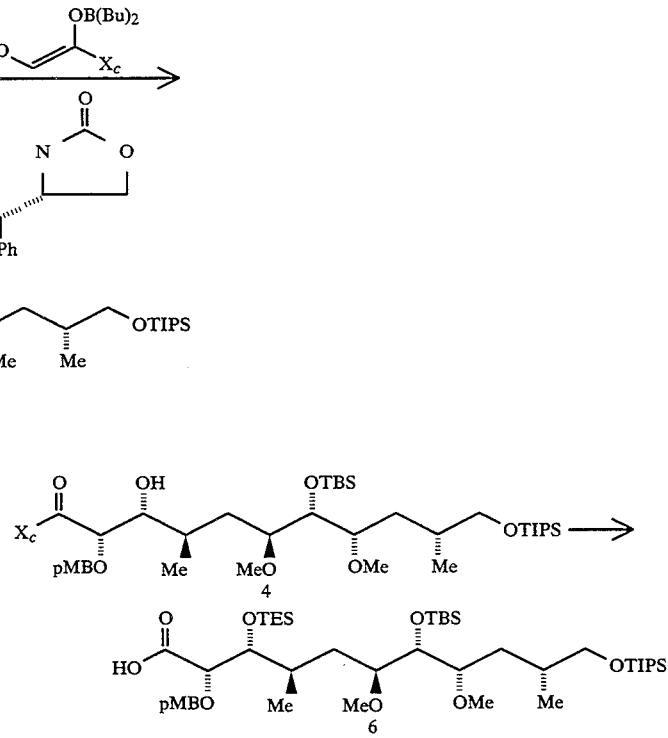

Acetamide 15 (100 mg, 0.281 mmol) was dissolved in 0.5 ml of methylene chloride under a nitrogen atmosphere and cooled to −50° C. Triethylamine (41 microliters, 0.290 mmol) was added followed by dibutylboron triflate (62 microliters, 0.270 mmol). The mixture was stirred under nitrogen at −50° C. for 2.5 hr and (2R,4S,5R,6S,8R)-2,8-dimethyl-4,6-dimethoxy-5-t-butyldimethylsilyloxy-9-triisopropylsilyloxy undecanal (2, 120 mg, 0.235 mmol) in 1.0 ml of methylene chloride was added. The resulting solution was aged at −50° C. for 1 hr and −30° C. for 16 hr. The mixture was warmed to 0° C. and one ml of pH 7 phosphate buffer was added followed by 1.0 ml of methanol and 3.0 ml of tetrahydrofuran. Aqueous 30% hydrogen peroxide (1.0 ml) was added (temperature increased to 14° C.) and the solution was cooled to 0° C. and stirred for 1 hr. The mixture was extracted with 3×10 ml of ethyl acetate. The organic phases were combined, washed with 10 ml of saturated aqueous sodium bicarbonate, 10 ml of saturated sodium chloride solution, dried over sodium sulfate and concentrated in vacuo. Flash chromatography over silica gel (elution with 3:1 hexane/ethyl acetate gave the desired C.8–C.18 imide 4 (165 mg, 81% yield).

Oxazolidinone 4 (0.323g, 0.364 mmol) was dissolved in 6.1 ml of tetrahydrofuran containing 1.53 ml of water and the solution was cooled to 0° C. under a nitrogen atmosphere. Hydrogen peroxide (0.30 ml, 2.91 mmol) was added and then lithium hydroxide (LiOH.H2O, 31.0 mg, 0.73 mmol). The mixture was stirred at 0° C. for 25 min and 1.5 ml of saturated aqueous sodium sulfite was added. The mixture was stirred an additional 15 min at 0° C. and the tetrahydrofuran was removed in vacuo on a rotary evaporator. The residue was stirred at 0° C. with 15 ml of hexanes and 3 ml of water and then brought to pH 4.5 by the addition of 0.5M aqueous sodium bisulfate solution. The layers were separated and the aqueous phase was extracted with 4×13 ml of hexanes. The organic phases were combined, dried over sodium sulfate, and concentrated in vacuo to give 276 mg of acid 6 as an oil. The material was homogeneous by $^1$H NMR.

EXAMPLE 4

(2S,3R,4R,6S,7R,8S,10R) 2-(p-Methoxybenzyloxy)-3-triethylsilyloxy-4,10-dimethyl-6,8-dimethoxy-7-t-butyldimethylsilyloxy-11-triisopropylsilyloxyundecanoic acid derived (R)-O-t-butylpipecolinate derived amide 7

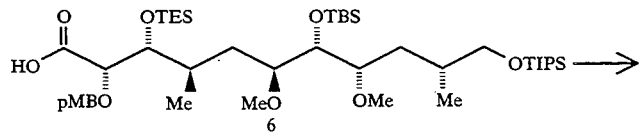

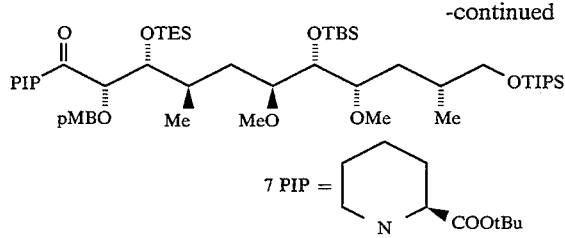

Acid 6 (256 mg, 0.35 mmol) was dissolved in 2 ml of methylene chloride under a nitrogen atmosphere and cooled to 0° C. Lutidine (0.155 ml, 1.33 mmol) and triethylsilyl triflate (0.241 g, 0.91 mmol) were added successively and the mixture was stirred for 1 hr at 0° C. Hexanes (4 ml) and water (2 ml) were added and the layers were separated. The aqueous layer was extracted with 4×4 ml of hexanes and the organic phases were combined, dried over sodium sulfate and concentrated in vacuo to a volume of ca. 1 ml. The solution was chromatographed on silica gel (400 mesh) eluting at a rate of 0.5 ml/min for 20 min to expose the material to fresh silica gel for this period of time (this procedure catalyzed the hydrolysis of the triethylsilyl ester group to the desired carboxylic acid moiety). The column was then eluted in standard fashion with 250 ml of hexanes-:ethyl acetate (2:1), 100 ml of hexanes:ethyl acetate (1:1) and 100 ml of hexanes:ethyl acetate (1:1 containing 0.5% acetic acid). Concentration of the column rich cuts gave 258 mg of an oil. This oil was dissolved in 2.0 ml of anhydrous methylene chloride and (R)-O-t-butyl-pipecolinate (113 mg, 0.61 mmol), triethylamine (108 mg, 1.07 mmol), and 2-chloro-N-methylpyridinium iodide (125 mg, 0.49 mmol) were added and the mixture was stirred under nitrogen at 25° C. for 3 hr. Hexanes (7 ml) and water (3 ml) were added and the layers were separated. The aqueous layer was extracted with 3×6 ml of hexanes, the organic phases were combined and washed with 1 ml of saturated aqueous sodium bicarbonate solution and dried over sodium sulfate. Concentration in vacuo gave 320 mg of an oil that was purified by flash chromatography on silica gel (15.5 g/400 mesh, eluting with 220 ml of 12:1 hexanes:ethyl acetate then 180 ml of 2:1 hexanes:ethyl acetate) to give 264 mg of amide 7 as an oil. The material was homogeneous by TLC and $^1$H NMR.

EXAMPLE 5

(2S,3R,4R,6S,7R,8S,10R) 2,3-Dihydroxy-4,10-dimethyl-6,8-dimethoxy-7-t-butyl dimethylsilyloxy-11-triisopropylsilyloxy-undecanoic acid derived (R)-O-t-butylpipecolinate amide 9

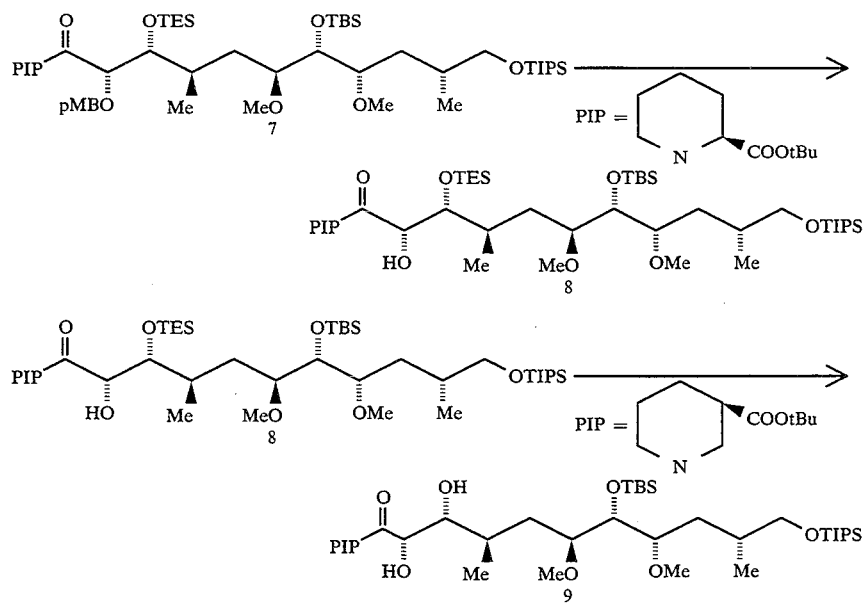

Amide 7 (25 mg, 0.025 mmol) was dissolved in a solution containing 0.3 ml methylene chloride and 0.015 mL of water. DDQ (28 mg, 0.12 mmol) was added and the mixture was stirred at 28° C. for 1.5 hr. The mixture was purified by flash chromatography on silica gel (4.5 g/400 mesh, eluting with 60 ml of methylene chloride then 80 ml of 3:1 hexanes:ethyl acetate) to give ca 18 mg of an oil containing both alcohol 8 and diol 9. The oil was dissolved in 0.5 ml tetrahydrofuran containing 0.12 ml of water and 25 microliters of dichloroacetic acid was added. The solution was stirred at 25° C. for 6 hr and 2 ml of saturated aqueous sodium bicarbonate solution was added. The layers were separated and the aqueous layer was extracted with 4×2 ml of ethyl acetate. The organic phases were combined, dried over sodium sulfate, and concentrated in vacuo to an oil. The oil was purified by flash chromatography on silica gel (4.5 g, 400 mesh, eluting with 80 ml of 4:1 and then 100 ml of 1:1 hexanes:ethyl acetate) to give diol 9 (15.1 mg). This material was homogeneous by $^1$H NMR.

EXAMPLE 5B (4R,6S,7R,8S,10R)-2,3-Diketo-4,10-dimethyl-6,8-dimethoxy-7-t-butyldimethylsilyloxy-11-triisopropylsilyloxy undecanoic acid derived (R)-O-t-butylpipecolinate derived amide 10

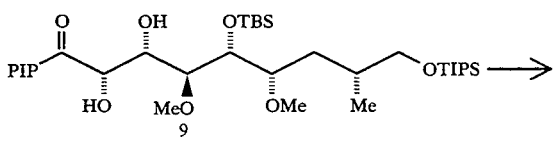

quenched by the addition of 10 ml of 0.5M sodium bisulfate solution and the mixture was extracted with 3×10 ml of ethyl acetate. The ethyl acetate phases were combined, dried over sodium sulfate, concentrated in vacuo, and purified by chromatography on silica gel (elution with 6:1 hexanes/ethyl acetate to give 64 mg, 85%, of the diketo amide 10 as an oil. This compound was homogeneous by both $^1$H and $^{13}$C NMR.

EXAMPLE 6

2-Oxo-2-(2'-hydroxy-3'-methyl-5'-methoxy-6'-(1''-hydroxyl-2''-methyl-4''-methoxybutan-4''-yl)-tetrahydropyran-2'-yl)-acetic acid derived (R)-O-t-butylpipecolinate amide 11

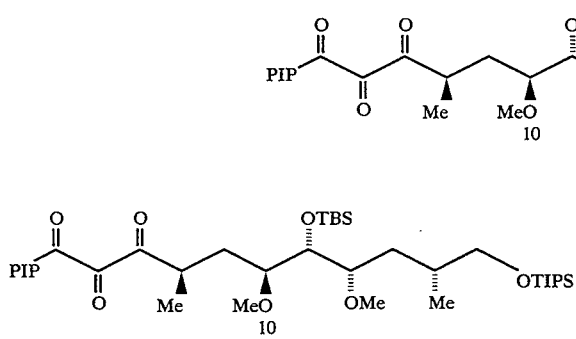

Oxalyl chloride (0.030 ml, 0.338 mmol) was dissolved in 0.5 ml of methylene chloride and cooled to −78° C. under a nitrogen atmosphere. Dimethyl sulfoxide (0.034 ml, 0.483 mmol) was added and the mixture was stirred for 20 min. The dihydroxy amide 9 (75 mg, 0.0966 mmol) dissolved in 0.5 ml of methylene chloride was added to the oxidant solution and the mixture was stirred at −78° C. for 3 hr. Triethylamine (0.094 ml, 0.676 mmol) was added and the mixture was warmed to −30° C. and stirred for 1 hr. The mixture was Diketo amide 10 (13.0 mg, 0.0168 mmol) was dissolved in 1.0 ml of anhydrous acetonitrile at 0° C. and 2 drops of 48% aqueous hydrofluoric acid was added. The mixture was stirred for 3 hr at 0° C. and was quenched with 2 ml of saturated aqueous sodium bicarbonate solution. The mixture was extracted with 3×5 ml of ethyl acetate. The organic phases were combined, dried over sodium sulfate and chromatographed on silica gel (eluting with 2:1 hexanes-ethyl acetate) to give 6 mg of hydroxy amide 11 as an oil. This material was homogeneous by $^1$H NMR.

EXAMPLES 6A–J

Preparation of Phosphine Oxide 33

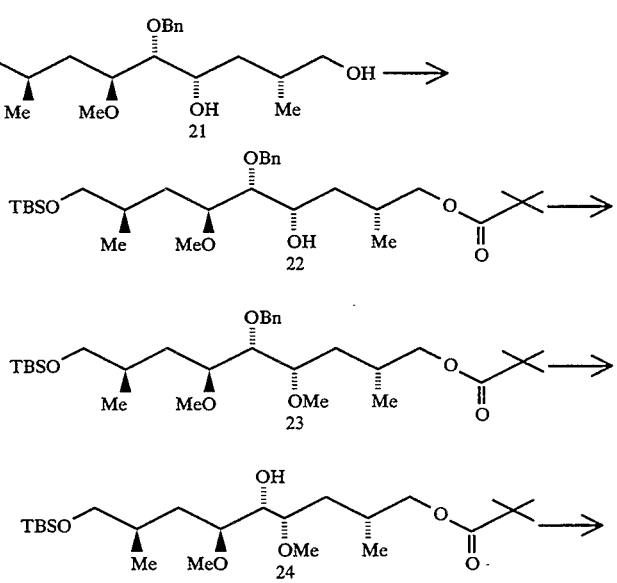

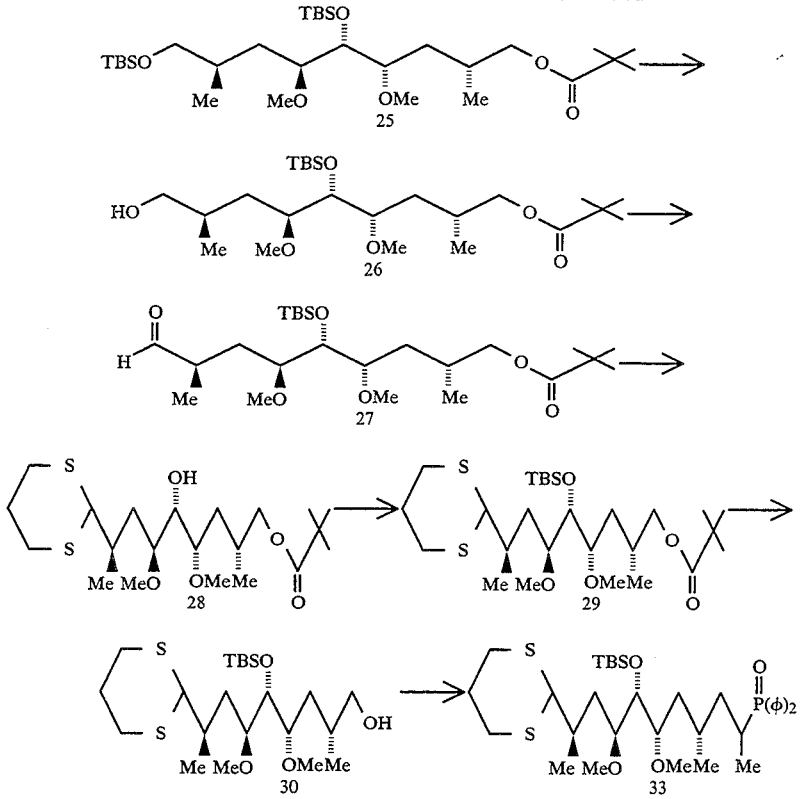

EXAMPLE 6A (2R,4S,5R,6S,8R)-1-Pivaloyloxy-2,8-Dimethyl-4-hydroxyl-5-benzyloxy-6-methoxy-9-t-butyldimethylsilyloxynonane, 22

Pivaloyl chloride (870 microliters, 1.05 equiv) was added to a solution of (2R,4S,5R,6S,8R)-2,8-dimethyl-4-hydroxy-5-benzyloxy-6-methoxy-9-t-butyldimethylsilyloxynonanol 21 (Source: Askin, D.; Volante, R. P.; Reamer, R. A.; Ryan, K. M.; Shinkai, I.; Tetra. Lett., 1988, 29, 277.) (3.07 g, 6.75 mmol) in 50 ml of anhydrous pyridine at 0° C. The solution was warmed to 25° C. over 1 hr and then was stirred at 25° C. for 16 hr. The reaction mixture was quenched by the addition of 10 ml of saturated aqueous sodium bicarbonate solution and then partitioned between 75 ml of water and 150 ml of diethyl ether. The aqueous phase was extracted with an additional 2×100 ml portions of ether. The organic phases were combined, washed with 1×50 ml of water and 1×50 ml of saturated sodium chloride solution, and dried over magnesium sulfate. Concentration in vacuo gave 3.67 g of 22 as a crude oil. The oil was purified by chromatography on 180 g of silica gel eluting with 5:1 hexanes:ethylacetate to give 3.52 g of pivaloate 22 (97% yield). The material was homogeneous by $^1$H and $^{13}$C NMR.

EXAMPLE 6B (2R,4S,5R,6S,8R)-1-Pivaloyloxy-2,8,dimethyl-4,6-dimethoxy-5-benzyloxy-9-t-butyldimethylsilyloxynonane, 23

Pivaloate 22 (3.52 g, 6.50 mmol) was dissolved in 50 ml of tetrahydrofuran at 25° C. and 523 mg of NaH (60% dispersion in mineral oil) and 4.0 ml of anhydrous methyl iodide (10 equiv) were added successively. The solution was stirred at 25° C. for 24 hr. The mixture was partitioned between 150 ml of diethyl ether and 50 ml of water. The aqueous phase was extracted with an additional 2×100 ml of ether. The organic phases were combined, washed with 100 ml of saturated sodium chloride solution and dried over magnesium sulfate. Concentration in vacuo gave 3.82 g of 23 as a crude oil. The material was purified by column chromatography on 190 g of silica gel eluting with hexanes:ethyl acetate (8:1) to give 3.58 g (99%) of dimethoxy pivaloate 23. This material was homogeneous by $^1$H and $^{13}$C NMR.

EXAMPLE 6C (2R,4S,5R,6S,8R)-1-Pivaloyloxy-2,8-dimethyl-4,6-dimethoxy-5-hydroxyl-9-t-butyldimethylsilyloxynonane, 24

Benzyl ether 23 (3.58 g, 6.48 mmol) was dissolved in 50 ml of ethyl acetate and treated with 950 mg of 20% palladium hydroxide on carbon. Hydrogen gas was bubbled into the solution at 25° C. for 1 hr. The mixture was filtered through celite and concentrated in vacuo to give 2.98 g of the alcohol 24 as an oil. This material was used directly in the subsequent transformation.

EXAMPLE 6D (2R,4S,5R,6S,8R)-1-Pivaloyloxy-2,8-dimethyl-4,6-dimethoxy-5,9-bis-t-butyldimethylsilyloxynonane, 25

Alcohol 24 (2.98 g, 6.48 mmol) was dissolved in 50 ml of methylene chloride at 25° C. and 2,6-lutidine (1.51 ml, 2.0 equiv) was added. t-Butyldimethylsilyl triflate (2.23 ml, 1.5 equiv) was added and the mixture was stirred at 25° C. for 10–15 min. The solution was poured in 40 ml of saturated aqueous sodium bicarbonate solution and extracted with 2×200 ml of methylene chloride. The combined organic phases were dried over magnesium sulfate and concentrated in vacuo to give 4.0 g of the bis-t-butyldimethylsilyl ether 25 as an oil. This material was homogeneous by $^1$H and $^{13}$C NMR and was used directly in the subsequent transformation.

EXAMPLE 6E (2R,4S,5S,6S,8R)-2,8-Dimethyl-4,6-dimethoxy-5-t-butyldimethylsilyloxy-9-pivaloyloxynonanol, 26

Bis-t-butyldimethylsilyloxy ether 25 (3.67 g, 6.36 mmol) was dissolved in a solution composed of 54 ml of tetrahydrofuran, 18 ml of water, and 0.9 ml of trifluoroacetic acid. The mixture was stirred at 25° C. for 5 hr. The mixture was partitioned between 200 ml of methylene chloride and 100 ml of saturated sodium bicarbonate solution. The aqueous phase was extracted with 2×200 ml of methylene chloride. The organic layers were combined, dried over magnesium sulfate, and concentrated in vacuo to yield 3.75 g of an oil. The oil was purified by chromatography on 190 g of silica gel eluting with hexanes:ethyl acetate (4:1) to give 2.675 g of primary alcohol 26. This material was homogeneous by both $^1$H and $^{13}$C NMR.

EXAMPLE 6F (2R,4S,5R,6S,8R)-2,8-Dimethyl-4,6-dimethoxy-5-t-butyldimethylsilyloxy-9-pivaloyloxynonanyl, 27

Oxalyl chloride (227 microliters) was dissolved in 5 ml of methylene chloride at −70° C. and dimethyl sulfoxide (308 microliters, 2.0 equiv) in 5 ml of methylene chloride was added. The solution was stirred at −70° C. for 1 hr and the alcohol 26 in 10 ml of methylene chloride was added via cannula. The resulting slurry was stirred at −70° C. for 1 hr and triethylamine (1.51 ml) was added via syringe. The mixture was warmed to −30° C. over 15–30 min. The reaction was quenched by the addition of 20 ml of 0.5M sodium bisulfate solution. The mixture was extracted with 3×75 ml of methylene chloride, the combined organic phases were backwashed with 1×75 ml of water, and dried over magnesium sulfate. Concentration in vacuo and chromatography of the resulting oil over 25 g of silica gel eluting with 10:1 hexanes/ethyl acetate gave 971 mg (97% yield) of the desired aldehyde 27. This material was homogeneous by $^1$H and $^{13}$C NMR.

EXAMPLE 6G (2R,4S,5R,6S,8R)-1-Pivaloyloxy-2,8-dimethyl-4,6-dimethoxy-5-hydroxy-8-(1′,3′-dithian-2′-yl)-nonane, 28

Aldehyde 27 (971 mg, 2.11 mmol) was dissolved in 25 ml of methylene chloride at 0° C. and propane-1,3-dithiol (318 microliters, 1.5 equiv) was added. Boron trifluoride etherate (519 microliters, 2.0 equiv) was added and the mixture was stirred at 0° C. for 1 hr. The reaction mixture was partitioned between 75 ml of methylene chloride and 25 ml of saturated sodium bicarbonate solution. The aqueous phase was extracted with 1×75 ml of methylene chloride and the combined organic phases were washed with 1×50 ml of saturated sodium bicarbonate solution and dried over magnesium sulfate. Concentration in vacuo and chromatography of the resulting oil over 25 g of silica gel eluting with 4:1 hexanes/ethyl acetate gave 892 mg (97% yield) of the dithiane 28 as an oil. This material was homogeneous by NMR.

EXAMPLE 6H (2R,4S,5R,6S,8R)-1-Pivaloyloxy-2,8-dimethyl-4,6-dimethoxy-5-t-butyldimethylsilyloxy-8-(1′,3′-dithian-2′-yl)-nonane, 29

Alcohol 28 (892 mg, 2.05 mmol) was dissolved in 25 ml of methylene chloride at 25° C. and 2,6-lutidine (0.48 ml, 2.00 equiv) was added. t-Butyldimethylsilyltriflate (0.71 ml, 1.50 equiv) was added and the mixture was stirred at 25° C. for 10–15 min. The solution was poured into 40 ml of saturated sodium bicarbonate solution and extracted with 2×100 ml of methylene chloride. The organic phases were combined, dried over sodium sulfate, and concentrated in vacuo to give 1.1 g of the silyl ether 29 as an oil. This material was used directly in the subsequent transformation.

EXAMPLE 6I (2R,4S,5R,6S,8R)-2,8-Dimethyl-4,6-dimethoxy-5-t-butyldimethylsilyloxy-(1′,3′-dithian-2′-yl)-nonanol, 30

Pivalate 29 (465.8 mg, 0.84 mmol) was dissolved in 20 ml of anhydrous tetrahydrofuran and cooled to 0° C. Lithium aluminum hydride (30.4 mg, 0.800 mmol) was added and the solution was stirred at 0° C. for 1.5 hr. The reaction mixture was diluted with 50 ml of diethyl ether. 50 ml of saturated aqueous sodium sulfate solution was added followed by 50 ml of ethyl acetate. The aqueous phase was extracted with an additional 2×100 ml of of ethyl acetate and the organic phases were combined. The combined organic layers were washed with 50 ml of saturated sodium chloride solution, dried over magnesium sulfate, and concentrated in vacuo to yield 390 mg of the alcohol 30 an oil (101% mass recovery). The material was homogeneous by both $^1$H and $^{13}$C NMR.

EXAMPLE 6J (b 1R*S*,3R,5S,6R,7S,9R)-2,4,10-Trimethyl-6,8-dimethoxy-7-t-butyldimethylsilyloxy-9-(1′,3′-dithian-2′-yl)-nonan-1-yl Diphenyl Phosphine Oxide, 33

Alcohol 30 (454 mg, 0.97 mmol) was dissolved in 3.0 ml of anhydrous pyridine and cooled to −30° C. Benzenesulfonyl chloride (0.249 ml, 2.0 equiv) was added and the mixture was stirred at −30° C. under a nitrogen atmosphere for 16 hr. The reaction mixture was poured into a mixture of 25 ml of ethyl acetate and 25 ml of 1N hydrochloric acid. The phases were partitioned and the organic layer was washed with 1×20 ml of 1N HCl and 20 ml of saturated aqueous sodium chloride solution. The ethyl acetate solution was then dried over sodium sulfate and concentrated in vacuo to an oil. The oil was purified by column chromatography over silica gel eluting with 5:1 hexanes/ethyl acetate to give 528 mg of the benzene sulfonate as an oil. The material was homogeneous by $^1$H and $^{13}$C NMR. Ethyl diphenyl phosphine oxide (400 mg, 1.74 mmol) was dissolved in 6 ml of anhydrous tetrahydrofuran under a nitrogen atmosphere and cooled to −78° C. n-BuLi (1.10 ml of a 1.5M solution in hexane, 1.65 mmol) was added and the mixture was stirred for 20 min. at −78° C. In a separate flask the benzene sulfonate (528 mg, 0.87 mmol) was dissolved in 4 ml of anhydrous tetrahydrofuran and placed under a nitrogen atmosphere. The benzenesulfonate solution was then added to the lithio-phosphine oxide anion solution while maintaining the temperature at −30° C. The reaction mixture was warmed to 0° C. over 30 min. and the reaction was quenched by the addition of 15 ml of saturated aqueous ammonium chloride solution. The mixture was extracted with 3×20 ml of ethyl acetate, the organic phases were combined, dried over sodium sulfate, and concentrated in vacuo to an oil. The oil was purified by column chromatography on silica gel eluting with 3:1 hexanes/ethyl acetate to give 467 mg (79%) of the desired phosphine oxide 33. The material was homogeneous by ¹H and ¹³C NMR.

EXAMPLE 7

Preparation of Aldehyde 2

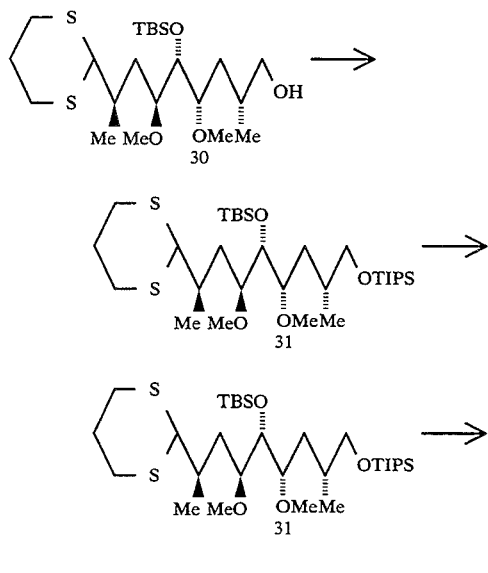

A. Preparation of (2R,4S,5R,6S,8R)-1-Triisopropylsilyloxy-2,8-dimethyl-4,6-dimethoxy-5-t-butyldimethylsilyloxy-8-(1′,3′-dithian-2′-yl)-nonane, 31

Alcohol 30 (2.0 mmol) was dissolved in 25 ml of methylene chloride at 25° C. and 2,6-lutidine (0.48 ml, 2.0 equiv) was added. Triisopropylsilyltriflate (0.71 ml, 1.50 equiv) was added and the mixture was stirred at 0° C. for 30 min. The solution was poured into 40 ml of saturated aqueous sodium bicarbonate solution and extracted with 2×100 ml of methylene chloride. The organic phases were combined, dried over sodium sulfate, and concentrated in vacuo give 1.1 g of silyl ether 31 as an oil. This material was homogeneous by NMR.

B. Preparation of (2R,4S,5R,6S,8R)-2,8-Dimethyl-4,6-dimethoxy-5-t-butyldimethylsilyloxy-9-triisopropylsiloxy-nonanal, 2

N-Chlorosuccinimide (460 mg, 3.4 mmol), silver nitrate (660 mg, 3.85 mmol), and 2,6-lutidine (1.0 ml, 8.6 mmol) were dissolved in 42 ml of methanol and stirred at 25° C. for 30 min. in the absence of light under a nitrogen atmosphere. Dithiane 31 (0.85 mmol) was added and the mixture was stirred an additional 1.5 hr at 25° C. The mixture was cooled to 0° C. and treated with 40 ml of saturated aqueous sodium sulfate solution, 40 ml of saturated aqueous sodium bicarbonate solution, and 40 ml of saturated sodium chloride solution. Water (40 ml) was added and the mixture was extracted with 4×50 ml of methylene chloride. The organic phases were combined, dried over sodium sulfate, and concentrated in vacuo to a volume of 20 ml. Glyoxylic acid (425 mg, 6.8 mmol) and acetic acid (0.40 ml, 6.8 mmol) were added and the mixture was stirred at 40° C. for 1 hr. The mixture was cooled, poured into 50 ml of saturated aqueous sodium bicarbonate solution, extracted with 2×50 ml of methylene chloride, and dried over sodium sulfate. The solution was concentrated in vacuo to an oil and chromatographed on silica gel (elution with hexanes:ethyl acetate, 10:1) to give aldehyde 2 (90% yield). This material was homogeneous by NMR.

EXAMPLE 8

(2R,3S,5S,6R,7S,1′R,3′R,4′R)-E-2-(Prop-2′-en-1′-yl)-3-t-butyldimethylsilyloxy-5-triisopropylsilyloxy-6,8-dimethyl-7-triethylsilyloxy-(4′-triisopropylsilyloxy-3′-methoxycyclohex-yl)-non-8-enal, 35

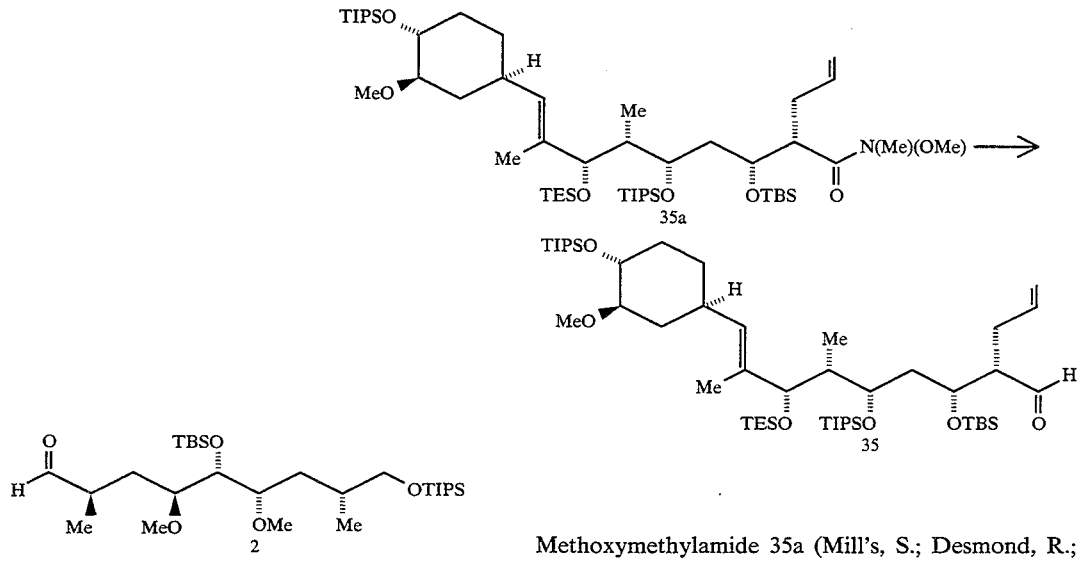

Methoxymethylamide 35a (Mill's, S.; Desmond, R.; Reamer, R. A.; Volante, R. P.; Shinkai, I. *Tet. Lett.*, 1988, 29, 281.) (1.63 g, 1.65 mmol) was dissolved in 13.0 ml of anhydrous tetrahydrofuran under nitrogen and cooled to −78° C. Diisobutylaluminum hydride (1.76 ml of a 1.5M solution in toluene, 2.64 mmol) was added and the resulting solution was warmed to −23° C. over 40 min. The mixture was stirred an additional 1.33 hr and warmed to −13° C. for 15 min. The solution was cooled to −78° C. and transferred via cannula to a vigorously stirred mixture of 1M aqueous solution of tartaric acid (14 ml) and hexanes (22 ml) at 0° C. The mixture was warmed to 25° C. and after stirring for 45 min the phases were separated. The aqueous portion was extracted with 2×25 ml of diethyl ether. The organic phases were combined, dried over sodium sulfate, and concentrated in vacuo to an oil. The oil was flash chromatographed on silica gel (elution with 1 L of 80:1 hexanes:ethyl acetate, 400 ml of 30:1, hexanes:ethyl acetate) to give 1.46 g of aldehyde 35 as an oil (95.5% yield). The material was homogeneous by NMR.

EXAMPLE 9

(1R,3S,4R,5S,7S,11R,12S,14S,15R,16S,1'R,3'R,4'R)-E,E-1-(1',3'-Dithian-2'-yl)-1,7,9,15,17-pentamethyl-3,5-dimethyloxy-,12-bis-t-butyldimethylsilyloxy-11-(prop-2'-en-1'-yl)-14-triisopropylsilyloxy-16-triethylsilyloxy-18-(4'-triisopropylsilyloxy-3'-methoxycyclohex-1'-yl)-octadeca-9,17-diene, 37

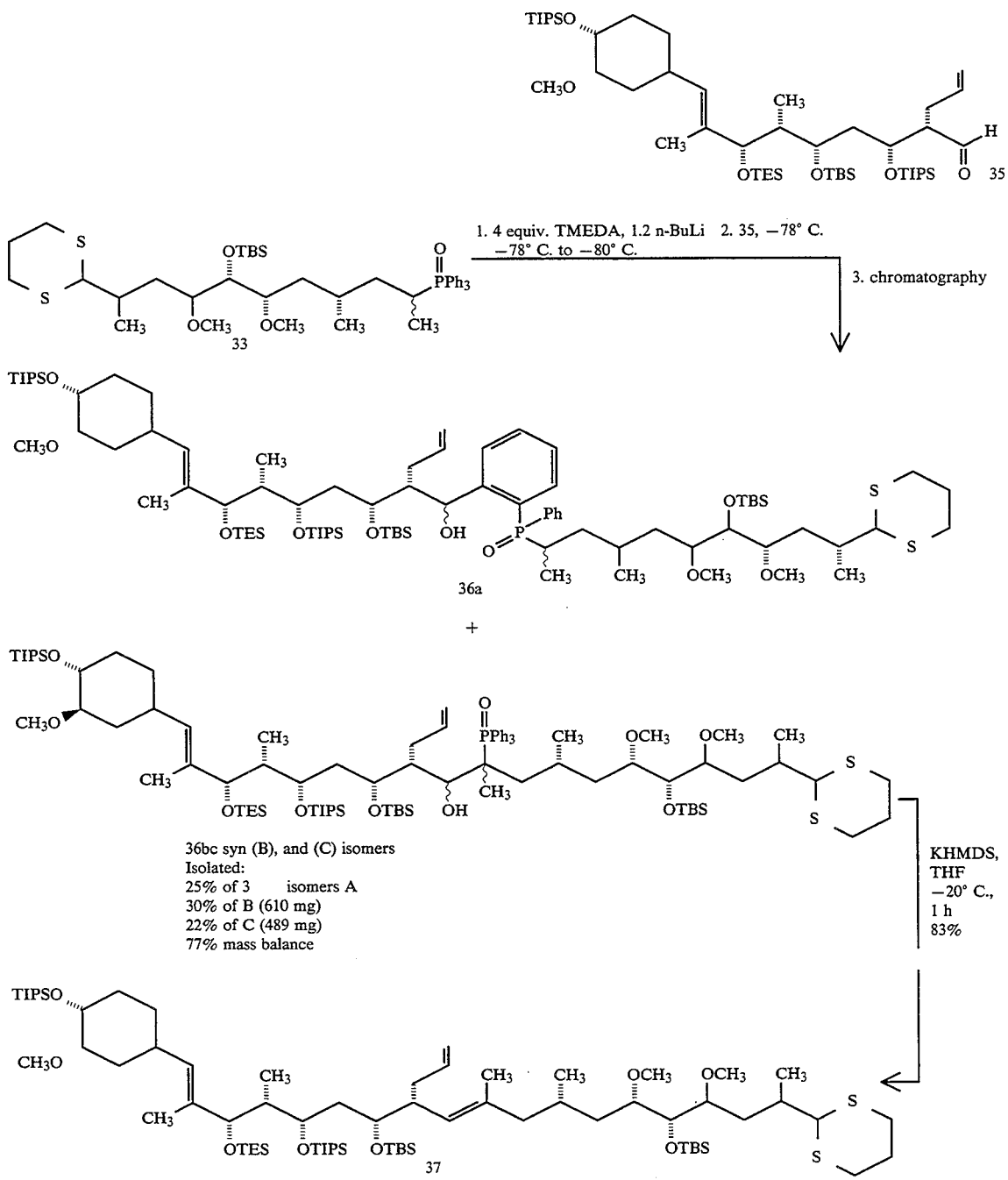

A. Synthesis

Phosphine oxide 33 (903 mg, 1.33 mmmol) was dissolved in 4.4 ml of anhydrous tetrahydrofuran containing tetramethylethylene diamine (0.803 ml, 5.32 mmol) under a nitrogen atmosphere and cooled to −78° C. n-BuLi (1.02 ml of a 1.56M solution in hexane, 1.59 mmol) was added dropwise via syringe over 4 min. The mixture was stirred at −78° C. for 30 min., warmed to −50° C., and stirred an additional 5 min. The solution was recooled to −78° C. and aged for 30 min. Aldehyde 35 (1.48 g, 1.20 equiv) was dissolved in 5 ml of anhydrous tetrahydrofuran and added to the phosphine oxide anion solution over a 10 min. period, while maintaining the solution temperature at −78° C. The mixture was stirred for 5 min. at −78° C. and 20 ml of a saturated aqueous ammonium chloride solution was added. The mixture was extracted with 3×50 ml of ethyl acetate. The organic layers were combined and dried over sodium sulfate. Concentration in vacuo gave an oil which was purified by chromatography on silica gel (elution with 8:1, hexanes:ethyl acetate) to give the desired diastereomeric hydroxy phosphine oxides 36 as an oil (609 mg, 30%).

B. Elimination

The E-olefin producing hydroxy-phosphine oxides 36 (609 mg, 0.379 mmol) were dissolved in 6 ml of anhydrous tetrahydrofuran and cooled to −20° C. under a nitrogen atmosphere. Potassium hexamethyldisilazane (1.14 ml of a 0.5M solution in toluene (0.569 mmol) was added and the mixture was stirred at −20° C. for 20 min. and then at 0° C. for 1 hr. Saturated aqueous ammonium chloride (30 ml) was added and the mixture was extracted with 3×30 ml of ethyl acetate. The combined ethyl acetate phases were dried over sodium sulfate and concentrated in vacuo to give 435 mg of olefin 37 as an oil (82% yield). This material was homogeneous by both $^1$H and $^{13}$C NMR.

H NMR δ 5.71(m,$H_{21b}$), 5.18(d,J=8.8,$H_{28}$), 4.99 (obs d,$H_{20}$), 4.95(m,$H_{21c}$), 4.19(d,J=3.4,$H_{10}$), 4.06(d,J=9.3,$H_{26}$), 3.91(dd,J=5.9,1.5,$H_{14}$), 3.84 (br dd,J=10.3,3.9,$H_{24}$), 3.55(m, $H_{32}$), 3.47(s, OCH$_3$), 3.48(obs m,$H_{22}$), 3.39(s, OCH$_3$), 3.34(s, OCH$_3$), 3.28(br d,J=9.8,$H_{13}$), 3.18(m, $H_{15}$), 2.99(m, $H_{31}$), 1.61(d,J=1.0, $C_{27a}H_3$), 1.55(br s, $C_{19a}H_3$).

$^{13}$C NMR (75.47 MHz): $δ_C$ 137.7 ($C_{21b}$), 135.8, 135.0($C_{27}$,$C_{19}$), 132.5($C_{28}$), 127.9($C_{20}$), 115.4($C_{21c}$), 84.6($C_{31}$), 81.2 ($C_{15}$), 80.4($C_{13}$), 80.3($C_{26}$), 75.0($C_{32}$), 73.6 ($C_{14}$), 72.9($C_{22}$), 70.0($C_{24}$), 59.0, 57.32, 57.27 (3×OCH$_3$), 54.7($C_{10}$), 47.1($C_{18}$), 45.1($C_{21}$), 41.2($C_{21a}$), 40.4($C_{25}$), 39.0($C_{16}$), 35.7, 35.5 ($C_{23}$, $C_{30}$), 35.47($C_{11}$), 35.1($C_{29}$), 34.7 ($C_{33}$), 34.3($C_{12}$), 31.4, 30.9($C_{2'}$,$C_{4'}$), 30.7 ($C_{34}$), 27.3($C_{17}$), 26.5($C_{3'}$), 26.0(2×SiC(CH$_3$)$_3$), 20.2($C_{17a}$), 18.7, 18.6, 18.2, 18.1, (2×Si(CH(CH$_3$)$_2$)), 18.5($C_{11a}$), 18.3 (Si$\overline{C}$(CH$_3$)$_3$), 16.6($C_{19a}$), 13.4, 12.7(2×Si($\overline{C}$H(CH$_3$)$_2$)$_3$), 11.6($C_{27a}$), 9.0($C_{25a}$), 7.0(Si(CH$_2$CH$_3$)$_3$), 5.0(Si(CH$_2$CH$_3$)$_3$), −3.6, −4.3, −4.5, −4.6(2×Si(CH$_3$)$_2$t-Bu).

EXAMPLE 10

(1R,3S,4R,5S,7S,11R,12S,14S,15R,16S,1'R,3'R,4'R-)-E,E-1-(1',3'-Dithian-2'-yl)-1,7,9,15,17-pentamethyl-3,5-dimethoxy-4,12-bis-t-butyldimethylsilyloxy-14-triisopropylsilyloxy-16-hydroxy-18-(4'-triisopropyl-silyloxy-3'-methoxycyclohex-1-yl)-octadeca-9,17-diene, 38

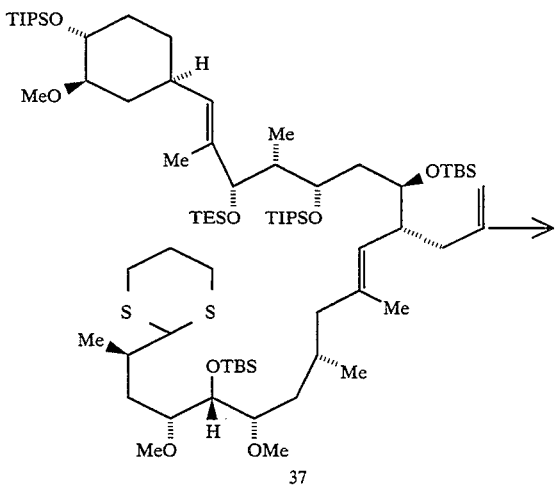

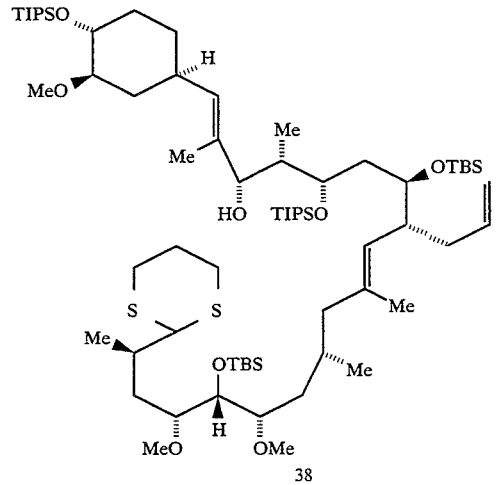

The C.10–C.34 (FK-506 numbering system) triethylsilyl ether 37 (680 mg, 0.490 mmol) was dissolved in 6.0 ml of tetrahydrofuran and 1.0 ml of water and 0.100 ml of trifluoroacetic acid was added. The mixture was stirred at 25° C. for 1.5 hr, diluted with 2.0 ml of saturated aqueous sodium bicarbonate solution, and extracted with 3×15 ml of ethyl acetate. The ethyl acetate layers were combined, dried over sodium sulfate, and concentrated in vacuo. The residual oil was chromatographed on 51 g of silica gel (eluting with hexanes:ethyl acetate; first 800 ml of 20:1 then 450 ml of 10:1) to give 578 mg of the desired secondary alcohol 38 (92.6%). The material was homogeneous by $^1$H and $^{13}$C NMR.

EXAMPLE 11

(1R,3R,4R,5S,7S,11R,12S,14S,15R,16S,1′R,3′R,4′R)-E,E-1-(1′,3′-Dithian-2′-yl)-1,7,9,15,17-pentamethyl-3,5-dimethoxy-4,12-bis-t-butyldimethylsilyloxy-11-(prop-2′-en-1′-yl)-14-triisopropylsilyloxy-16-((N-t-butylcarboyloxy-pipecolinyl)-hydroxy)-18-(4′-triisopropylsilyloxy-3′-methoxycyclohexyl)octadecan-9,17-diene, 39

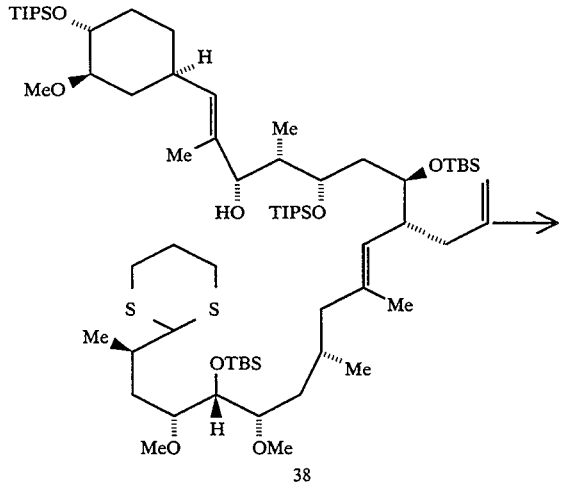

38

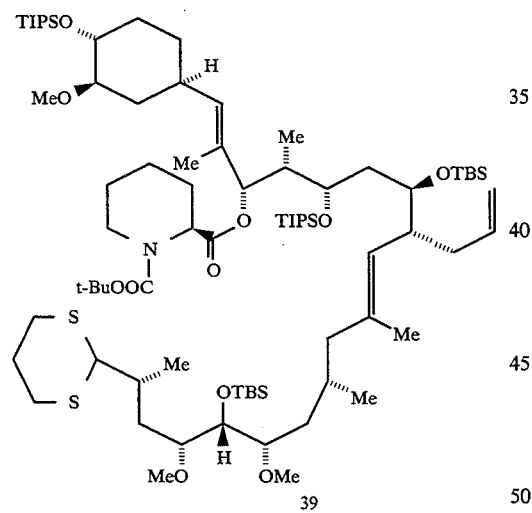

39

Alcohol 38 (578 mg), 0.454 mmol) was dissolved in 5 ml of anhydrous methylene chloride under a nitrogen atmosphere and cooled to −78° C. N-t-Boc-L-pipecolinic acid (417 mg, 1.817 mmol), dicyclohexylcarbodamide (375 mg, 1.817 mmol), and 4-dimethylaminopyridine (11 mg, 0.091 mmol) were added. The mixture was stirred at −78° C. for 5 min. then warmed to −30° C. and aged without stirring for 5 hr. and at −15° to −20° C. for 16 hr. The solids were removed by filtration and washed with 10 ml of hexanes. The filtrate was concentrated in vacuo and the resulting product was purified by chromatography on silica gel (elution with hexanes-:ethyl acetate, 8:1) to give the desired N-t-BOC-pipecolinate 39 (756 mg, 112% mass recovery). This material was used in the subsequent transformation.

EXAMPLE 12

(2R,4S,5R,6S,8S,12R,13S,15S,16R,17S,1′R,3′-R,-4′R)-E,E-1,1,4,6-Tetramethoxy-2,8,10,16,18-pentamethyl-5,13-bis-t-butyldimethylsilyloxy-12-(prop-2′-en-1′-yl)-15-triisopropylsilyloxy-17-(N-t-butyloxycarbonyl-pipecolinoyl)-19-(4′-triisopropylsilyloxy-3′-methoxycyclohex-1′-yl)-nonadeca-10,18-diene, 40

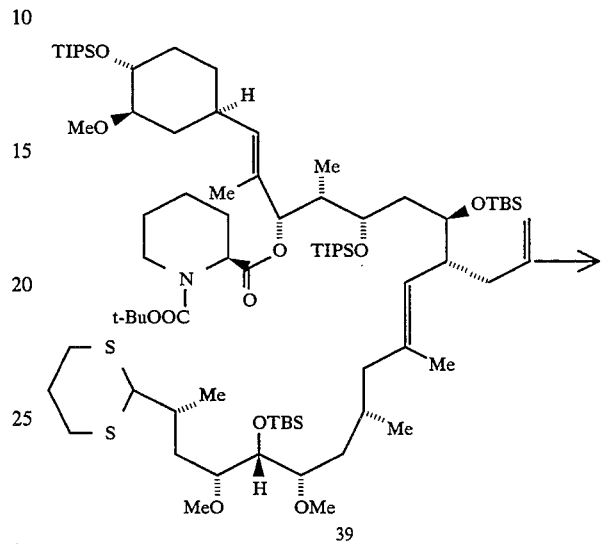

39

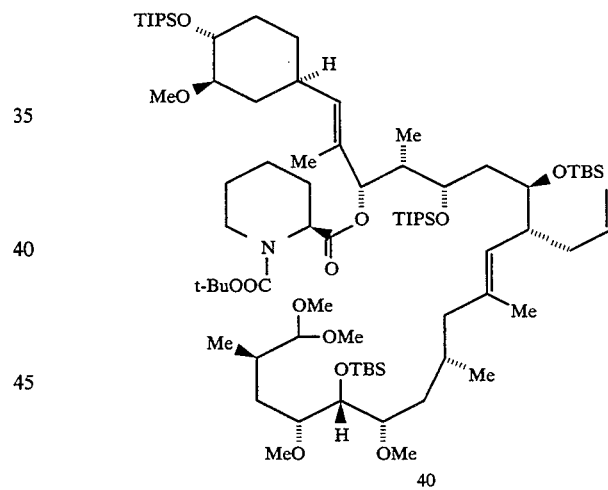

40

N-Chlorosuccinimide (229 mg, 1.712 mmmol), silver nitrate (327 mg, 1.926 mmol), and 2,2-lutidine (0.50 ml, 4.281 mmol) were dissolved in 21.2 ml of anhydrous methanol and the resulting suspension was stirred for 25 min. at 25° C. in the absence of light and under a nitrogen atmosphere. Dithiane 39 (635.1 mg, 0.428 mmol) in 10 ml of anhydrous tetrahydrofuran was added and the mixture was stirred an additional 1.5 hr at 25° C. The mixture was cooled to 0° C. and treated with 20 ml of 10% aqueous sodium bisulfite, 20 ml of saturated aqueous sodium bicarbonate solution. Water (25 ml) was added and the mixture was extracted with 4×25 ml of methylene chloride. The organic phases were combined, dried over sodium sulfate, concentrated in vacuo, and chromatographed over 30 g of silica gel (elution with 20:1, hexanes/ethyl acetate) to give the dimethyl acetal 40 (488 mg, 75% yield from 39).

EXAMPLE 13

(2R,4S,5R,6S,8S,12R,13S,15S,16R,17S,1'R, 3'R,4'R)-E,E-4,6-Dimethoxy-2,8,10,16,18-pentamethyl-5,13-bis-t-butyldimethylsilyloxy-12-(prop-2'-en-1'-yl)-15-triisopropylsilyloxy-17-((N-t-butyloxycarbonyl)-pipecolinoyl)-19-(4'-triisopropylsilyloxy-3'-methoxycyclohexyl)-nonadeca-10,18-dienal, 41

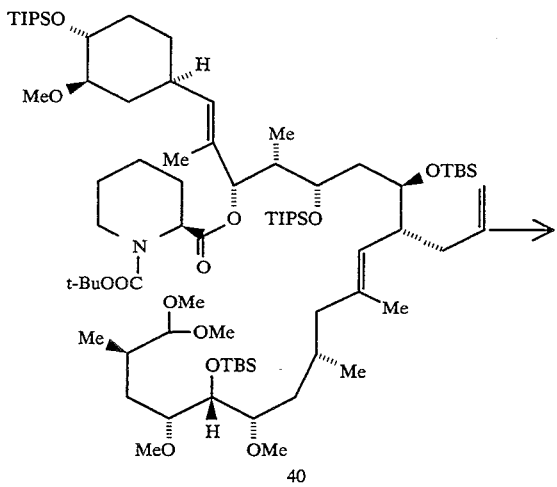

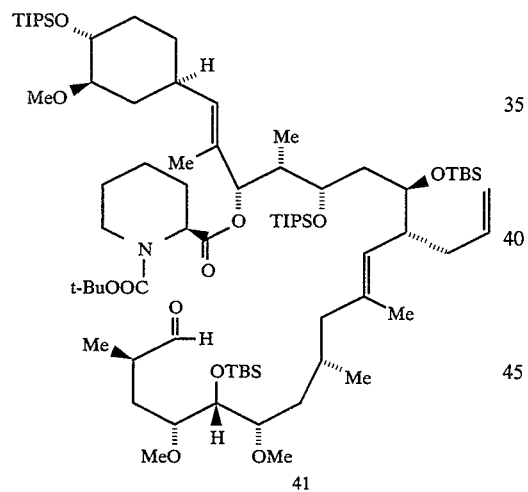

Dimethyl acetal 40 (488 mg, 0.339 mmol) was dissolved in 8 ml of methylene chloride under a nitrogen atmosphere and glyoxylic acid (312 mg, 3.39 mmol) and acetic acid (0.19 ml, 3.39 mmol) were added. The resulting solution was stirred at 40° C. for 1 hr. The reaction mixture was cooled to 25° C. and poured into 25 ml of saturated sodium bicarbonate solution at 0° C. The phases were separated and the aqueous phase was extracted with 2×25 ml of methylene chloride. The organic phases were combined, dried over sodium sulfate, and concentrated in vacuo. The resulting material was purified by chromatography on silica gel (30 g, eluting with hexanes:ethyl acetate, 12:1) to give the desired aldehyde 41 (421 mg, 89% yield). This material was homogeneous by NMR.

EXAMPLE 14

2S,3R,4R,6S,7R,8S,10S,14R,15S,17S,18R,19S,1'R,3'R,4'R)-E,E-2-(p-Methoxybenzyloxy)-3-hydroxy-4,10,12,18,20-pentamethyl-6,8,-dimethoxy-7,15-bis-t-butyldimethylsilyloxy-14-(prop-2'-en-1'-yl)-17-triisopropylsilyloxy-19-((N-t-butyloxycarbonyl)-pipecolinoyl)-21-(4'-triisopropylsilyloxy-3'-methoxycyclohexyl)-12,20-dienoic acid derived oxazolidin-2'-one imide, 42

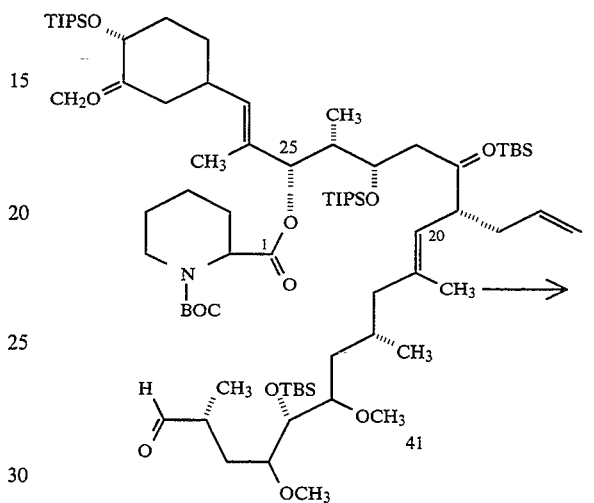

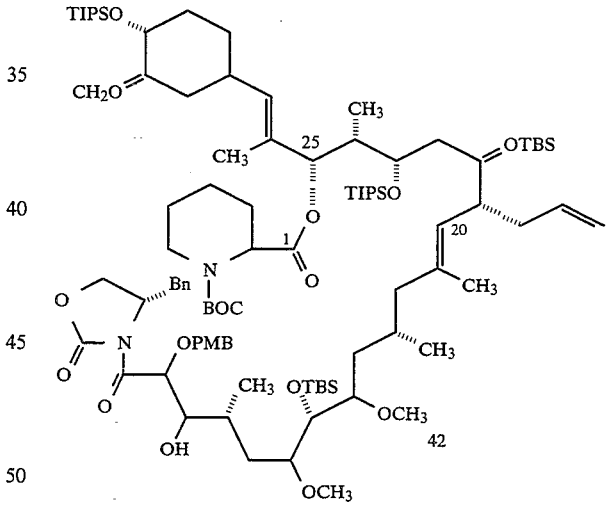

p-Methoxybenzylacetimide 15 (355 mg, 0.472 mmol) was dissolved in 1 ml of anhydrous toluene at −50° C. under a nitrogen atmosphere. Triethylamine (0.85 ml, 0.609 mmol) and dibutylboron triflate (0.114 ml, 0.456 mmol) were added and the mixture was stirred for 1.5 hr. Aldehyde 41 (424 mg, 0.304 mmol) in 1.0 ml of toluene was add ed and the mixture was warmed to −30° C. and aged for 16 hr. The reaction was quenched by the addition of 0.5 ml of pH 7.0 phosphate buffer solution, 1.0 ml of methanol, and 2.0 ml of tetrahydrofuran. The mixture was stirred at 0° C. for 30 min. and 0.5 ml of 30% aqueous hydrogen peroxide solution was added. The mixture was stirred 1 hr at 0° C., 10 ml of saturated sodium chloride solution was added, and the mixture was extracted with 3×20 ml of ethyl acetate. The organic phases were combined, dried over sodium sulfate, and concentrated in vacuo. Chromatography on silica gel (elution with 3:1 hexanes:ethyl acetate) gave 468 mg of the desired aldol adduct 42 (88% yield). The aldol adduct was homogeneous by NMR.

EXAMPLE 15

(2S,3R,6S,7R,8S,10S,14R,15S,17S,18R,19S,1'R-,3'R,4'R)-E,E-2-(4'-Methoxybenzyloxy)-3-triethylsilyloxy-9,12,18,20-pentamethyl-6,8-dimethoxy-7,15-bis-t-butyldimethylsilyloxy-14-(prop-2'-en-1'yl)-17-triisopropylsilyloxy-19-pipecolinoyl-21-(4'-triisopropylsilyloxy-3'-methoxycycloxhexyl)-12,20 dienoic acid, 43

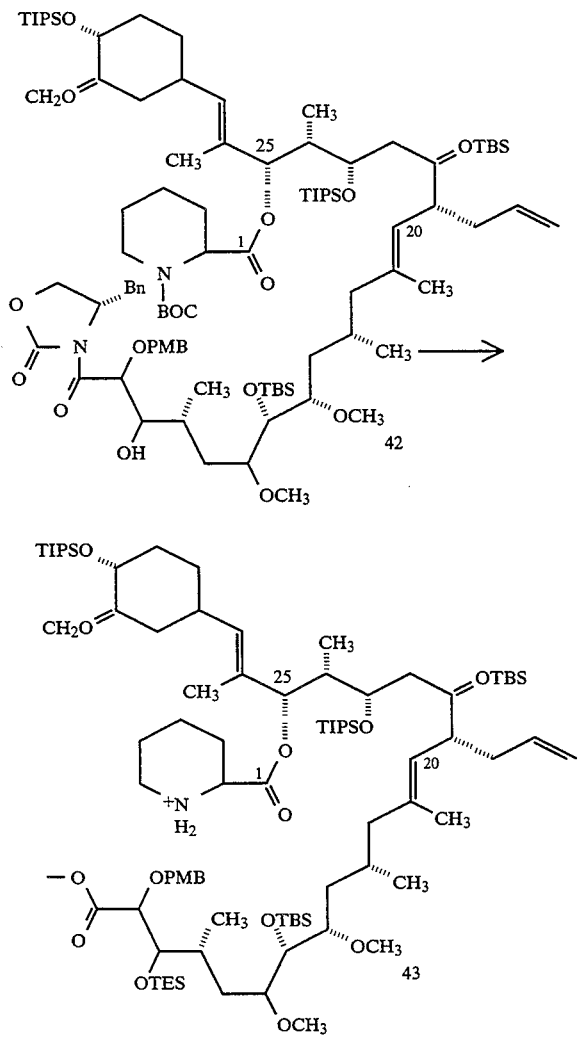

Alcohol 42 (100 mg, 0.057 mmol) was dissolved in 0.96 ml of tetrahydrofuran and 0.24 ml of water was added. The mixture was cooled to 0° C. under a nitrogen atmosphere, and hydrogen peroxide (0.047 ml of a 30% aqueous solution, 0.46 mmol) and lithium hydroxide (4.8 mg, 0.114 mmol) were added. The mixture was stirred at 0° C. for 1.5 hr and then concentrated in vacuo to remove tetrahydrofuran. Hexanes (2.0 ml) and water (0.6 ml) were added and the mixture was cooled to 0° C. The pH was adjusted to 4.0–4.5 with 0.5M aqueous sodium bisulfate. The phases were separated and the aqueous phase was extracted with 4×3 ml of hexanes. The combined organic layers were dried over sodium sulfate and concentrated in vacuo to give 95.9 mg of an oil. This oil (0.057 mmol) was dissolved in 0.9 ml of anhydrous methylene chloride under nitrogen and cooled to −12° C. 2,6-Lutidine (37 mg, 0.34 mmol, 6 equiv) was added followed by triethylsilyltriflate (0.058 ml, 0.26 mmol, 4.5 equiv). The solution was warmed to 0° C. over a 20 min. period and the mixture was stirred at 0° C. for 1.25 hr. Water (0.6 ml) was added and the mixture was stirred vigorously for 30 sec. Hexanes (2.0 ml) was added and the phases were separated. The aqueous phase was extracted with an additional 4×3 ml of hexanes, the organic phases were combined, dried over sodium sulfate, applied to a 14 g silica gel flash chromatography column with methylene chloride and aged on the column for 65 min. The column was eluted periodically with solvent to insure exposure of the material to fresh silica gel. Complete elution of the column with 125 ml of methylene chloride followed by 150 ml of methylene chloride containing 1% methanol, 120 ml of 4% methanol/methylene chloride, and 200 ml of 8% methanol/methylene chloride gave 72.2 mg of the amino acid 43 (76% yield). The material was homogeneous by NMR.

$^1$H NMR: δ 7.28(m, H$_{2',6'}$) 6.83(m, H$_{3',5'}$), 5.68(m, H$_{21b}$), 5.50(br, actives), 5.45(d,J=9.8, (H$_{26}$), 5.39(d,J=8.8, H$_{28}$), 4.95(m, H$_{21c}$), 4.74 (d,J=10.3, H$_{20}$), 4.65, 4.24(2×d,J=11.2, OCH$_2$Ar), 3.93(t,J=4.0, H$_{10}$), 3.88(m, H$_{24}$), 3.81(d, J=4.0, H$_9$), 3.78(s, ArOCH$_3$), 3.76(br d,J=6.8, H$_{14}$), 3.64(m, H$_2$), 3.55(m, H$_{32}$), 3.44, 3.38, 3.29(3×OCH$_3$), 3.20(m, H$_{22}$), 3.17(obs d,H$_{6eq}$), 3.08(br t,J=6.5,H$_{15}$), 3.02(m, H$_{13}$), 2.97(m, H$_{31}$), 2.77 (br t,J=11,H$_{6ax}$), 1.65(br s,C$_{27a}$H$_3$), 1.58(br s ,C$_{19a}$H$_3$).

$^{13}$C NMR: δC 175.0(C$_8$), 171.2 (C$_1$), 159.1(C$_{4'}$), 137.6(C$_{21b}$), 136.4(C$_{28}$), 136.0, 130.6, 130.0(C$_{19}$, C$_{27}$, C$_{1'}$), 129.9 (C$_{2',6'}$), 128.3(C$_{20}$), 115.4(C$_{21c}$), 113.5 (C$_{3',5'}$), 84.4(C$_{31}$), 82.5, 81.9, 76.5, 75.8, (C$_9$, C$_{10}$, C$_{14}$, C$_{26}$), 81.1(C$_{15}$), 80.4 (C$_{13}$), 74.8(C$_{32}$), 72.9(C$_{22}$), 72.2(OCH$_2$Ar), 69.5(C$_{24}$), 59.7(ArOCH$_3$), 57.5, 56.8, 56.5(3×OCH$_3$), 55.1(C$_2$), 47.2(C$_{18}$), 46.6(C$_{21}$), 43.6, 42.1(C$_6$, C$_{16}$), 40.4(C$_{21a}$), 38.2(C$_{25}$), 36.4(C$_{23}$), 35.8(C$_{30}$,C$_{11}$), 35.1(C$_{29}$), 34.0(C$_{33}$), 32.1(C$_{12}$), 30.2(C$_{34}$), 28.4, 24.9, 23.2 (C$_3$, C$_4$, C$_5$), 27.3(C$_{17}$), 26.0(SiC(CH$_3$)$_3$), 20.1(C$_{17a}$), 18.54, 18.50, 18.09, 18.08(2×Si(CH(CH$_3$)$_2$)$_3$), 18.2(SiC(CH$_3$)$_3$), 17.4, 16.5 (C$_{11a}$,C$_{19a}$), 13.2, 12.6(2×Si(CH(CH$_3$)$_2$)$_3$), 12.2(C$_{27a}$), 8.6 (C$_{25a}$), 7.0, 6.9(2×Si(CH$_2$CH$_3$)$_3$), 5.1, 5.0(2×Si(CH$_2$CH$_3$)$_3$), −3.0, −4.2 (Si(CH$_3$)$_2$).

EXAMPLE 16

C.9-(p-Methoxybenzyloxy)-C.10-triethylsilyloxy-C.14,C.22-bis-t-butyldimethylsilyloxy-C.24,C.32-bis(-triisopropylsilyloxy)-hexahydro-FK-506, 44 (FK-506 numbering system)

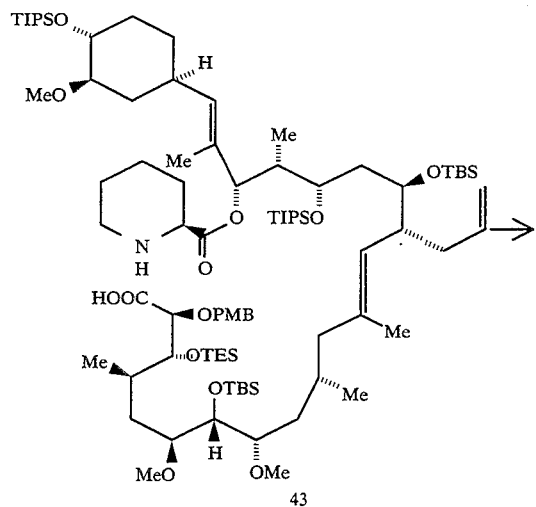

43

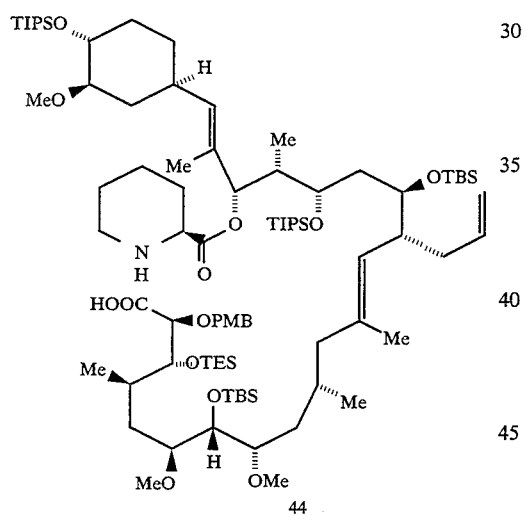

44

N-Methyl 2-pyridinium iodide (13.4 mg, 0.052 mmol) was dissolved in 30 ml of methylene chloride under a nitrogen atmosphere and 0.010 ml of triethylamine was added. Amino acid 43 (70 mg, 0.044 mmol) in 9.0 ml of methylene chloride containing 0.020 ml of triethylamine was added via syringe over a period of 1.5 hr at 25° C. The mixture was stirred an additional 1-2 hr at 25° C., 2.0 ml of water was added, and the methylene chloride was removed in vacuo. The mixture was extracted with hexanes (4×6 ml), the fractions were combined, dried over sodium sulfate, and concentrated in vacuo to give 65.5 mg of an oil. The oil was purified by flash chromatography on silica gel (eluting with 125 ml of 30:1 hexanes/ethyl acetate followed by 120 ml of 15:1 hexanes/ethyl acetate) to give 53.2 mg of macrocycle 44 (77%). This material was homogeneous by $^1$H and $^{13}$C NMR.

EXAMPLE 17

C.9,C.10-Dihydroxy-C.14,C.22-bis-t-butyldimethylsilyloxy-C.24,C.32-bis-triisopropylsilyloxy FK-506, 46

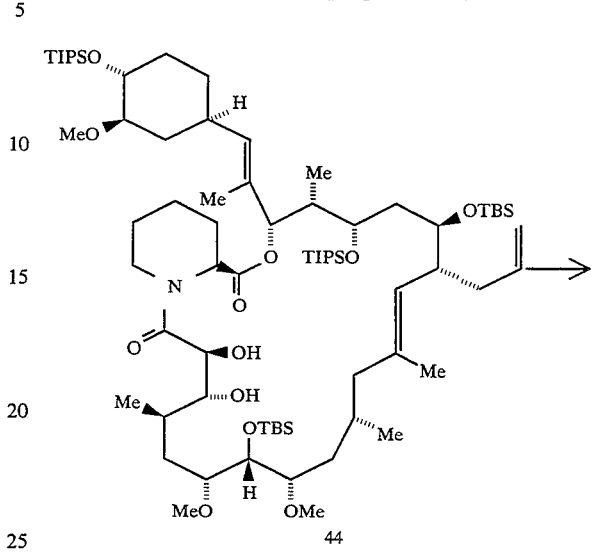

44

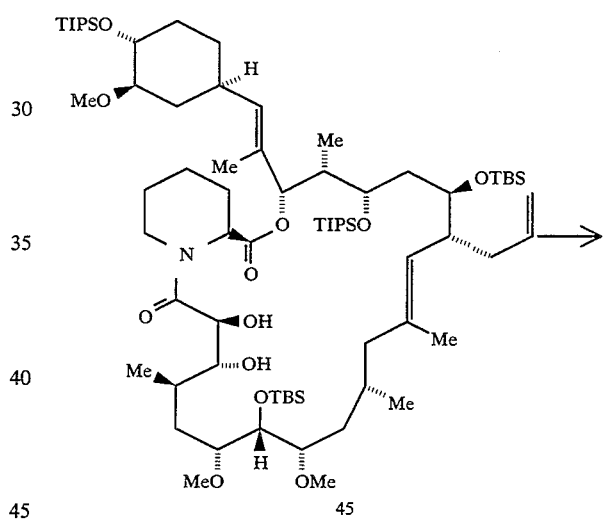

45

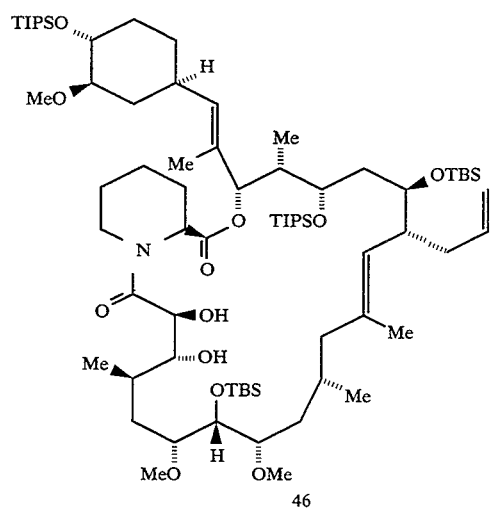

46

Macrocycle 44 (148 mg, 0.093 mmol) was dissolved in 0.8 ml of methylene chloride and 0.044 ml of water and the mixture was stirred at 25° C. 2,3-Dichloro-5,6-dicyano-1,4-benzoquinone (106 mg, 0.47 mmol) was added and the resulting mixture was stirred at 25° C. for ca 4 hr. The crude reaction mixture was then chromatographed on 13 g of flash chromatography silica gel (eluting with 130 ml methylene chloride; 250 ml of 15:1 hexanes:ethyl acetate; 230 ml 6:1 hexanes/ethyl acetate; and 200 ml of 3:1 hexanes/ethyl acetate) to give 73 mg of the C.9-hydroxy-C.10-triethylsilyloxy compound 45 (53.3%) and 31 mg of the C.9-C.10-dihydroxy macrocycle 46. The C.9 hydroxy-C.10-triethylsilyloxy compound 45 was dissolved in 1.5 ml of tetrahydrofuran and 0.050 ml of trifluoroacetic acid was added. The mixture was stirred at 25° C. for 3.5 hr. The mixture was diluted with 3 ml of saturated aqueous sodium bicarbonate solution and extracted with 4×3 ml of ethyl acetate. The combined organic phases were dried over sodium sulfate, concentrated in vacuo, and chromatographed on silica gel (elution with 3:1 hexanes/ethyl acetate) to give 61.2 mg of diol 46. This material was combined with the diol obtained from the chromatography above to give 91 mg of diol (72% overall yield for the removal of the C.9-p-methoxybenzyl and C.10-triethylsilyloxy protecting groups).

Selected data for 45 $^1$H NMR (major rotamer): δ 5.67(m, $H_{21b}$), 5.53(d,J=10.7,$H_{26}$), 5.42(d,J=8.8,$H_{28}$), 5.10(br d,J=4.9,$H_2$), 4.93(m, $H_{21c}$), 4.72(d,J=10.3,$H_{20}$), 4.51(br d,J=12.7,$H_{6eq}$), 4.24(d,J=9.3,$H_{10}$), 4.15 (d,J=9.8,$H_9$), 3.95(m,$H_{24}$), 3.70(d,J=8.3,$H_{14}$), 3.54 (d,J=9.8,10-OH), 3.51, 3.37, 3.25 (3×s, 3×OCH$_3$), 3.25(obs m,$H_{6ax}$), 1.69(d,J=1.0,$C_{27a}H_3$), 1.58(br s,$C_{19a}H_3$). Additional data: NOE difference spectroscopy showed a 5% NOE from $H_9$ to $H_2$ providing firm evidence for cyclization.

EXAMPLE 18

C.14,C.22-bis-t-butyldimethylsilyloxy-C.24,C.32-bis-triisoprooylsilyloxy-FK-506, 47

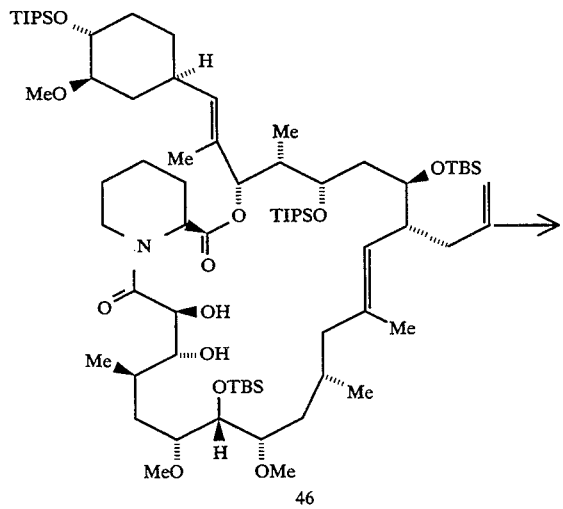

46

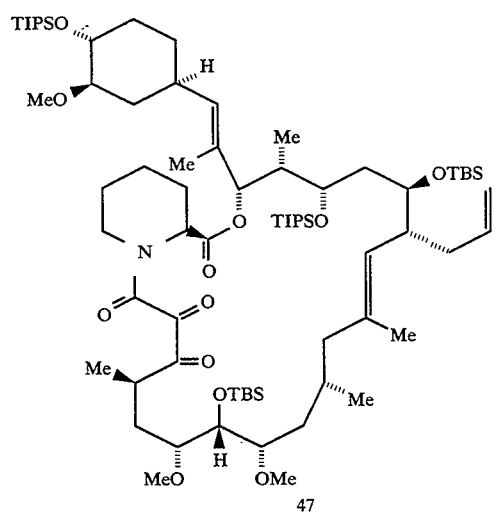

47

Oxalyl chloride (0.0061 ml, 0.07 mmol) was dissolved in 0.5 ml of methylene chloride and cooled to −78° C. under a nitrogen atmosphere. Dimethyl sulfoxide (0.0071 ml, 0.100 mmol) was added and the mixture was stirred for 20 min. The dihydroxy macrocycle 46 (27 mg, 0.01996 mmmol) dissolved in 0.5 ml of methylene chloride was added to the oxidant solution and the mixture was stirred at −78° C. for 3 hr. Triethylamine (0.019 ml, 0.14 mmol) was added and the mixture was warmed to −30° C. and stirred for 1 hr. The reaction was quenched by the addition of 10 ml of 0.5M sodium bisulfate solution and the mixture was extracted with 3×10 ml of ethyl acetate. The ethyl acetate phases were combined, dried over sodium sulfate, concentrated in vacuo, and purified by chromatography on silica gel (eluting with 6:1 hexanes/ethyl acetate. Repetition of the preceding procedure gave 13 mg of the desired diketo compound 47. Starting dihydroxide compound 46 (11 mg) was also recovered. The diketo-macrocycle 47 was homogeneous by both $^1$H and $^{13}$C NMR.

Selected data for 47. $^1$H NMR (major rotamer): δ 5.70(m, $H_{21b}$), 5.44(d,J=8.3,$H_{28}$), 5.26(d,J=9.8,$H_{26}$), 5.21(br d,J=3.9,$H_2$), 4.94(m, $H_{21c}$), 4.87(obs d,$H_{20}$), 3.89(m, $H_{24}$), 3.74(dd, J=5.4,3.4,$H_{14}$), 3.54(m, $H_{32}$), 3.40, 3.37, 3.20(3×s, 3×OCH$_3$), 3.40(obs m,$H_{11}$), 3.4–3.0(obs m, $C_6H_2$), 2.95(m, $H_{31}$), 1.59(br s,$C_{19a}H_3$), 1.18(d,J=6.8,$C_{11a}H_3$), 0.86(d,J=6.8,$C_{17a}H_3$), 0.85 (d,J=6.4,$C_{25a}H_3$).

$^{13}$C NMR(75.47 MHz, major rotamer of the tricarbonyl moiety): $δ_C$199.2 ($C_{10}$), 185.9 ($C_9$), 165.5 ($C_8$).

EXAMPLE 19

C.22-Dihydro-FK-506, 48

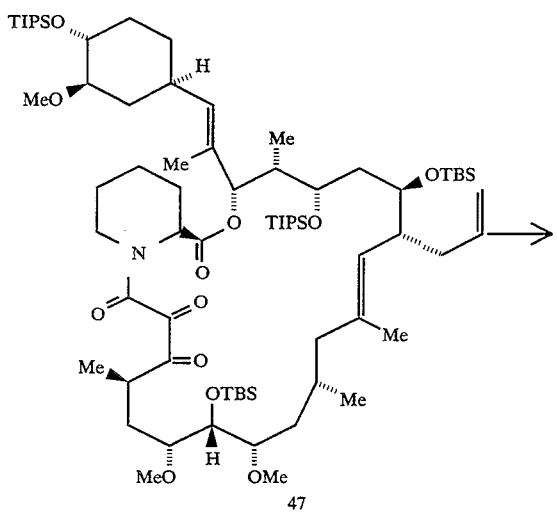

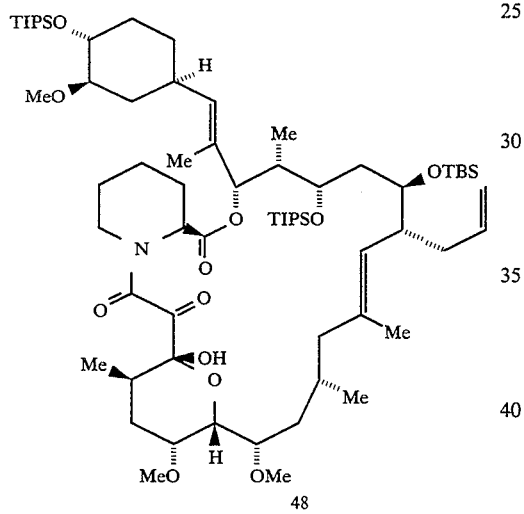

Diketo-macrocycle 47 (9.3 mg, 0.0097 mmol) was dissolved in 1.0 ml of anhydrous acetonitrile at 0° C. and 2 drops of 48% hydrofluoric acid was added. The mixture was stirred for 6.5 hr at 0° C. and the reaction mixture was quenched with 2 ml of saturated aqueous sodium bicarbonate solution. The mixture was extracted with 3×5 ml of ethyl acetate. The organic phases were combined, dried over sodium sulfate, concentrated in vacuo, and chromatographed 4n silica gel eluting with 1:2 hexanes/ethyl acetate to give 4.6 mg of tetraol 48 as an oil (60% yield). This material was homogeneous by $^1$H NMR.

Data are reported for the major amide rotamer (amide carbonyl syn to the 6-CH$_2$ as evidenced by the large non-equivalence of the geminal protons; rotamer ratio 85/15). $^1$H NMR: δ 5.75(H$_{21b}$,m), 5.54(br d,J=2.4,H$_{26}$), 5.30 (d,J=2.0,10-OH), 5.04(obs d,H$_{28}$), 4.97(m,H$_{21c}$), 4.92(obs d,H$_{20}$), 4.42(obs br d,H$_{6eq}$), 4.38(t, J=3.9,H$_2$), 3.93(m,H$_{24}$), 3.85 (m, H$_{22}$) 3.42(s, OCH$_3$), 3.40(obs m,H$_{32}$), 3.38 (s, OCH$_3$), 3.30(s, OCH$_3$), 3.28(br s, OH), 3.03 (m, H$_{31}$), 2.96(td, J=13.2,2.9), 2.87(br s, OH), 2.68 (m, H$_{21}$), 2.67 (br s, OH), 2.44(m, H$_{11}$), 1.66 (br s, C$_{27a}$H$_3$), 1.60(br s, C$_{19a}$H$_3$), 1.02 (d, J=6.8,C$_{17a}$H$_3$), 0.91(d, J=6.8,C$_{11a}$H$_3$), 0.82 (d,J=7.3,C$_{25a}$H$_3$). Protons H$_{13}$, H$_{14}$, and H$_{15}$, were essentially degenerate in CDCl$_3$ at 3.4 ppm. Proton 1-D and 2-D NMR in C$_6$D$_6$ provides the following selected data (250.13 MHz, C$_6$,D$_6$, δ=7.12): δ 3.73 (d,J=9.8,H$_{14}$), 3.60(br d,J=9.8,H$_{15}$), 3.44(obs m, H$_{13}$).

$^{13}$C NMR (62.9 MHz): δ$_C$198.6(C$_9$), 169.1(C$_1$), 165.7(C$_8$), 136.8(C$_{21b}$), 136.3 (C$_{19}$), 132.7(C$_{27}$), 128.3 (C$_{28}$), 125.4(C$_{20}$), 115.9(C$_{21c}$), 98.6(C$_{10}$), 84.3(C$_{31}$), 76.1, 74.2, 73.7(C$_{13}$,C$_{14}$,C$_{15}$), 75.8(C$_{26}$), 74.9(C$_{22}$), 74.1(C$_{24}$), 73.6(C$_{32}$), 57.0(C$_2$), 56.6, 56.4, 56.3 (3×OCH$_3$), 49.1 (C$_{18}$), 43.3(C$_{21}$), 39.2(C$_{25}$), 39.0(C$_6$), 37.8 (C$_{23}$), 35.0, 34.7(C$_{21a}$), (C$_{30}$), 34.9, 34.8 (C$_{11}$,C$_{29}$), 32.9 (C$_{16}$), 32.6(C$_{12}$), 31.3 (C$_{33}$), 30.8(C$_{34}$), 27.6(C$_{17}$), 27.0(C$_3$) 24.3 (C$_5$), 21.7(C$_4$), 21.6(C$_{17a}$), 16.0(C$_{19a}$), 15.7 (C$_{11a}$), 14.6(C$_{27a}$), 10.4(C$_{25a}$).

EXAMPLE 20

C.24,C.32-Bis-TES-C.22-dihydro FK-506, 49

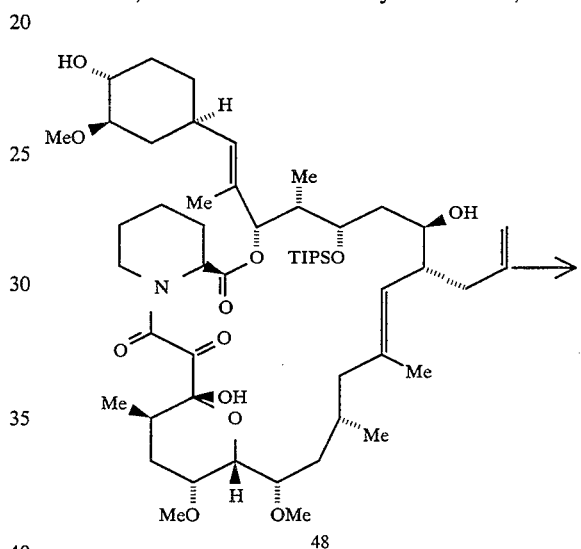

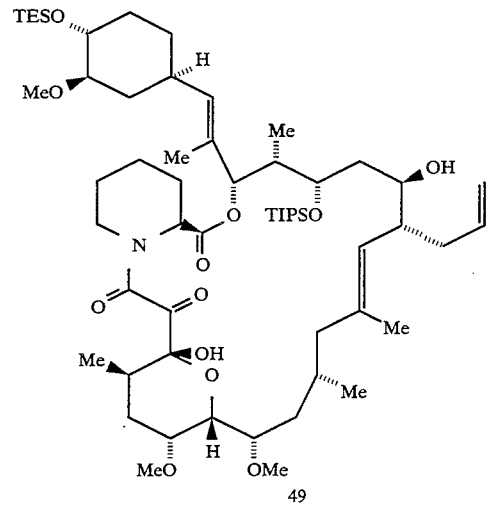

Dihydro-FK-506 48 (10.1 mg, 0.0125 mmol) was dissolved in 0.5 ml of anhydrous pyridine at 0° C. under a nitrogen atmosphere and triethylsilyl chloride (0.0053 ml, 0.031 mmol) was added. The mixture was stirred for 12 hr at 0° C. and the mixture was quenched by the addition of 5 ml of saturated aqueous sodium bisulfate solution. The mixture was extracted with 3×5 ml of ethyl acetate, the organic phases were combined, dried over sodium sulfate, and concentrated in vacuo. Chromatography of the residual oil on silica gel (elution with 3:1 hexanes/ethyl acetate) gave 9.0 mg of bis-TES-C.22-dihydro-FK-506 49. The material was homogeneous by NMR.

EXAMPLE 21

C.24,C.32-Bis-triethylsilyloxy-FK-506, 50

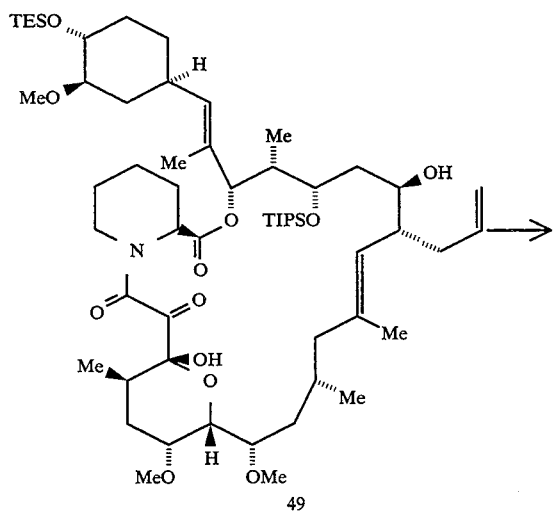

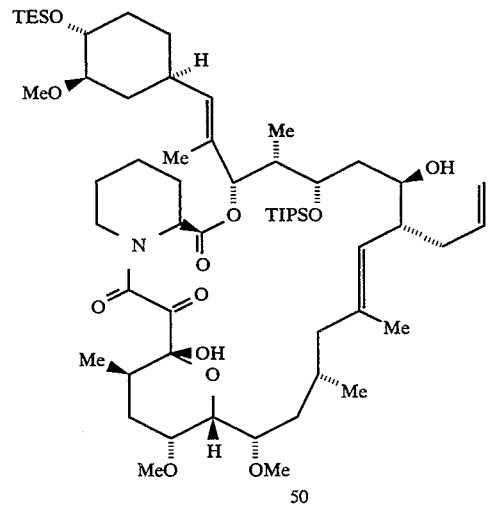

Dihydro compound 49 (1.5 mg, 0.0013 mmol) was dissolved in 0.6 ml of methylene chloride under a nitrogen atmosphere. Dess-Martin periodinane (J. Org. Chem. 48, 4155, 1983) was added and the mixture was stirred at 25° C. for 45 min. The reaction mixture was chromatographed on silica gel (elution with hexanes:-methylene chloride:acetonitrile/60:36:4) to give 0.9 mg of 24,C.32-Bis-TES-FK-506 50 (60% yield).

EXAMPLE 22

FK-506 (1)

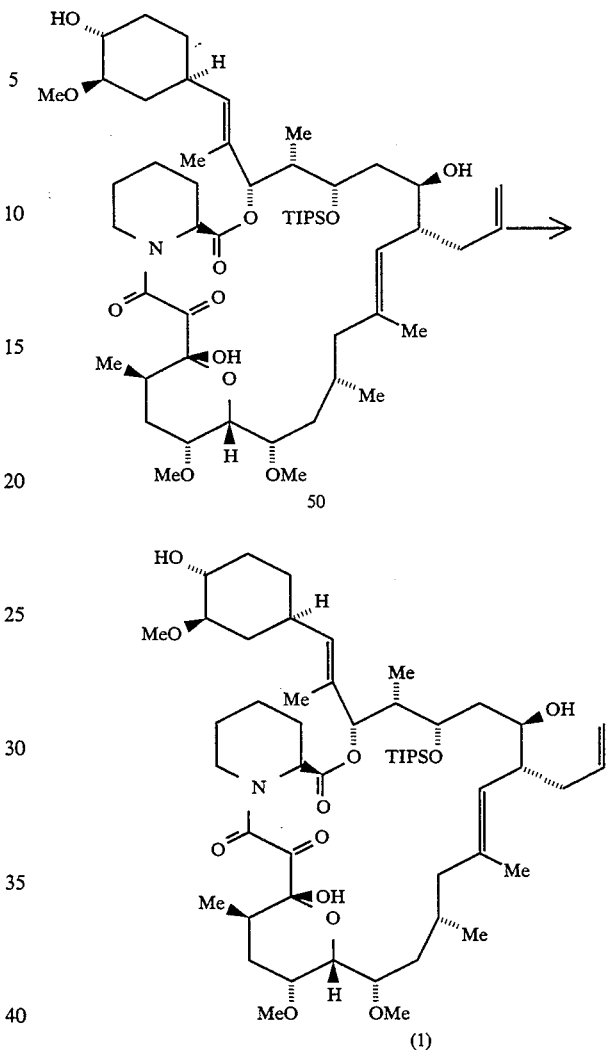

Bis-TES-FK-506 50 (53 mg, 0.048 mmmol) was dissolved in 1 ml of acetonitrile at 25° C. and 4 drops of aqueous 48% hydrofluoric acid was added. The mixture was stirred for 5 min and was quenched by the addition of 1 ml of aqueous sodium bicarbonate solution. The solution was extracted with 5×5 ml of ethyl acetate. The combined organic phases were dried over sodium sulfate, concentrated in vacuo, and chromatographed on silica gel (6 g, elution with 150 ml 2:1 methylene chloride:acetonitrile, 100 ml 1:1 methylene chloride:acetonitrile) to give 26 mg of FK-506 (1). This material was homogeneous by NMR.

EXAMPLE 23

C.9,C.10,C.22-Hexahydro-FK-506 51

Macrocycle 46 (9.0 mg) was dissolved in 0.5 ml of an 85/15/5 mixture of acetonitrile/concentrated aqueous HF/water. After stirring for 12 hr at room temperature, 2 ml of saturated aqueous sodium bicarbonate was added. The mixture was extracted with ethyl acetate (3×5 ml). The organic layers were combined, dried over sodium sulfate, filtered, concentrated and chromatographed (9:1 CH2Cl2/methanol) to provide 1.5 mg of hexaol 51.

EXAMPLE 24

(2R,4S,5R,6S,8S,12R,13S,15S,16R,17S,1′R,3′R,4′R)-E,E-2,8,10,16,18-Pentamethyl-1,1,4,6-tetramethoxy-5,13-bis-t-butyldimethylsilyloxy-12-(prop-2′-en-1′yl)-15-triisopropylsilyloxy-17-hydroxy-19-(4′-triisopropylsilyloxy-3′-methoxycyclohexyl)-nonadecan-10,18-diene, 52

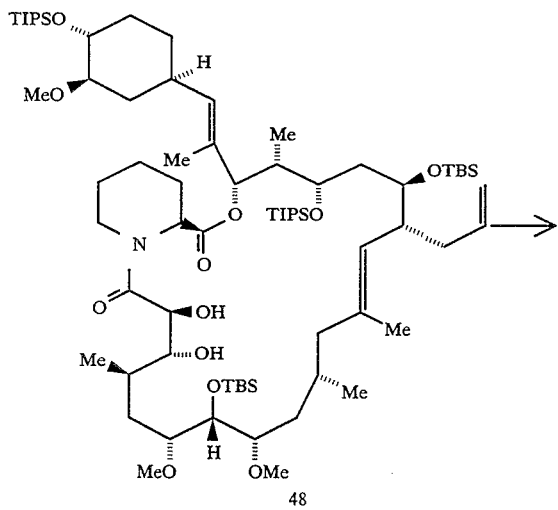

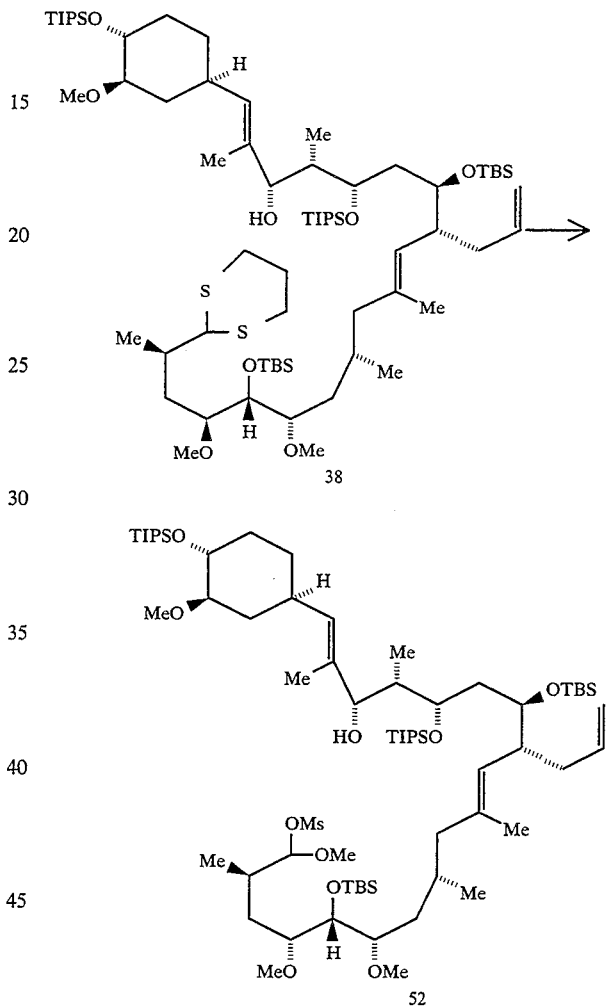

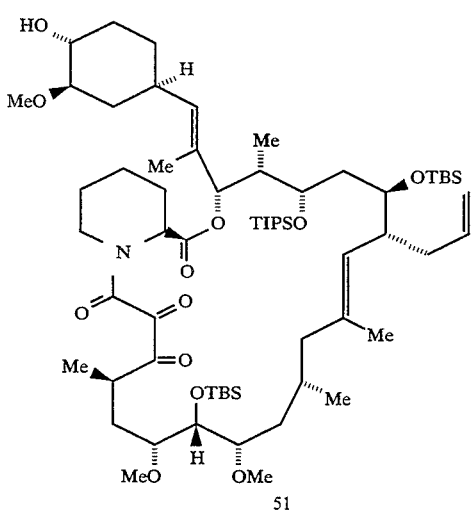

N-Chlorosuccinimide (460 mg 3.4 mmmol), silver nitrate (050 mg, 3.9 mmol), and 2,6-lutidine (1.0 ml, 8.4 mmol) were mixed with 42 ml of anhydrous methanol and the resulting suspension was stirred at 25° C. for 25 minutes in the absence of light under a nitrogen atmosphere. Dithiane 38 (0.8 mmol) in 20 ml of anhydrous tetrahydrofuran was added and the mixture was stirred an additional 1.5 hr at 25° C. The mixture was cooled to 0° C. and treated with 40 ml of 10% aqueous sodium bicarbonate solution. Water (50 ml) was added and the mixture was extracted with 4×50 ml of methylene chloride. The organic phases were combined, dried over sodium sulfate, concentrated in vacuo and chromatographed over 50 g of silica gel (elution with 20:1 hexanes:ethylacetate) to give the dimethyl acetal 52 (735 mg, 75%).

EXAMPLE 25

(2R,4S,5R,6S,8S,12R,13S,16R,17S,1'R,-3'R,4'R)--E,E-2,8,10,16,18-Pentamethyl-1,1,4,6-tetra-methoxy-5,13-bis-t-butyldimethylsilyloxy-2-(prop-2'-en-1'-yl)-15-triisopropylsilyloxy-17-hydroxy-19-(4'-triisopropylsilyloxy-3'-methoxycyclohexyl)-nonadecan-10,18-diene 53

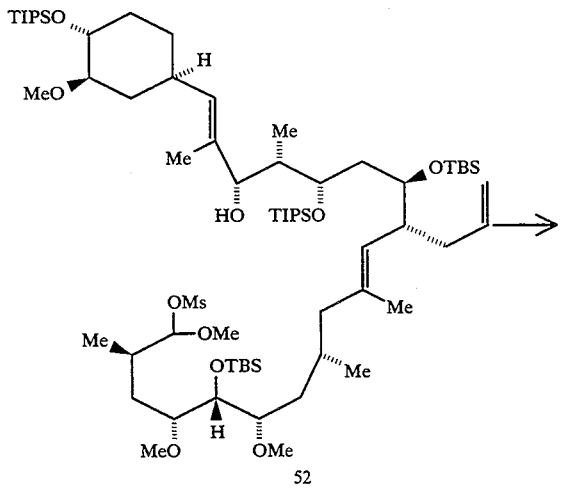

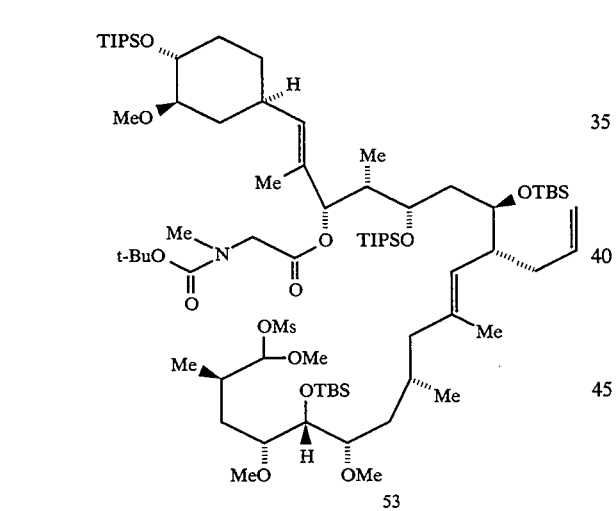

Alcohol 52 (629.6 mg, 0.505 mmmol) was dissolved in 3.3 ml of anhydrous methylene chloride under a nitrogen atmosphere and cooled to −50° C. N-t-Boc-methylglycine (382 mg, 2.02 mmol) dicyclohexylcarbodiimide (417 mg, 2.02 mmol) and 4-dimethylaminopyridine 417 mg, 0.2 equiv) were added. The mixture was stirred at −50=C for 10 minutes and then warmed to −20° C. and aged for 16 hours without stirring. The mixture was filtered and the solids were washed with 10 ml of hexanes. The combined filtrates were concentrated in vacuo and the resulting product was purified by chromatography on silica gel (elution with hexanes:ethyl acetate, 6:1) give the desired N-t-boc-glycine derivative 53 (697 mg 98.7% yield). This material was used in the subsequent transformation.

EXAMPLE 26

(2R,4S,5R,6S,8S,12R,13S,15S,16R,17S,1'R,3'R,4'R)--E,E-4,6,dimethoxy-2,8,10,16,18-pentamethyl-5,13,-bis-t-butyldimethylsilyloxy-12-(prop-2'-en-1'-yl)-15-triisopropylsilyloxy-17-((N-t-butyloxycarbonyl-N-methylglycinoyl)-19-(4'-triisopropylsilyloxy-3'-methoxycyclohexyl)-nonadeca-10,18-dienal, 54

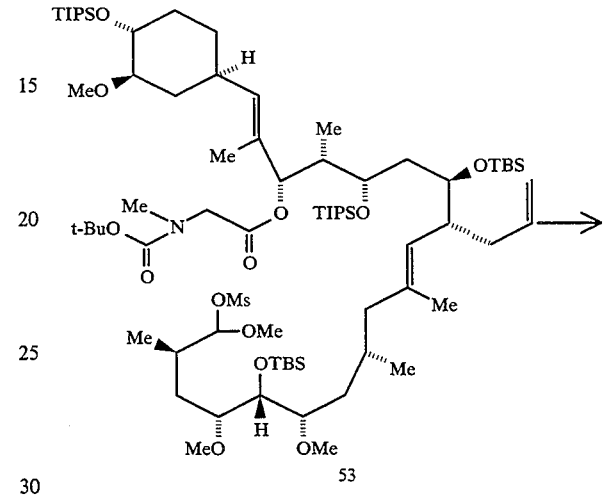

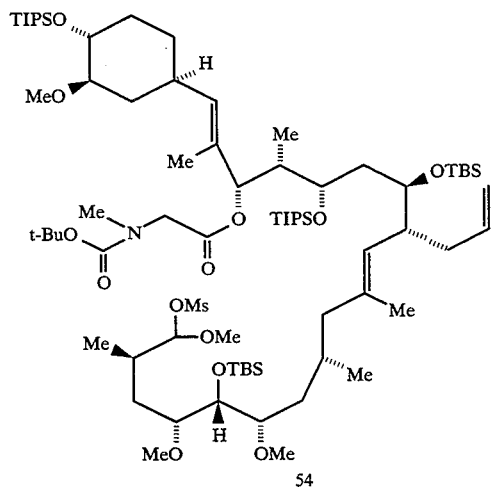

Dimethyl acetal 53 (681 mg, 0.487 mmol) was dissolved in 21 ml of methylene chloride under a nitrogen atmosphere and glyoxylic acid monohydrate (448 mg, 4.87 mmol) and acetic acid (279 microliters, 10.0 equiv) were added. The resulting solution was stirred at 40° C. for 2.5 hr. The mixture was cooled to 25° C. and poured into 25 ml of saturated sodium bicarbonate solution at 0° C. The phases were separated and the aqueous phase was extracted with 2×25 ml of methylene chloride. The organic phases were combined, dried over sodium sulfate, and concentrated in vacuo. The resulting material was purified by column chromatography on 50 g of silica gel eluting with hexanes:ethyl acetate (7:1) to give the desired aldehyde 54 (653 mg, 99.2%). The material was homogeneous by NMR.

EXAMPLE 27

(2S,3R,4R,6S,7R,8S,10S,14R,15S,17S,18R,19S,1′R,3′R,4′R)-E,E-2-(p-Methoxybenzyloxy)-3-hydroxy-4,10,12,18,20-pentamethyl-6,8,-dimethoxy-7,15,-bis-t-butyldimethylsilyloxy-14-(prop-2′-en-1′-yl)-17-triisopropylsilyloxy-19-((N-t-butyloxycarbonyl-N-methylglycinoyl)-21-(4′-triisopropylsilyloxy-3′-methoxycyclohexyl)-12,20-dienoic acid derived oxazolidin-2′-one imide 55

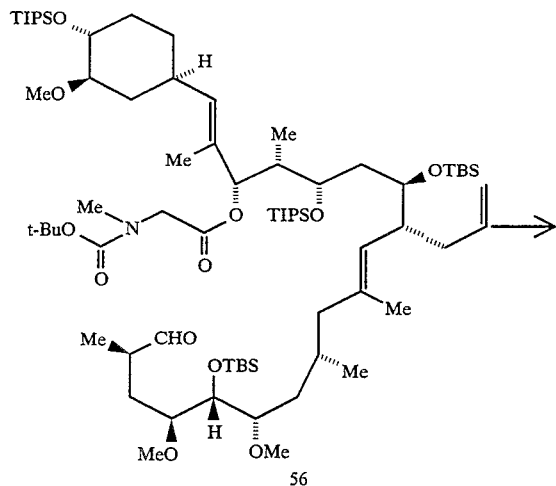

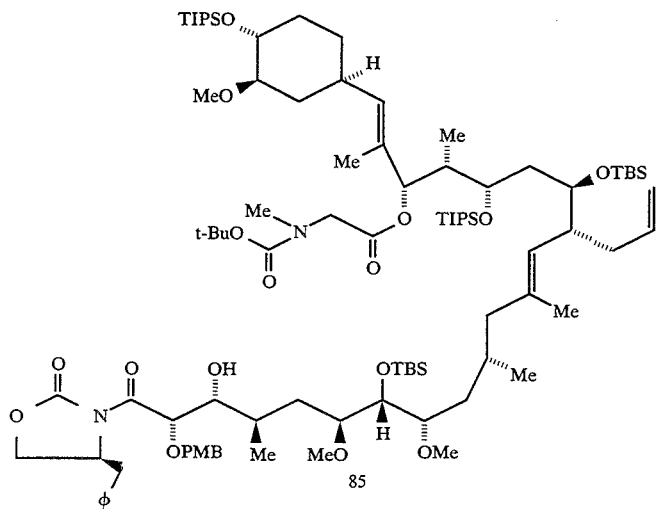

p-Methoxybenzylacetimide 15 (488.5 mg, 1.37 mmol) was dissolved in 6.3 ml of anhydrous toluene at −50° C. under a nitrogen atmosphere. Triethylamine (0.255 ml, 4.0 equiv) and dibutylboron triflate (0.332 ml, 2.9 equiv) were added and the mixture was stirred for 1.5 hr. Aldehyde 54 (611 mg .0.451 mmmol) in 1.0 ml of toluene was added and the mixture was stirred for 1.0 hr at −50° C. The mixture was warmed to −30° C. and stirred for an additional 1.5 hr. Tlc analysis (3:1, hexanes:ethyl acetate) showed the reaction to be complete at this time. The reaction mixture was quenched by the addition of 8.0 ml of saturated sodium bicarbonate solution and then partitioned between 40 ml of aqueous sodium bicarbonate solutions and 75 ml of ethyl acetate. The layers were separated and the aqueous phase was extracted with 2×75 ml of ethyl acetate. The combined organic layers were washed with 20 ml of saturated sodium chloride solution and dried over sodium sulfate.

Concentration in vacuo gave 1.41 g of a crude oil. The product was purified by column chromatography on 70 g of silica gel eluting with hexanes:ethyl acetate (3:1) to give imide 55 (602 mg, 78%). The material was homogeneous by $^1$H and $^{13}$C NMR. Microanalysis: calc'd C=66.076; H=9.79; N=1.64/observed C=65.38, H=9.54, N=1.56.

EXAMPLE 28

(2S,3R,6S,7R,8S,10S,14R,15S,17S,18R,19S,1'R,3'R,4'R)-E,E-2-(4'-Methoxybenzyloxy)-3-hydroxy-4,10,12,18,20-pentamethyl-6,8,-dimethoxy-7,15,-bis-t-butyldimethylsilyloxy-14-(prop-2'-en-1'-yl)-17-triisopropylsilyloxy-19-((N-t-butyloxycarbonyl-N-methylglycinoyl)-21-(4'-triisopropylsilyloxy-3'-methoxycyclohexyl)-12,20-dienoic acid, 56

EXAMPLE 29

(2S,3R,6S,7R,8S,10S,14R,15S,17S,18R,19S,1'R,3'-R,4'R)-E,E-2-(4'-Methoxybenzyloxy)-3-triethylsilyloxy-4,10,12,18,20-pentamethyl-6,8-dimethoxy-7,15-bis-t-butyldimethylsilyloxy-14-(prop-2'-en-1'-yl)-17-triisopropylsilyloxy-19-((N-methylglycinoyl)-21-(4'-triisopropylsilyloxy-3'-methoxycyclohexyl)-12,20-dienoic acid 56A

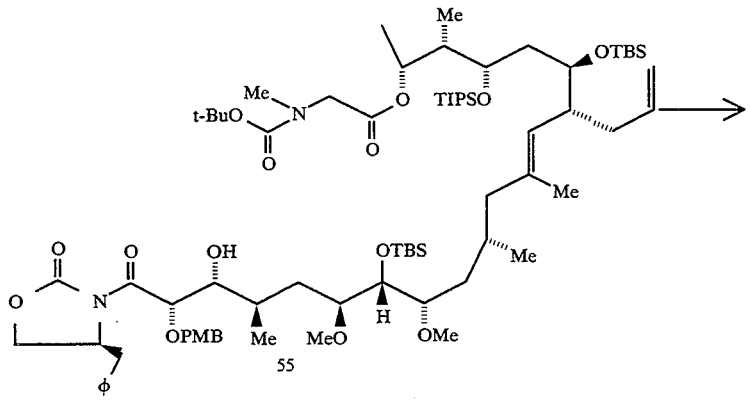

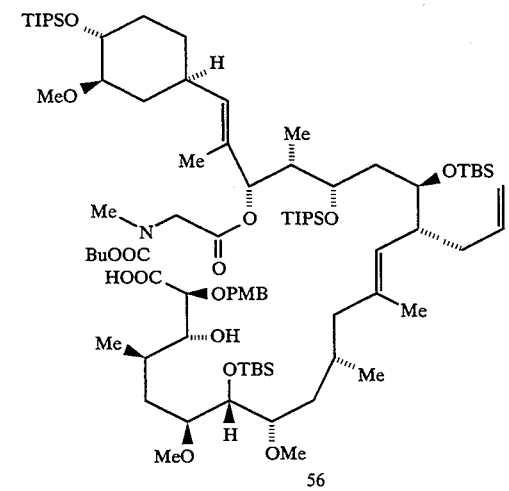

Alcohol 55 (543 mg, 0.318 mmol) was dissolved in 6.0 ml of tetrahydrofuran and 1.35 ml of water and cooled to 0° C. Aqueous 30% hydrogen peroxide solution (0.26 ml, 8.0 equiv) and lithium hydroxide monohydrate (26.9 mg, 0.641 mmmol) were added. The mixture was stirred at 0° C. for 1.5 hr. and then concentrated in vacuo to remove the tetrahydrofuran. The reaction was quenched at 0° C. by addition of 7.3 ml of 10% aqueous sodium bisulfate solution. The mixture was diluted with 20 ml of hexanes and the pH was adjusted to 3.0–3.5 with 0.5N sodium bisulfate solution. The mixture was extracted with 3×50 ml of hexanes and the combined organic layers were washed with 20 ml of water and dried over sodium sulfate. Concentration in vacuo gave 464 mg (94.3%) of the desired carboxylic acid 56.

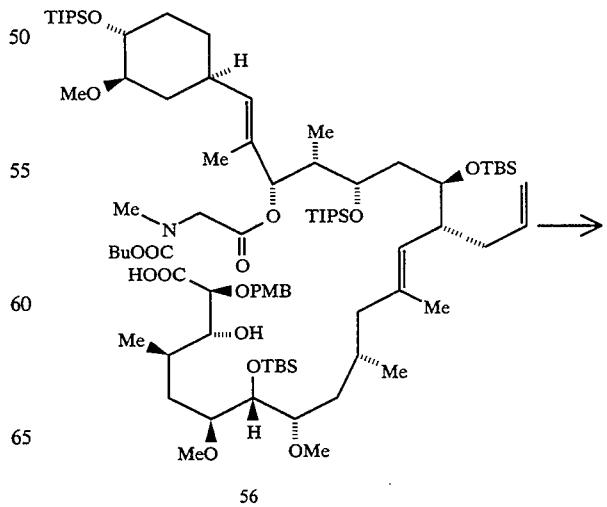

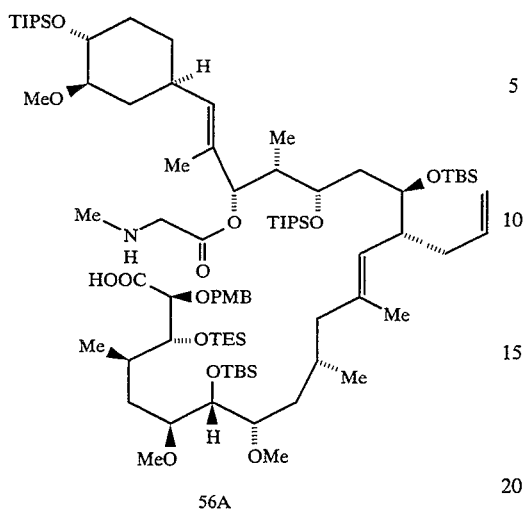

56A

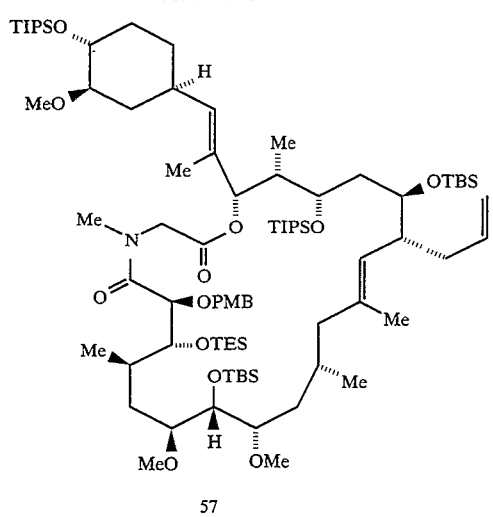

57

Acid 56 (565 mg, 0.365 mmmol) was dissolved in 7.0 ml of methylene chloride at 0° C. and 2,6-lutidine (0.255 ml, 6.0 equiv) were added. Triethylsilyltriflate (0.372 ml, 4.5 equiv) was added and the mixture was stirred at 0° C. for 30 minutes. The reaction mixture was diluted with 5 ml of distilled water and extracted with 3×25 ml of hexane. The hexane portions were combined, dried over sodium sulfate and concentrated in vacuo (bath temperature was maintained at 15° C. or less). The concentrate was then dissolved in methylene chloride and passed through a column containing 83.5 g of silica gel. Column elution was with 700 ml of methylene chloride; 930 ml of 1% methanol/methylene chloride; 700 ml 4% methanol/methylene chloride; and 1000 ml 8% methanol methylene chloride. The column rich cuts were combined and concentrated to give 330 mg of the amino acid 56A (57.9%).

EXAMPLE 30

C.9-(P-Methoxybenzyloxy)-C.10-triethylsilyloxy-C.14,C.22-bis-t-butyldimethylsilyloxy-C.24,C.32-bis-(triisopropylsilyloxy)-hexahydro-FK-506 (FK-506 numbering system) 57

2-Chloro-N-methylpyridinium iodide (62.8 mg, 1.2 equiv) was dissolved in 150 ml of methylene chloride under a nitrogen atmosphere and 0.053 ml of triethylamine was added. Amino acid 56A (330 mg, 0.211 mmol) in 15 ml of anhydrous methylene chloride containing 0.088 ml of triethylamine was added via syringe over a period of 1.5 hr at 25° C. The mixture was stirred at 25° C. for 13 hr. and then diluted with 20 ml of water. The layers were separated and the aqueous layer was extracted with 2×25 ml of methylene chloride. The organic portions were combined dried over sodium sulfate and concentrated in vacuo to give 380 mg of an oil. The crude oil was purified by column chromatography on silica gel (38 g, elution with hexanes/ethyl acetate 15:1). The rich cuts were combined and concentrated to give the desired macrocycle 57 (191 mg, 58.6% yield).

EXAMPLE 31

C.9,C.10-Dihydroxy-C.14,C.22-bis-t-butyldimethylsilyloxy-C.24,C.32-bis-triisopropylsilyloxy-FK-506 analog 59

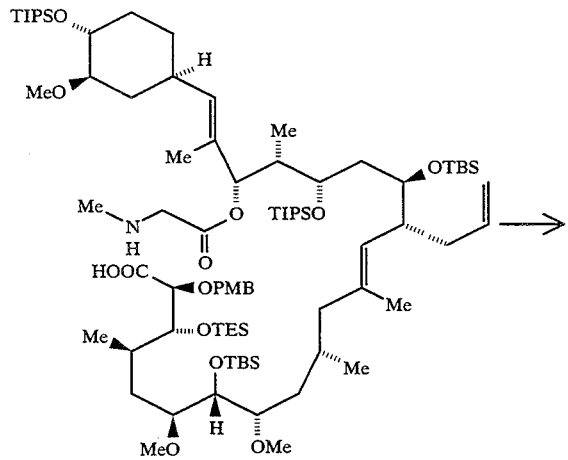

56A

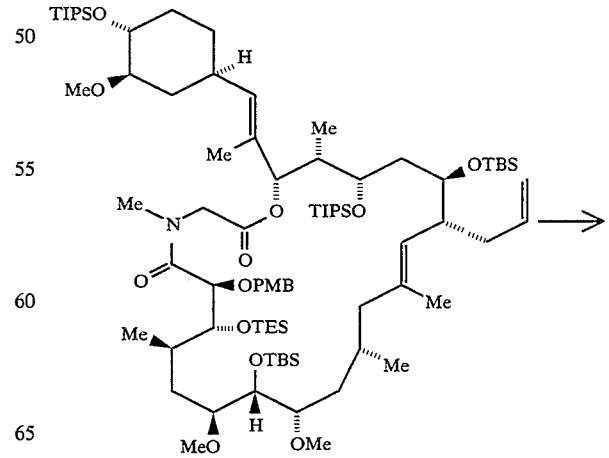

57

-continued

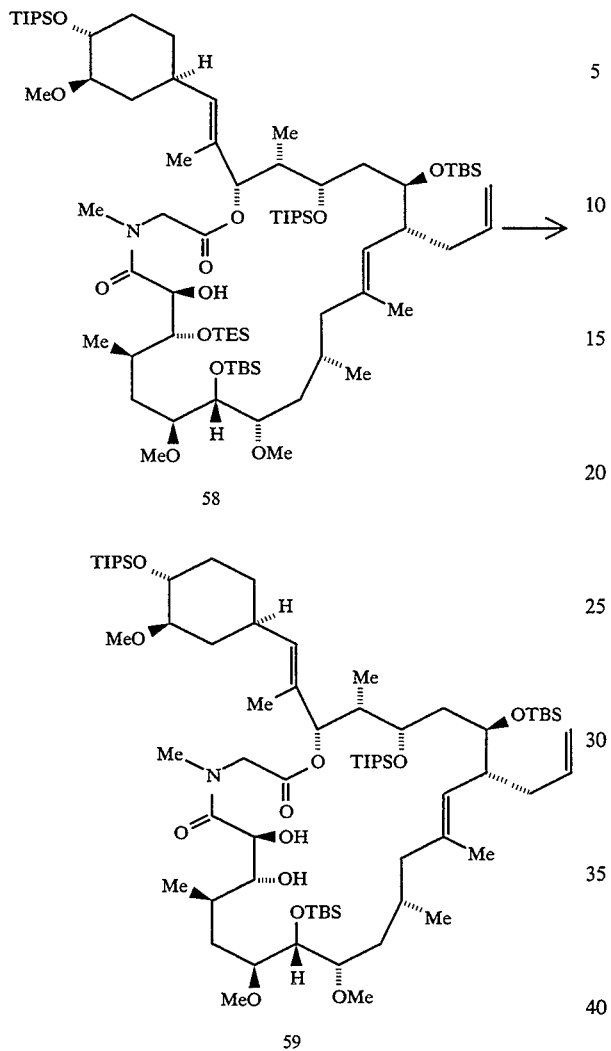

58

59

Macrocycle 57 (182 mg, 0.118 mmol) was dissolved in 3 ml of methylene chloride containing 0.18 ml of water and the mixture was stirred at 25° C. 2,3-dichloro-5,6-dicyano-1,4-benzoquinone (134 mg, 0.59 mmol) was added and the mixture was stirred at 25° C. for 5 hr. The crude mixture was then chromatographed on 42 g of silica gel (400 mesh, eluting with 200 ml methylene chloride; 320 ml 15:1 hexanes/ethyl acetate; 280 ml 6:1 hexanes/ethyl acetate). The rich cuts were combined and concentrated in vacuo to give 132 mg of hydroxy-triethylsilyloxy macrocycle 58 as an oil (79%) and the diol 59 (9.3 g, 6%). The mixture of alcohols was dissolved in 5.3 ml of tetrahydrofuran containing 0.6 ml of water and 0.086 ml of trifluoracetic acid. The mixture was then stirred at 25° C. for 3.5 hr. The mixture was diluted with 10 ml of saturated sodium bicarbonate solution and extracted with 3×25 ml of ethyl acetate. The combined organic phases wee dried over sodium sulfate, concentrated in vacuo, and chromatographed on silica gel) elution with 6:1 hexanes:ethyl acetate) to give 107 mg of diol 59 (88% yield).

EXAMPLE 32

C.14,C.22-Bis-t-butyldimethylsilyloxy-C.24,C.32-bis-triisopropylsilyloxy-FK-506 analog 60

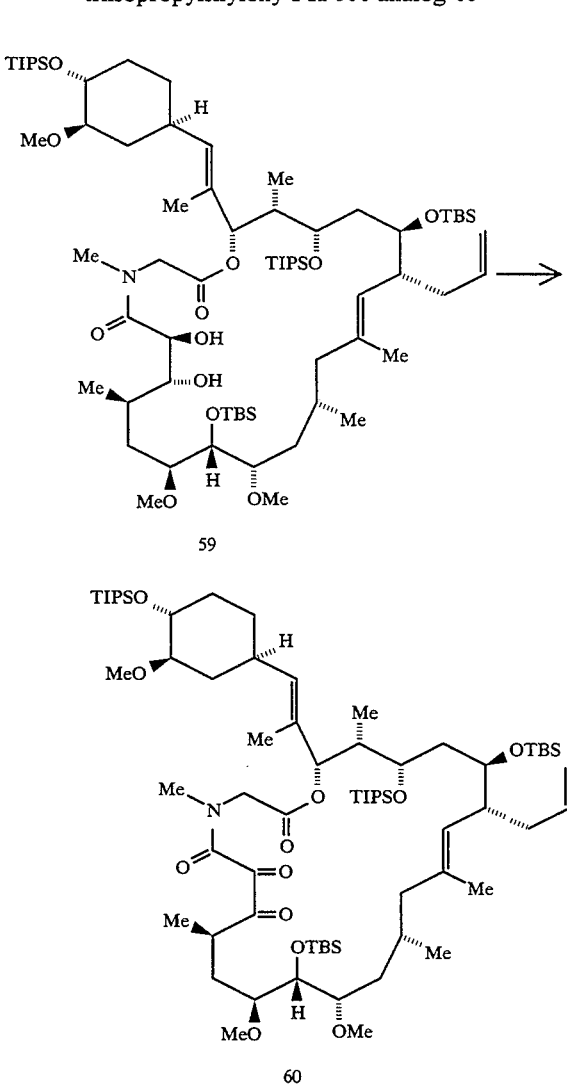

59

60

Oxalyl chloride (0.095 ml, 12 equivalents) was dissolved in 1.0 ml of methylene chloride and cooled to −78° C. under nitrogen. Dimethyl sulfoxide (0.129 ml, 20 equiv) was added and the mixture was stirred for 20 minutes. The dihydroxy macrocycle 59 (118.9 mg, 0.091 mmmol) dissolved in 2.0 ml of methylene chloride was added to the oxidant solution and the mixture was stirred at −78° C. for 3 hr. Triethylamine (0.637 ml, 50 equiv) was added and the mixture was warmed to −30° C. and stirred for 1 hr. The reaction was quenched by the addition of 15 ml of 0.5N sodium bisulfate solution and the mixture was extracted with 3×25 ml of ethyl acetate. The ethyl acetate phases were combined, dried over sodium sulfate, concentrated in vacuo and purified by chromatography on silica gel (eluting with 70 ml 8:1 hexanes/ethyl acetate: 70 ml 6:1 hexanes/ethyl acetate) to give the desired diketo macrocycle 60 as an oil (67.9 mg) plus 39.5 mg of monooxidized product. The monooxidized product was resubjected to the above reaction conditions to give an addition 32 mg of the desired diketone 60 (85% overall yield). The diketo macrocycle 60 was homogeneous by both $^1$H and $^{13}$C NMR.

EXAMPLE 33

C.22-Dihydro-FK-506 analog 61

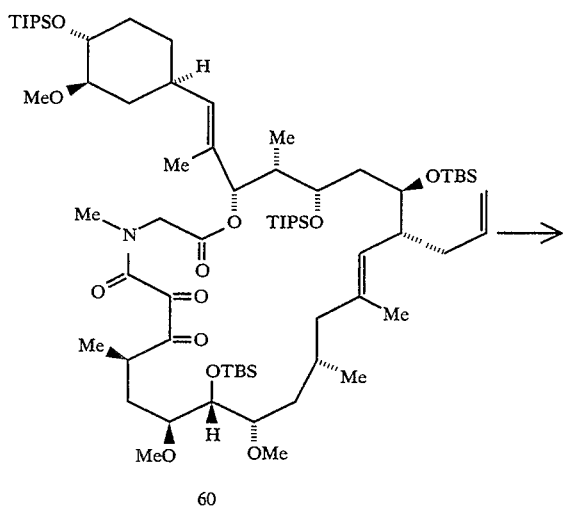

60

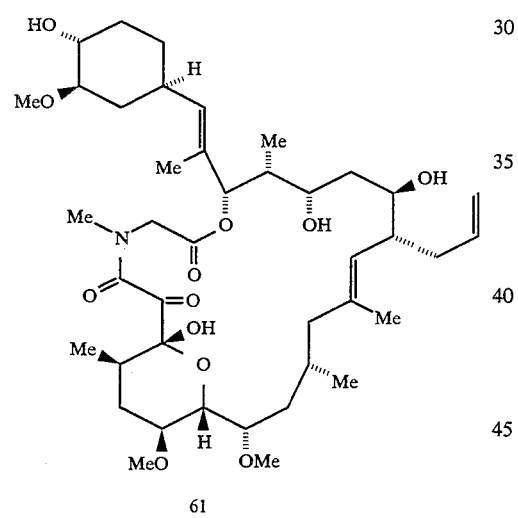

61

Diketo-macrocycle 60 was dissolved in 5 ml of acetonitrile at 0° C. and 5 drops of 50% aqueous hydrofluoric acid was added. The mixture was stirred at 0° C. for 8 hr. and then diluted with 12 ml of saturated aqueous sodium bicarbonate solution. The mixture was extracted with 4×20 ml of ethyl acetate and the organic layers were combined, dried over sodium sulfate, and concentrated in vacuo to an oil (70 mg). The oil was purified by chromatography on silica gel (10 g, elution with 100 ml 1:2 hexanes/ethyl acetate and then 100 ml of ethyl acetate) to give 45.3 mg of compound 61 (80%).

EXAMPLE 34

C.24,C.32-Bis-triethylsilyloxy-FK-506 analog 62

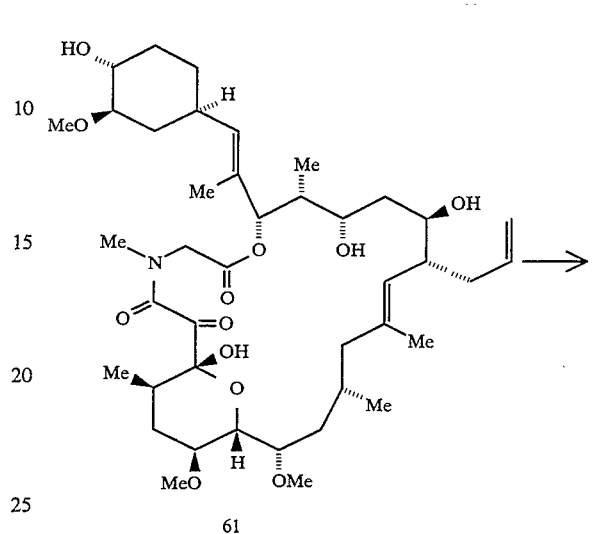

61

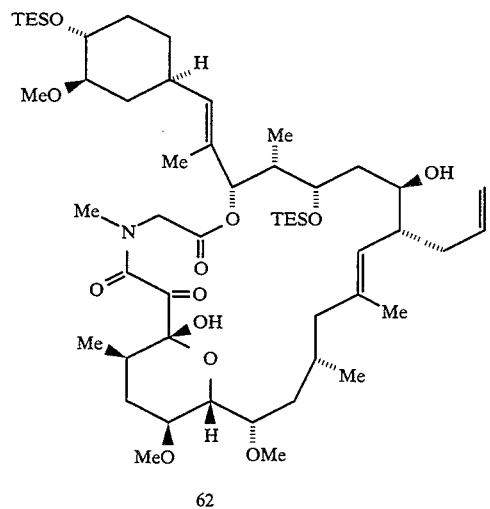

62

Analog 61 (45.1 mg, 0.059 mmol) was dissolved in 1.5 ml of anhydrous pyridine at 0° C. under a nitrogen atmosphere and triethylsilylchloride (0.021 ml, 2.1 equivalents) was added. The mixture was stirred for 12 hr at 0° and then diluted with 5 ml of saturated sodium bisulfate solution. The mixture was extracted with 3×5 ml of ethyl acetate, the organic phases were combined, dried over sodium sulfate, and concentrated in vacuo. Chromatography of the residual oil on silica gel (elution with 60 nml 5:1 hexanes/ethyl acetate; 50 ml of 4:1 hexanes/ethyl acetate; 80 ml of 3:1 hexanes/ethyl acetate) to give the bis-triethylsilyloxy compound 62 (20 mg).

EXAMPLE 35

C.24,C.32-Bis-triethylsilyloxy-FK-506 Sarcosine analog 63

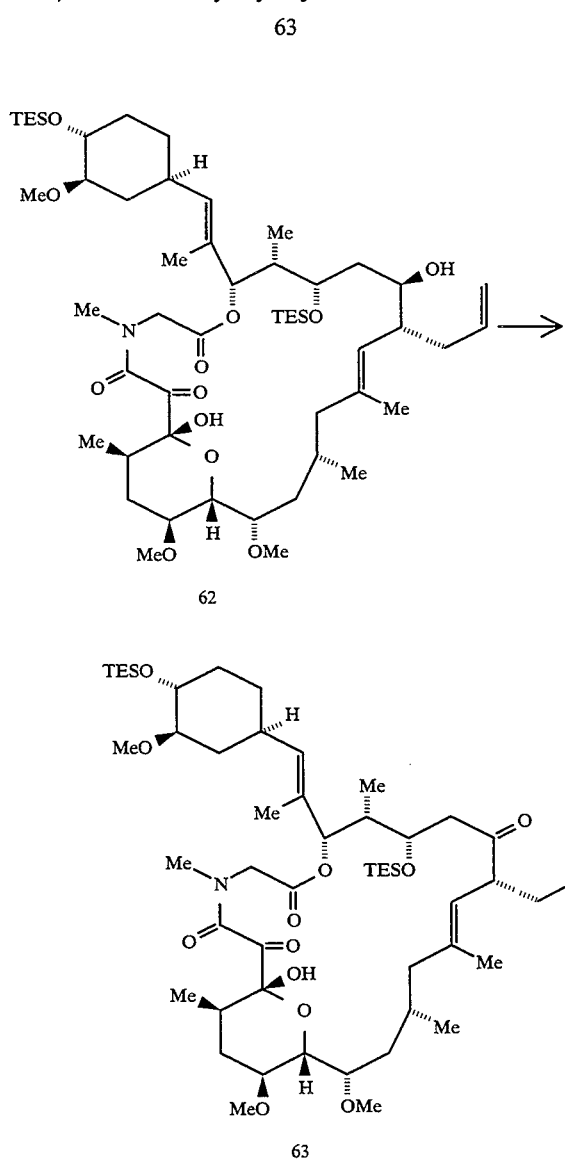

The C.22 alcohol 62 (20 mg, 0.020 mmmol) was dissolved in 1.0 ml of CDCl3 under nitrogen and pyridine (0.005 ml, 3 equiv) was added followed by Dess-Martin perioindane (14.5 mg, 1.7 equiv). The reaction mixture was aged for 45 minutes at 25° C. Both tlc (hexanes-:ethyl acetate 2/1) and NMR analysis showed the absence of starting material at this time. The mixture was partitioned between 5 ml of methylene chloride and 10 ml of saturated sodium sulfate, and concentrated in vacuo to give 25.5 mg of a crude oil. The oil was purified by chromatography on silica gel (5 g, elution with 3:1 hexanes/ethyl acetate) to give 16.5 mg of the desired bis-triethylsilyl ketone 63 (82.7%). This material was homogeneous by both $^1$H and $^{13}$C NMR.

EXAMPLE 36

FK-506 Sarcosine analog 64

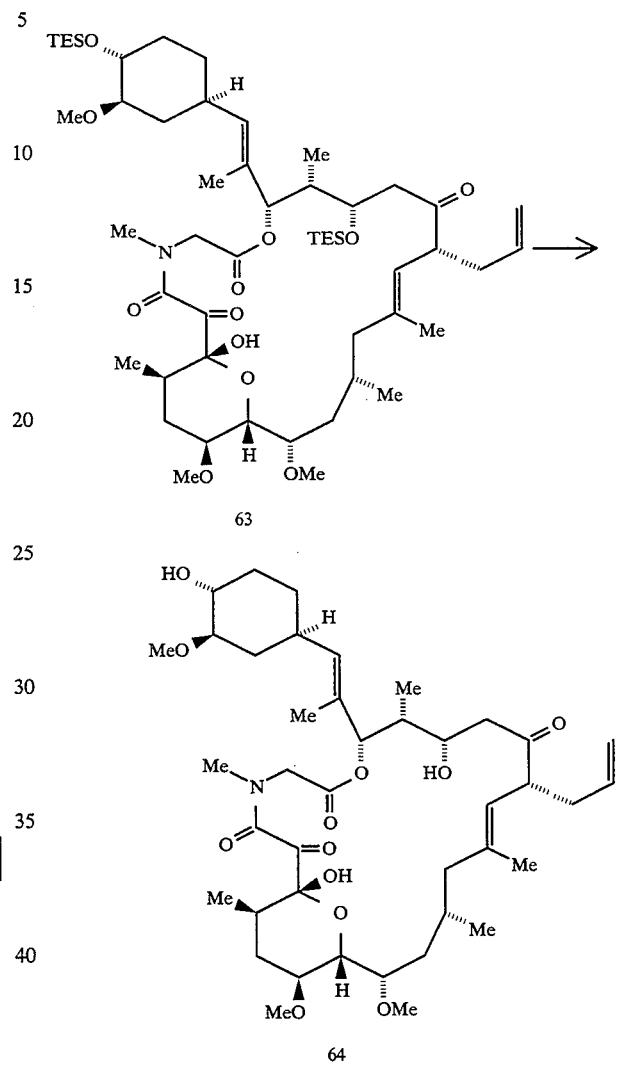

The silyl derivative 63 (16.3 mg) was dissolved in 2.0 ml of acetonitrile and cooled to 0° C. One drop of 50% aqueous hydrofluoric acid was added and the mixture was aged at 0° C. for 1 hr. The mixture was diluted with 5 ml of saturated aqueous sodium bicarbonate solution and extracted with 5×20 ml of ethyl acetate. The organic phases were combined, washed with 10 ml of saturated sodium chloride solution, dried over sodium sulfate, and concentrated in vacuo to give 14.2 mg of crude product. This material was purified by chromatography on silica gel (5 g, elution with 50 ml of 1:2 hexanes/ethyl acetate and then 50 ml of ethyl acetate) to give 11 mg of the FK-506 Sarcosine analog 64 (87.2% yield).

$^{13}$CNMR (CDCl3, 75.5 MHz, 16 mg/mL, major rotamer) δ 212.6, 191.7, 166.5, 166.3, 139.7, 135.4, 131.1, 129.7, 123.0, 116.6, 98.5, 84.1, 77.5, 77.1, 74.0, 73.5, 71.1, 69.2, 57.7, 56.5, 56.2, 52.4, 49.4, 48.5, 44.8, 40.5, 36.9, 35.0, 34.9, 34.8, 34.7, 33.4, 32.3, 31.1, 30.5, 26.3, 20.0, 16.0, 15.8, 14.3, 9.4.

IR (CHCl3) λmax 3600, 1750, 1735, 1700, 1640 cm$^{-1}$
$[\alpha]D^{25} = -132.5°$, C=0.1094, CH2Cl2

EXAMPLE 37

(2R,4S,5R,6S,8S,12R,13S,15S,16R,17S,1'R,3'R,4'R)--E,E-2,8,10,16,18-pentamethyl-1,1,4,6-tetramethoxy-5,13-bis-t-butyldimethylsilyloxy-12-(prop-2'-en-1'-yl)-15-triisopropylsilyloxy-17-((N-t-butylcarboyloxyprolinoyl)-19-(3'-methoxy-4'-triisopropylsilyloxycyclohexyl)-nonadecan-10,18-diene, 66

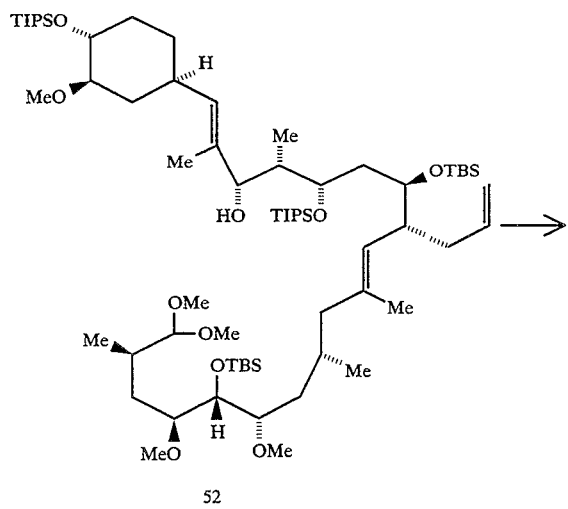

52

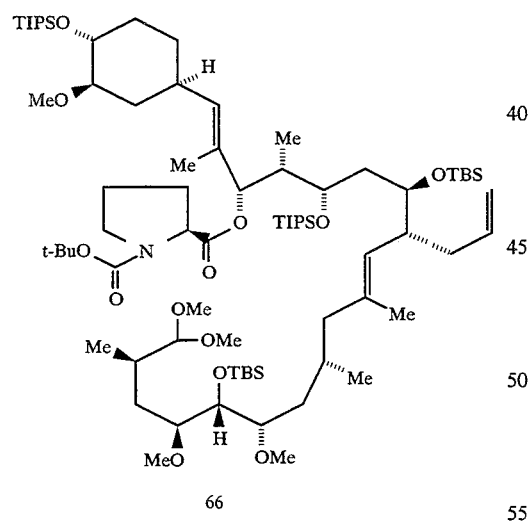

66

Alcohol 52 (1.07 g, 0.87 mmmol) was acylated with N-t-boc-L-proline (751 mg) and dicyclohexylcarbodiimide (740 mg)/4-N,N-dimethylaminopyridine (24 mg) in 17 ml of anhydrous methylene chloride following the procedure cited in Example 25 to give 1.165 g of ester 66 (94% yield). The material was homogeneous by $^1$H and $^{13}$C NMR and had a rotation $[\alpha]D^{25} = -42.73°$ in methylene chloride at c=1.16 g/100 ml.

EXAMPLE 38

(2R,4S,5R,6S,8S,12R,13R,15S,16R,17S,1'R,3'R,4'R)--E,E-4,6-dimethoxy-2,8,10,16,18-pentamethyl-5,13-bis-t-butyldimethylsilyloxy-12-(prop-2'-en-1'-yl)-15-triisopropylsilyloxy-17-((N-t-butylcarboyloxy-L-prolinoyl)-19-(3'-methoxy-4'-triisopropylsilyloxycyclohexyl)-nonadecan-10,18-dienal, 67

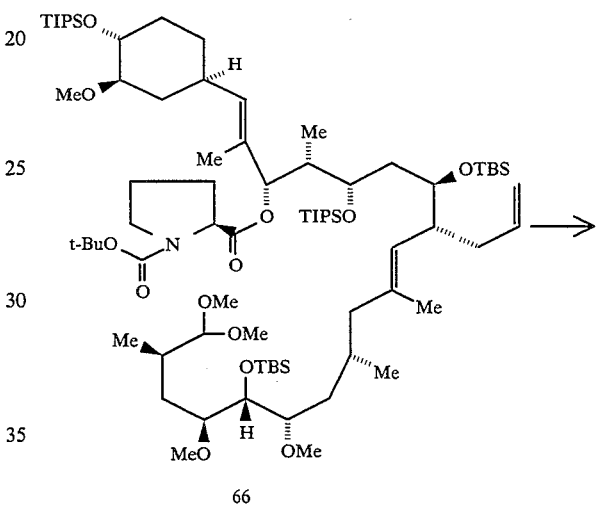

66

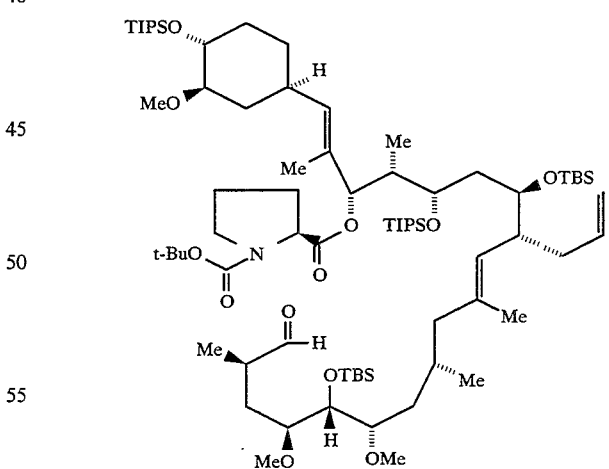

67

Dimethyl acetal 66 (1.165 g, 0.82 mmol) was converted to aldehyde 67 via the procedure described in Example 26 (yield) 1.13 g, 99%). The material was homogeneous by both $^1$H and $^{13}$C NMR.

EXAMPLE 39

(2S,3R,4R,6S,7R,8S,10S,14R,15S,17S,18R,19S,1′R,3′R,4′R)-E,E-2-(p-Methoxybenzyloxy)-3-hydroxy-4,10,12,18,20-pentamethyl-6,8-dimethoxy-7,15-bis-t-butyldimethylsilyloxy-14-(prop-2′-en-1′-yl)-17-triisopropylsilyloxy-19-((N-t-butylcarboyloxy-L-prolinoyloxy)-21-(3′-methoxy-4′-triisopropylsilylyoxycyclohexyl)-12,20-dienoic acid derived oxozolidin-2′-one imide 68 triethylamine (4.0 equivalents) according to the procedure of Example 27. Yield after chromatography on silica gel was 1.04 g (87.8%) of imide 68. The material was homogeneous by $^1$H and $^{13}$C NMR.

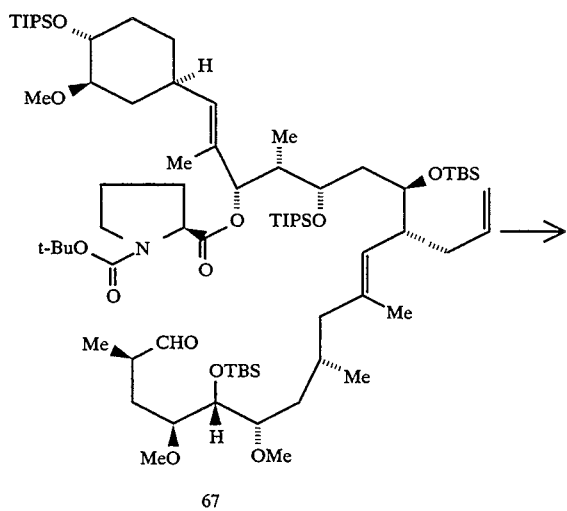

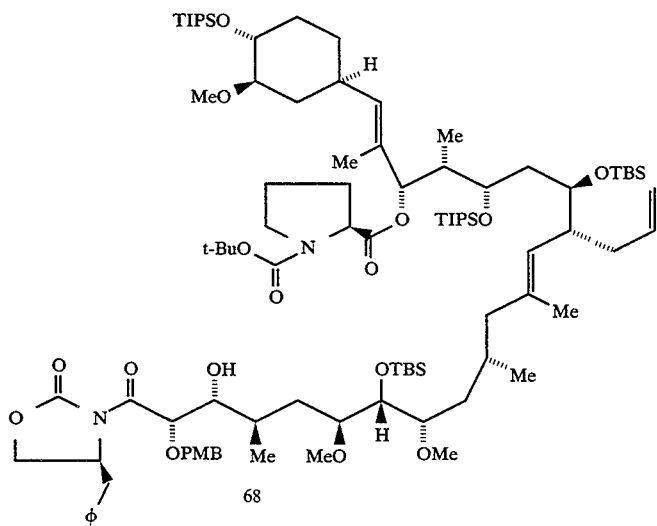

Aldehyde 67 (918.6 mg) was converted to the imide 68 with acetamide 15 (710 mg, 3.0 equivalents), n-dibutylboron triflate (0.483 ml, 2.9 equivalents), and

EXAMPLE 40

(2S,3R,6S,7R,8S,10S,14R,15S,17S,18R,19S,1'R,3'R,4'R)-E,E-2-(4'methoxybenzyloxy)-3-hydroxy-4,10,12,18,20-pentamethyl-6,8-dimethoxy-7,15-bis-t-butyldimethylsilyloxy-14-(prop-2'-en-1'-yl)-17-triisopropylsilyloxy-19-(N-t-butylcarboyloxy-L-prolinoyloxy)-21-(3'-methoxy-4'-triisopropylsilyloxycyclohexyl)-12,20-dienoic acid, 69

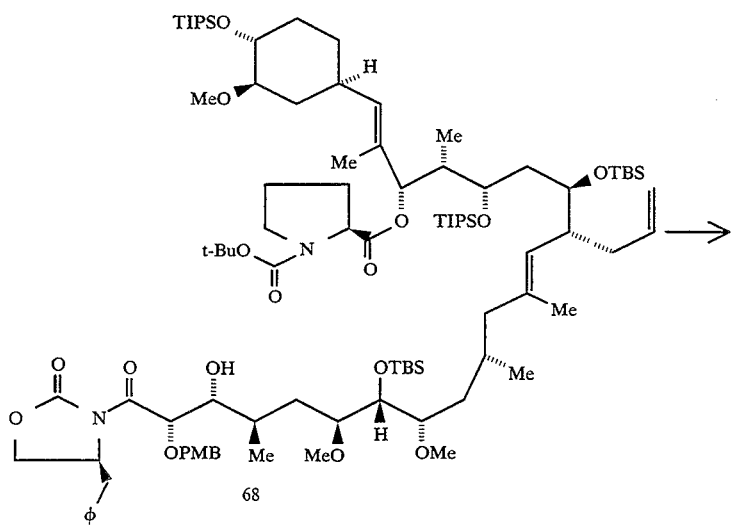

68

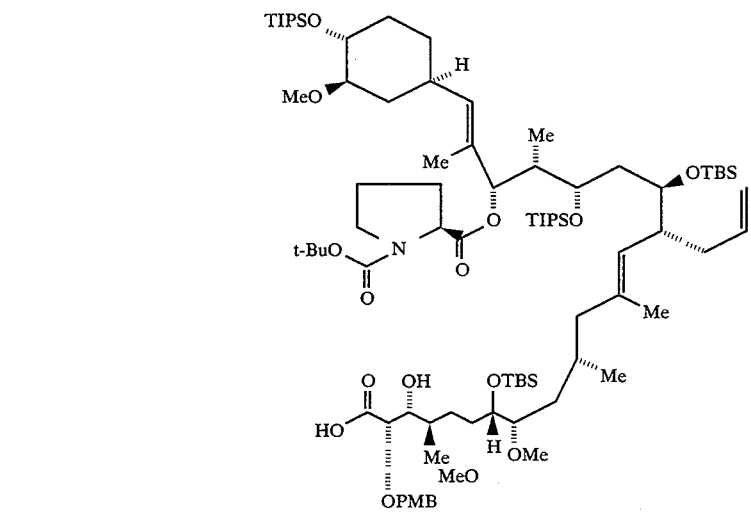

69

Imide 68 (1.191 g) was hydrolyzed according to the protocol described in Example 28 to give 1.081 g of crude acid 69 (quantitative yield). The material was homogeneous by NMR.

EXAMPLE 41

(2S,3R,6S,7R,8S,10S,14R,15S,17S,18R,19S,1′R,3-′R,4′R)-E,E-2-(4′methoxybenzyloxy)-3-triethylsilyloxy-4,10,12,18,20-pentamethyl-6,8-dimethoxy-7,15-bis-t-butyldimethylsilyloxy-14-(prop-2′-en-1′-yl)-17-triisopropylsilyloxy-19-(L-prolinoyloxy)-21-(3′-methoxy-4′-triisopropylsilylyoxycyclohexyl)-12,20-dienoic acid, 70

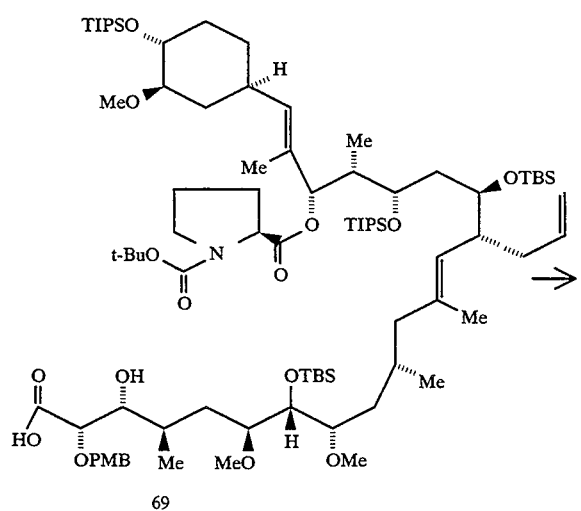
69

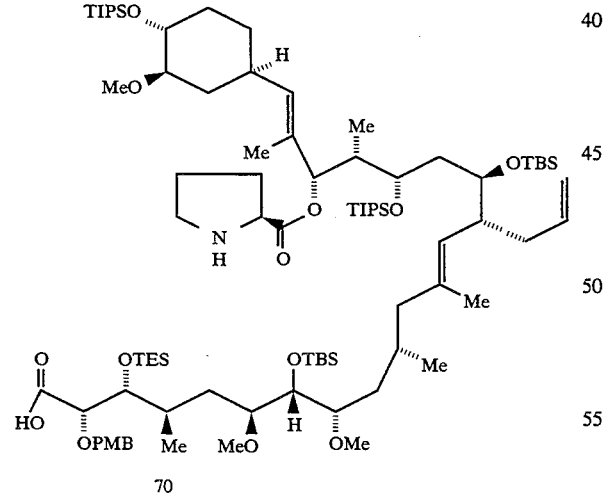
70

Hyroxy-acid 69 (200 mg) was silylated with triethylsilyl triflate (5.5 equivalents) and 2,6-lutidine (6 equivalents) in methylene chloride according to the protocol described in Example 29 to give the triethylsilyloxy acid 70 (154 mg, 76% yield).

EXAMPLE 42

C.9-(p-Methoxybenzyloxy)-C.10-triethylsilyloxy-C.14,C.22-bis-t-butyldimethylsilyloxy-C.24,C.32-bis-triisopropylsilyloxy-hexahydro-FK-525

(FK-numbering system) 71,

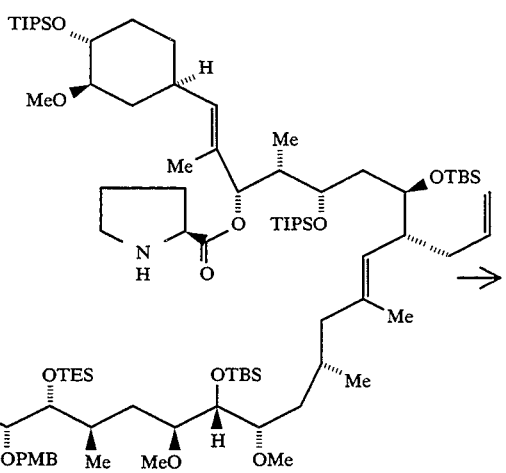
70

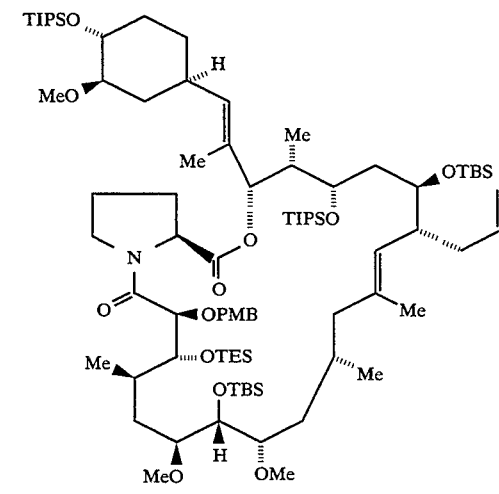
71

Amino-acid 70 (186.5 mg) was cyclized with 2-chloro-N-methylpyridinium iodide (2.0 equivalents) and triethylamine (5 equiv) in methylene chloride via the protocol described in Example 30 to give macrocycle 71 (165 mg) after purification via silica gel column chromatography. Macrocycle 71 was characterized by $^1$H and $^{13}$C NMR.

EXAMPLE 43

C.9,C.10-Dihydroxy-C.14,C.22-bis-t-butyldimethyl-silyloxy-C.24,C.32-bis-(triisopropylsilyloxy)-FK-525, 72

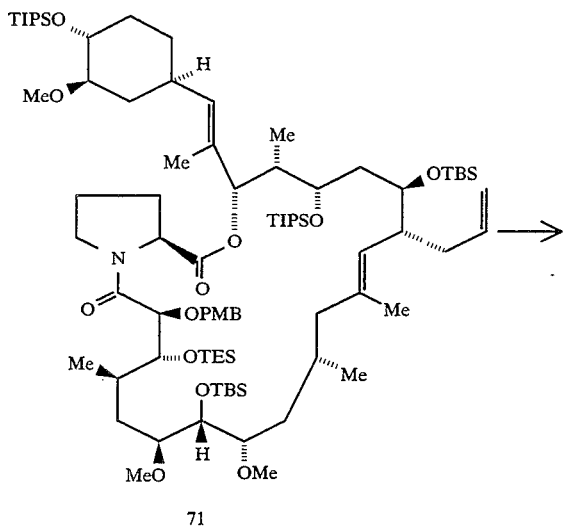

71

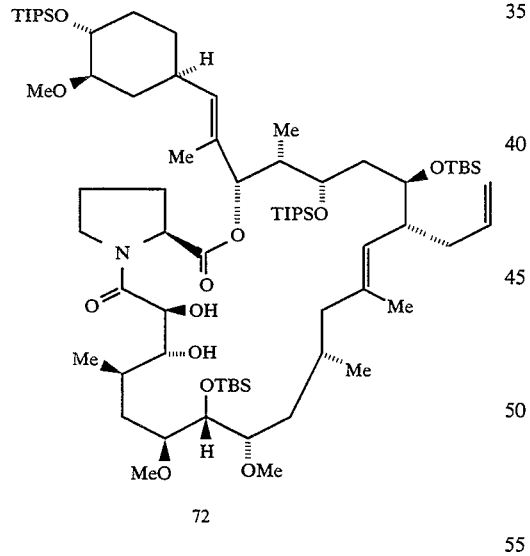

72

The C.9 p-methoxybenzyloxy and C.10-triethylsilyloxy protecting groups of 71 (526 mg, 0.335 mmol) were removed according to the protocol described in Example 31 to give the diol 72 in 80% yield (358 mg). Microanalysis calcd for $C_{73}H_{141}N_{12}Si_4$: C, 65.567; H, 10.627; N, 1.047 Found C-65.67; H=10 43; N=1.05 Rotation $[\alpha]^{25}=56.5°$, C=1.73 in methylene chloride.

EXAMPLE 44

C.9, C.10-Diketo-C.14, C.22-bis-t-butyldimethylsilyloxy-C.24, C.32-bis-(triisopropylsilyloxy)-FK-525, 73

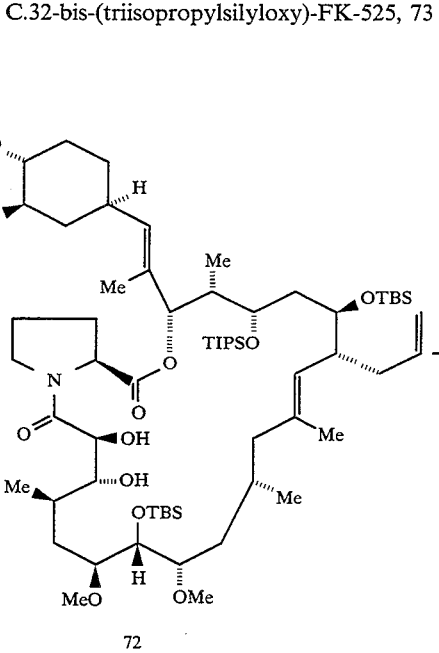

72

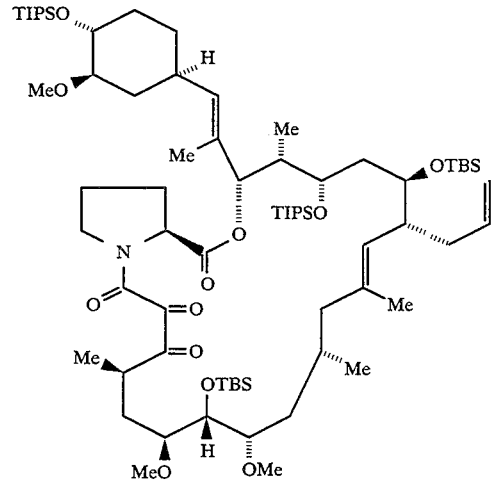

73

Oxidation of diol 72 (230 mg) with oxalyl chloride (12 equiv), dimethylsulfoxide (20 equiv) and triethylamine (50 equiv) in methylene chloride according to the procedure described in Example 32 gave 176 mg of diketone 73 (ca. 77% yield).

EXAMPLE 45

C.22-dihydro-FK-525, 74

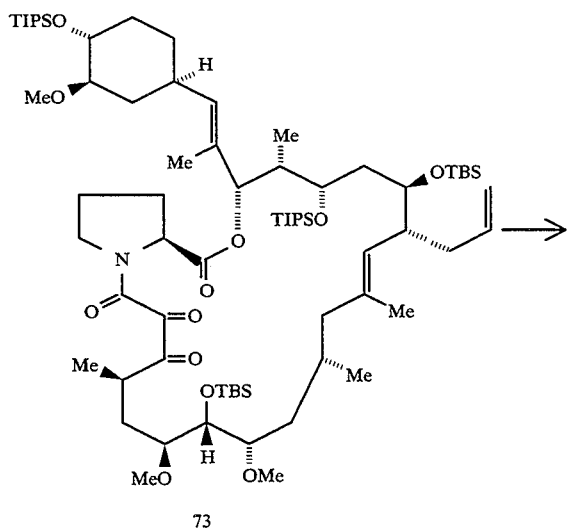

73

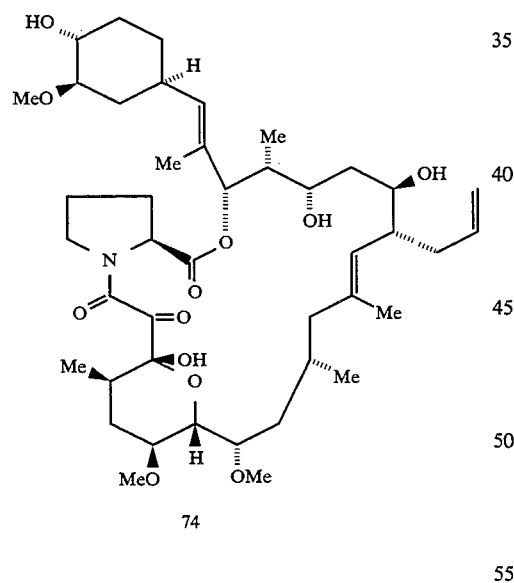

74

Complete desilylation of 73 (145 mg) with hydrogen fluoride in acetonitrile via the protocol of Example 33 gave dihydro-FK-525 (66 mg, 77%). The material was homogeneous by $^1$H and $^{13}$C NMR. Rotation [α]D C=−29.95°, C=0.661 in chloroform, IR 3600, 3550–3200, 1745, 1735 and 1630 cm$^{-1}$.

EXAMPLE 46

C.24,C.32-bis-triethylsilyloxy-dihydro-FK-525, 75

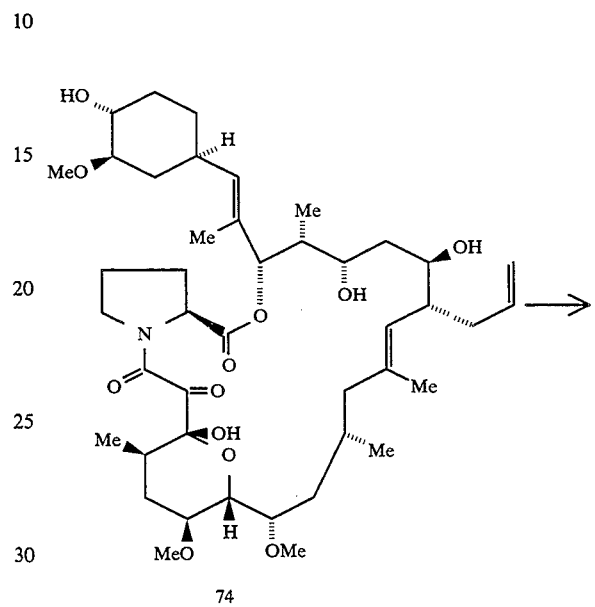

74

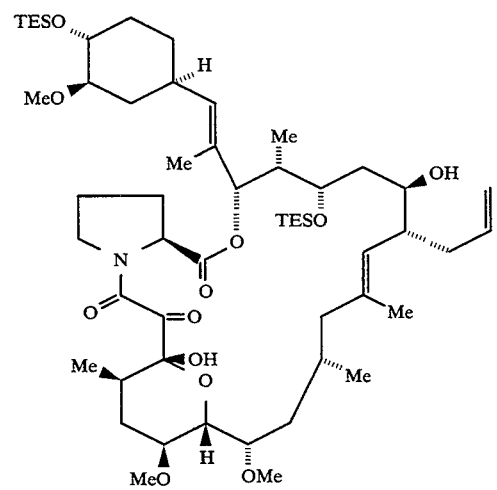

75

Treatment of 74 (8.9 mg) with triethylsilylchloride (2.1 equiv) in pyridine via the protocol of Example 34 gave bis-silyl compound 75 (10.2 mg). The material was characterized by $^1$H and $^{13}$C NMR.

EXAMPLE 47

C.24,C.32-bis-triethylsilyloxy-FK-525, 76

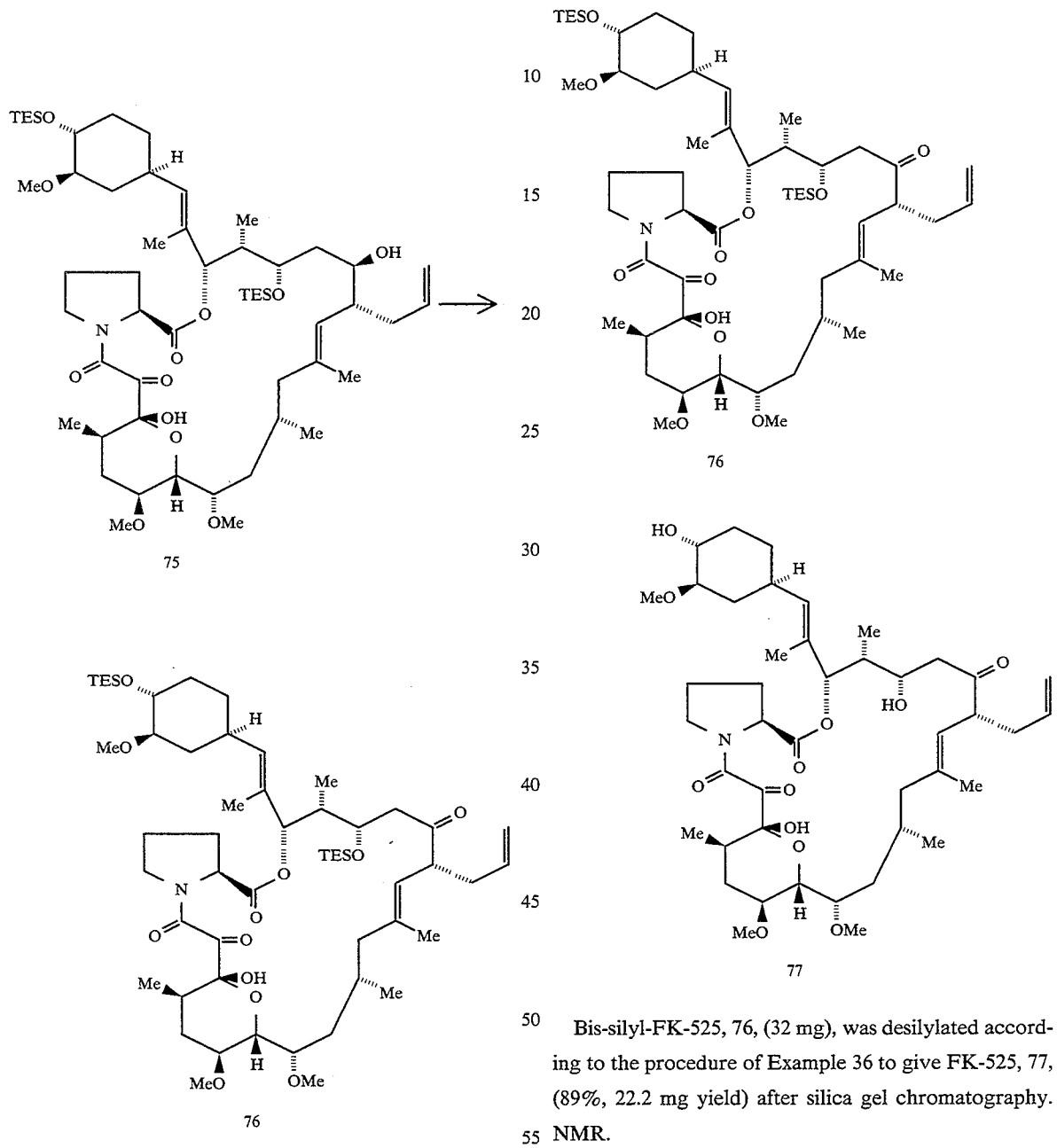

Oxidation of 75 (3.7 mg) with Dess-Martin perioindane (3.9 mg, 1.5 equiv) in methylene chloride (0.5 ml) containing 3.0 equivalents of pyridine via the protocol described in Example 35 gave the bis-protected FK-525 76 (3.6 mg, quantitative yield).

EXAMPLE 48

FK-525, 77

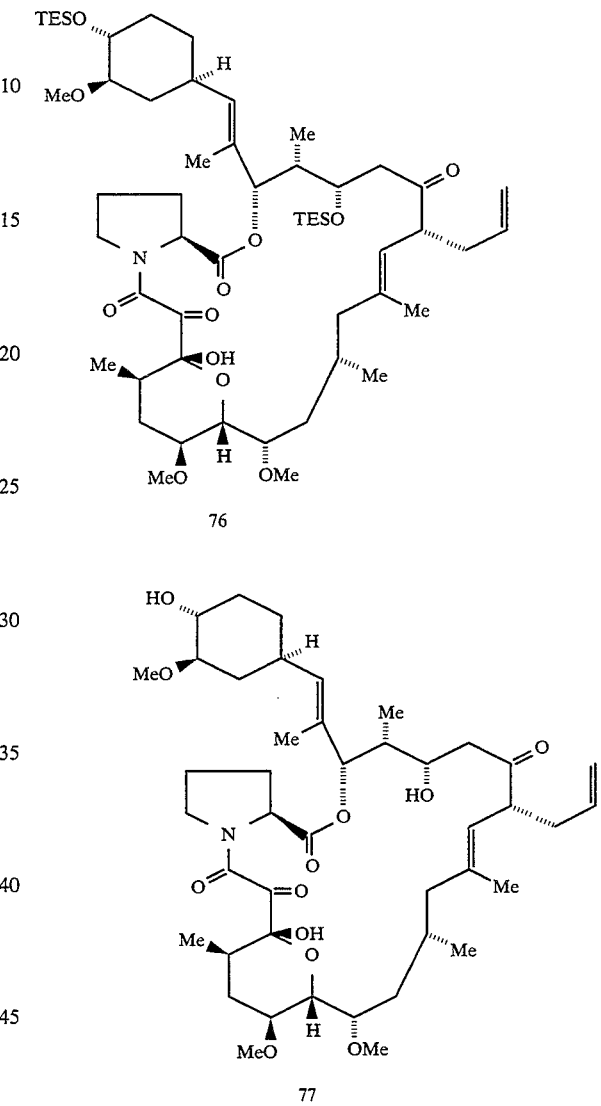

Bis-silyl-FK-525, 76, (32 mg), was desilylated according to the procedure of Example 36 to give FK-525, 77, (89%, 22.2 mg yield) after silica gel chromatography. NMR.

IR (CHCl$_3$): $\lambda_{max}$ 3600, 3500–3200(vb), 1745, 1735, 1695, 1630 cm$^{-1}$ $^{13}$C NMR (CDCl$_3$, 32 mg/mL, major rotamer only, 75.5 MHz): δ 213.1, 187.9, 168.8, 162.5, 140.4, 135.4, 132.1, 129.8, 122.1, 116.6, 99.0, 84.1, 78.4, 76.5, 73.6, 73.5, 71.2, 69.0, 59.9, 57.7, 56.5, 56.2, 53.2, 48.8, 48.5, 44.0, 41.0, 36.1, 35.4, 34.8, 34.7, 32.9, 32.6, 31.1, 30.6, 28.4, 25.7, 25.4, 18.7, 16.1, 15.6, 14.0, 9.6.

$[\alpha]^{25} = -98.5$, C=0.195, CHCl$_3$.

and MS. Anal. Calcd for $C_{62}H_{109}NO_{12}Si_2$: C, 66.685; M, 9.838; N, 1.25. Found: C, 66.88; H, 9.71; N, 1.25.

EXAMPLE 50

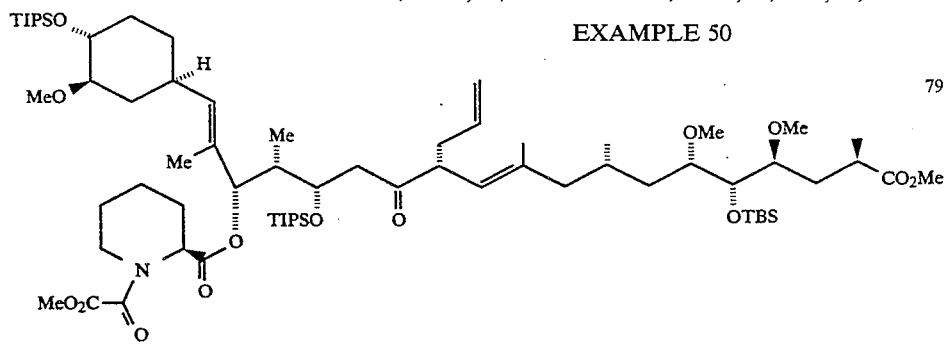

79

Hydroxy-ester 79

To a 25° C. solution of 24,32-FK-506-bis(triisopropylsilyl) ether 78 (23.1 g, 20.7 mmmol) in 300 mL sieve dried benzene and 100 mL sieve dried methanol was added Pb(OAc)$_4$ (9.67 g, 21.8 mmmol) and the resulting mixture was aged at 25° C. for 4 h. The mixture was then quenched into sat'd aqueous NaHCO$_3$ (800 mL) and extracted with ethyl acetate (3×350 mL). The combined ethyl acetate phase was washed with water (350 mL), dried with MgSO$_4$ and concentrated in vacuo to afford 22.9 g of a white gummy foam. The foam was dissolved in methanol (300 mL) at 25° C. concentrated in vacuo to remove any residual ethyl acetate. The foam was then redissolved in sieve dried methanol (350 mL) at 25° C. and anhydrous K$_2$CO$_3$ (145 mg) was added. After 2 h additional K$_2$CO$_3$ (43 mg) was added. After 5 h total reaction time at 25° C. the solution was decanted away from the solid K$_2$CO$_3$ and was concentrated in vacuo to afford 23.4 g of a yellow tinted gum. Chromatography on silica gel (1150 g, 230–400 mesh) with CH$_2$Cl$_2$/acetone (20:1) as the eluent followed by CH$_2$Cl$_2$/acetone (15:1) afforded 2.52 g (10.6%) of the valerolactone 80 as a colorless foam and 16.8 g (69%) of the desired methyl ester 79 as a colorless foam.

EXAMPLE 49

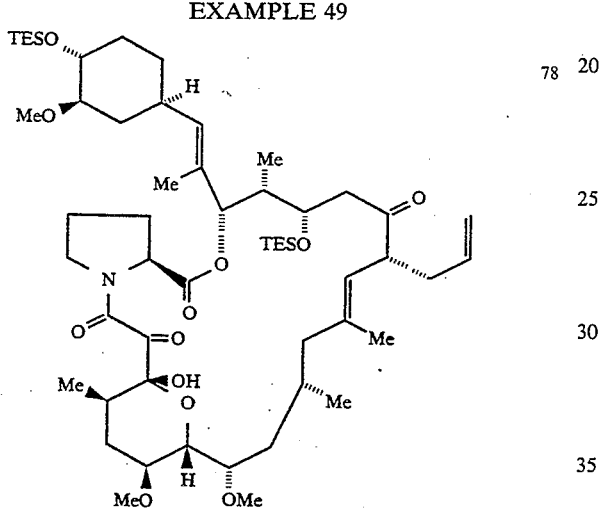

78

24-32-FK-506-bis-(triisopropylsilyl)-ether 78

To a 0° C. solution of FK-506 (10.2 g, 12.68 mmol) in 125 mL sieve dried CH$_2$Cl$_2$ was added 2,6-lutidine (7.4 mL, 63.5 mmol) and TIPSOTf (14.3 mL, 53.2 mmol). After stirring at 0° C. for 1.5 h, the yellow tinted solution was warmed to 25° C. and aged for 16 h. The mixture was then cooled to 0° C. and methanol (1.55 mL, 38.2 mmol) was added dropwise and the resulting solution was aged for 15 min. The mixture was partitioned with sat'd aqueous NaHCO$_3$ (500 mL) and CH$_2$Cl$_2$ (200 mL) and the layers were separated. The aqueous phase was reextracted with CH$_2$Cl$_2$ (2×200 mL). The combined CH$_2$Cl$_2$ phase was washed with water (200 mL), dried with MgSO$_4$ and concentrated in vacuo to afford 20 g of a yellow viscous oil. Chromatography on silica gel (325 g, 230–400 mesh) with hexanes/ethyl acetate (5:1) as the eluent afforded 14.04 g (99%) of 2 as a colorless foam which was characterized by $^1$H, $^{13}$C NMR, IR

EXAMPLE 51

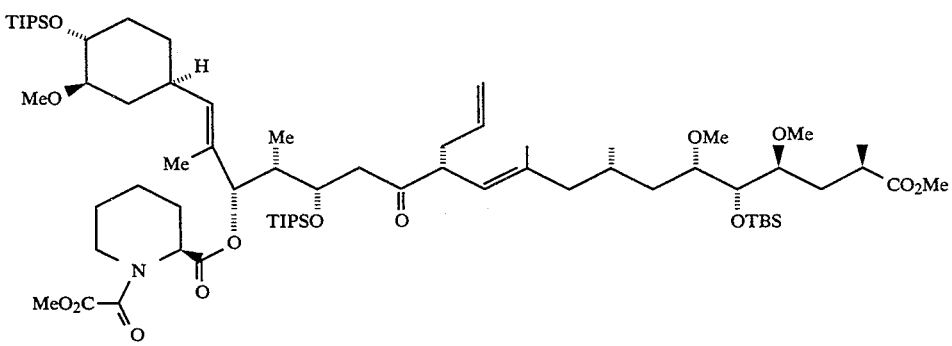

81

C.14 TBS-ether 81

To a 0° C. solution of the hydroxy-ester 79 (16.8 g, 14.25 mmol) in 210 mL dry CH$_2$Cl$_2$ was added 2,6-lutidine (3.3 mL, 28.3 mmol) and then tert-butyldimethylsilyl triflate (4.9 mL, 21.3 mmol) and the solution was stirred at 0° C. for 2 h, then it was allowed to warm to 25° C. After 1 hr at 25° C. additional tert-butyldimethylsilyl triflate (0.35 mL, 1.52 mmol) was added to the 25° C. solution. After an additional 1.5 hr age, the solution was cooled to 0° C. and sieve dried methanol (0.58 mL, 14.3 mmol) was added and the mixture was aged at 0° C. for 15 min. The mixture was partitioned with saturated aqueous NaHCO$_3$ (1000 mL) and extracted with CH$_2$Cl$_2$ (3×300 mL). The combined CH$_2$Cl$_2$ layer was washed with water (1×300 mL), dried with MgSO$_4$ and concentrated in vacuo to afford 21.4 g of a tan oil that was purified by chromatography on silica gel (1,070 g, 230-400 mesh) with hexanes/ethyl acetate (5:1) as the eluent. The TBS ether 81 (14.4 g, 78.3%) was isolated as a white gummy foam and gave satisfactory $^1$H and $^{13}$C NMR, IR and mass spectral data. Anal. Calcd for C$_{70}$H$_{129}$NO$_{14}$Si$_3$: C. 65.02; H, 10.055; N, 1.08. Found: C, 65.18; H, 10.06; N, 1.09.

EXAMPLE 52

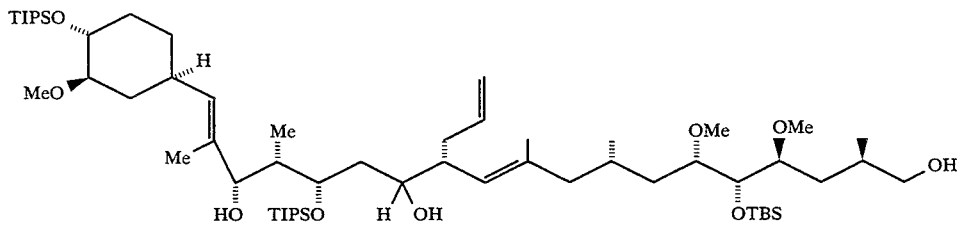

Triols 82 (R/S)

To a 0° C. solution of methyl ester 81 (13.3 g, 10.28 mmol) in sieve dried THF (375 mL) was added lithium aluminum hydride (1.18 g, 31.1 mmol) in several portions, and the gray suspension was aged at 0° C. for 3 h. Diethyl ether (300 mL) was added and then water was cautiously added dropwise until bubbling had stopped (several mL). The mixture was then partitioned with saturated Na$_2$SO$_4$ (400 mL) and extracted with ethyl acetate (3×400 mL). The combined ethyl acetate layer was washed with brine (400 mL), dried with MgSO$_4$ and concentrated in vacuo to afford 11.8 g fo a brownish gummy foam. The crude foam was purified by chromatography on silica gel (580 g, 230-400 mesh) eluting with hexanes/ethyl acetate (3:1) to afford 5.9 g (65.6%) of the triols 82 as an inseparable 2.5 to 1 mixture of C.22-R/S epimers, respectively. Anal. Calcd for C$_{60}$H$_{120}$Si$_3$O$_9$: C, 67.36; H, 11.305. Found: C, 67.39; H, 11.38.

EXAMPLE 53

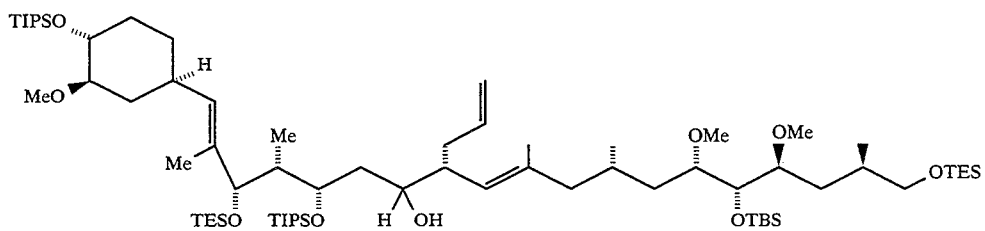

C.22 alcohols 83 (R/S)

To a −10° C. solution of triols 82 (R/S) (2.33 g, 2.18 mmol) in sieve dried pyridine (33 mL) was added TESCl (0.740 mL, 4.40 mmmol) over a 5 minute period. After a 1.75 h age at −10° C., additional TESCl (0.092 mL, 0.55 mmol) was added. After an additional 1 h age, anhydrous methanol (0.088 mL, 2.17 mmol) was added and the mixture was aged at −10° C. for 0.25 hr. The mixture was partitioned with saturated aqueous NaHCO$_3$ (100 mL) and extracted with CH$_2$Cl$_2$ (3×100 mL). The combined CH$_2$Cl$_2$ layer was washed with saturated aqueous NaHCO$_3$ (100 mL), dried with MgSO$_4$ and concentrated in vacuo to afford 3.7 g of a tan viscous oil. The crude mixture was purified by chromatography on silica gel (175 g, 230-400 mesh) with hexanes/ethyl acetate (18:1 to 15:1) as the eluent to afford 2.726 g (96.3%) of the C.22 alcohols 83 (R/S) as a colorless foam. Anal. Calcd for C$_{72}$H$_{148}$O$_9$Si$_5$: C, 66.605; H, 11.49. Found: C, 66.82; H, 11.77.

EXAMPLE 54

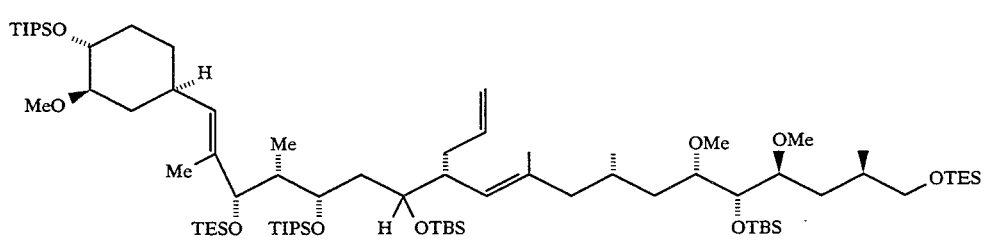

C.22-TBS ethers 84 (R/S)

To a 0° C. solution of C.22 alcohols 83 (R/S) (4.55 g, 3.50 mmol) in 100 mL sieve dried CH₂Cl₂ was added 2,6-lutidine (1.20 mL, 10.3 mmol) and then tertbutyldimethylsilyl triflate (1.60 mL, 6.97 mmol). After 0.5 h the mixture was brought to 25° C. and aged for 14 h. The mixture was cooled to 0° C. and anhydrous methanol (215 @1, 5.30 mmol) was added and the mixture was aged for 0.5 h. The mixture was partitioned with 50% saturated aqueous NaHCO₃ (125 mL) and extracted with CH₂Cl₂ (3×125 mL). The combined CH₂Cl₂ layer was washed with water (125 mL), dried with magnesium sulfate and concentrated in vacuo to afford 5.3 g of a tan oil. The crude mixture was purified by chromatography on silica gel (260 g, 230–400 mesh) eluting with hexanes/ethyl acetate (15:1) to afford 4.86 g (98%) of the C.22 TBS ethers 84 (R/S) as a gummy white foam. Anal. Calcd for C₇₈H₁₆₂O₉Si₆: C, 66.32, M, 11.56. Found: C, 65.93; H, 11.77.

EXAMPLE 55

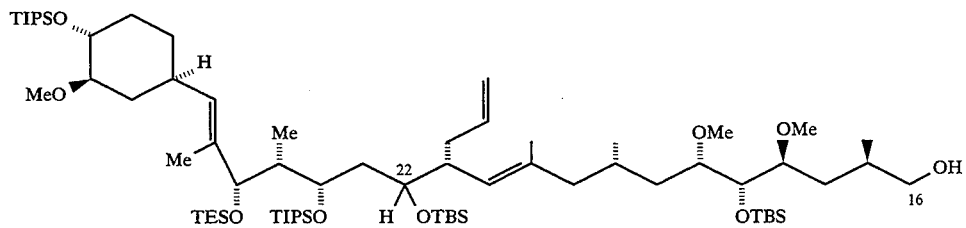

22(R) and 22(S)-C.10 primary alcohols 85

To a solution of bis-TES ethers 84 (R/S) (4.85 g, 3.43 mmol) in 155 mL THF was added 15.5 mL water and 30 mL of acetic acid over a 10 minute period. The mixture was heated to 40° C. and aged for 12 h, then at 50° C. for 2.5 hr. The mixture was cooled to 0° C. and poured slowly into a solution/suspension of 72 g NaHCO₃ in 450 mL H₂O. The mixture was then extracted with ethyl acetate (3×450 mL) and the combined ethyl acetate layer was washed with saturated aqueous NaHCO₃ (115 mL), brine (115 mL) and dried with magnesium sulfate. The volatiles were removed in vacuo to afford 5.01 g of a tan gum that was purified by silica gel chromatography (675 g, 230–400 mesh). Gradient elution with hexanes/ethyl acetate (8:1) to (2:1) afforded 742 mg (16.6%) of pure less polar 2(S)-C.10 primary alcohol 85 (S), 305 mg (6.8%) of mixed fractions and 2.315 g (52%) of the 22(R)-C.10 primary alcohol 85 (R) which had ¹H and ¹³C NMR, IR and MS data consistent with the structure. Anal. Calcd for C₇₂H₁₄₈O₉Si₅: C, 66.605; H, 11.489. Found: C, 66.47; H, 11.73.

EXAMPLE 56

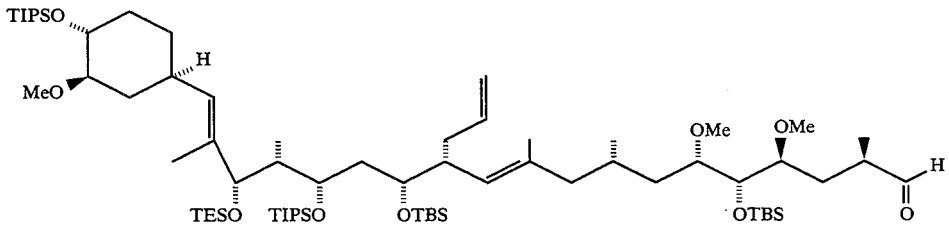

Aldehyde 86

To a −78° C. solution of oxalyl chloride (148 @1, 1.70 mmol) in 10 mL sieve dried CH₂Cl₂ was added a solution of dimethyl sulfoxide (200 @1, 2.82 mmol) in 4 mL CH₂Cl₂ over a period of 5 min and the resulting mixture was aged at −78° C. for 0.5 h. A solution of the primary alcohol 85 (R) (1.06 g, 0.816 mmol) in 10 mL CH₂Cl₂ was added to the −78° C. chlorosulfonium salt solution followed by a 5 mL CH₂Cl₂ flush. The resulting white slurry was aged at −78° C. for 1.5 h, then triethylamine (983 @1, 7.05 mmol) was added and the solution warmed to −40° C. and aged at −40° C. for 1 h. Aqueous NaHSO₄ (0.5M, 75 ml) was added at −40° C. and the mixture was extracted with hexanes (4×100 mL). The combined hexane layer was washed with water (1×50 ml), dried with MgSO₄ and concentrated in vacuo to afford 1.05 g of crude material that was chromatographed on silica gel (90 g, 230–400 mesh). Elution with hexanes/ethyl acetate (15:1) gave 977 mg (95.8%) of the aldehyde 86 as a white foam. Aldehyde 86 gave ¹H and ¹³C NMR, IR and MS data in accord with its structure.

EXAMPLE 57

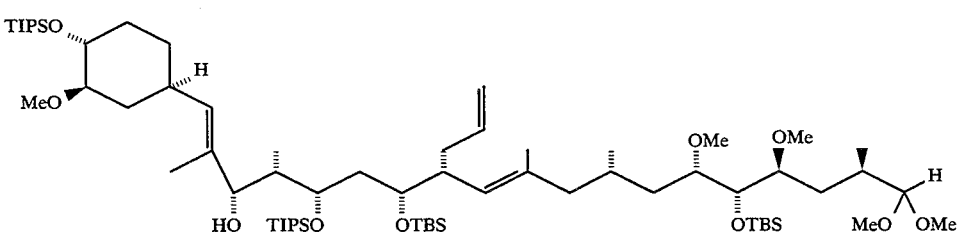

Dimethyl acetal 87

To a solution of aldehyde 86 (2.07 g, 1.60 mmol) at 0° C. in 105 mL sieve dried THF was added methanol (155 mL), trimethylorthoformate (3.13 mL, 28.6 mmol) and pyridinium para-toluenesulfonate (555 mg, 2.2 mmol) and the mixture was warmed to 18° C. After 2 h, 444 mg of pyridium para-toluenesulfonate was added, and the mixture was warmed to 25° C. After 3 h at 25° C., pyridine (4.9 mL, 60.5 mmol) was added with ice bath cooling and the mixture was poured into 250 mL saturated aqueous NaHCO3 and extracted with CH2Cl2 (3×200 mL). The combined CH2Cl2 layer was washed with 50% aqueous NaHCO3 (120 mL), dried with MgSO4 and concentrated in vacuo. The resulting crude oil was chromatographed on 200 g SiO2 (230–400 mesh) eluting with hexanes/ethyl acetate ((15:1), 1.6 L; (8:1), 850 mL; (3:1), flush) to afford 1.637 g (83.5%) of the dimethyl acetal 87 as a colorless oil, which exhibited $^1$H and $^{13}$C NMR, IR and MS consistent with its structure. Anal. Calcd for $C_{68}H_{138}O_{10}Si_4$: C, 66.501; H, 11.325. Found: C, 66.43;, H, 11.68.

EXAMPLE 58

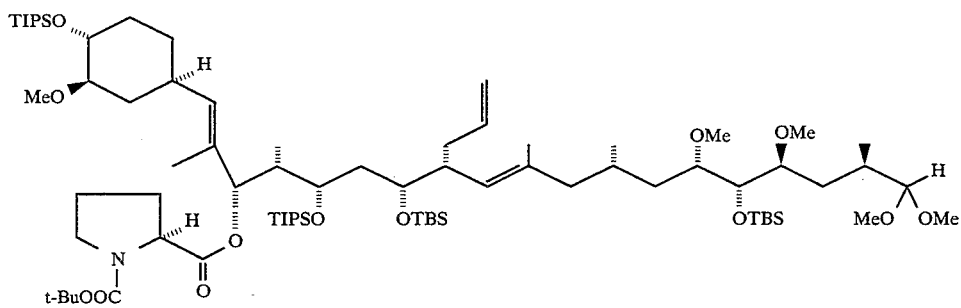

N-BOC proline ester 88

To a solution of C.26 alcohol 87 (388.5 mg, 0.316 mmol) in 6 mL dry CH2Cl2 at −50° C. was added solid N-Boc-(L)-proline (273 mg, 1.27 mmol) then 1,3-dicyclohexylcarbodiimide (DCC, 262 mg, 1.27 mmol) and N,N-dimethylaminopyridine (DMAP, 7.8 mg, 0.064 mmol) and the resulting solution was aged at −50° C. for 1.5 h. The mixture was warmed to −19° C. and aged for 30 h, then N-BOC-(L)-proline (136 mg), 131 mg DCC and 4 mg DMAP were added and the slurry was aged again for 24 h. The slurry was then warmed to 25° C., filtered to remove the ppt. and the filter cake was washed with hexanes/ethyl acetate (6:1). The volatiles were removed in vacuo to afford 970 mg of a crude oil that was purified by silica gel chromatography (95 g, 230–400 mesh). Elution with hexanes:ethyl acetate (3:1) gave 435.8 mg (96.7%) of the N-BOC proline ester 88. The ester 88 exhibited $^1$H and $^{13}$C NMR, IR and MS data in accord with its structure. Anal. Calc'd for $C_{78}H_{153}Si_4O_{13}N$: C, 65.726; H, 10.819; N, 0.983. Found: C, 65.89; H, 11.10; N, 1.00.

The above-described degradation procedure on FK-506 to produce the acetal 86, can be performed on FK-525, FK-523, FK-520, and the propyl derivative of FK-506 (in place of the allyl group) to produce the corresponding acetal analogs of 86, given by the formula BB, below, which can then be reacted with an N-t-Boc secondary amino acid and regenerated to an FK macrolide structure by the process described hereinabove:

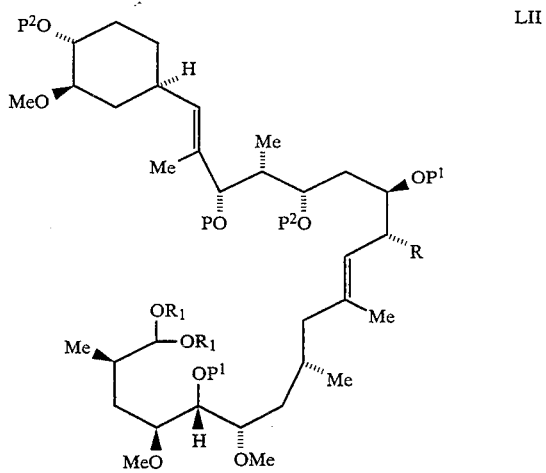

LII wherein P/P$^1$/P$^2$ are independently defined as H or trihydrocarbosilyl, wherein said hydrocarbosilyl groups are independently chosen from C$_1$–C$_4$ linear or branched alkyl, phenyl or benzyl, such that P can be selectively removed in the presence of P$^1$/P$^2$ and R is selected from allyl, propyl, ethyl or methyl, and R$_1$ is methyl or ethyl.

What is claimed is:

1. A process for synthesizing tricarbonyl compounds of structure I, comprising the steps of:

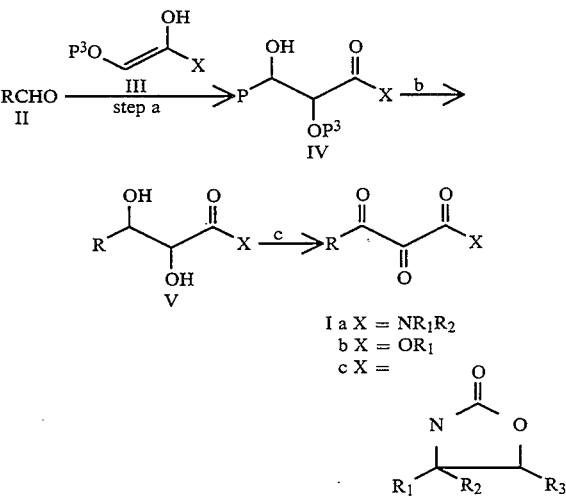

(a) contacting aldehyde II with hydroxyl protected acetate enolate equivalent III under an inert atmosphere in the temperature range of −100° C. to 20° C. in an anhydrous, inert, non-hydroxylic organic solvent for a sufficient time to produce the addition product IV;

(b) deprotecting the 2-hydroxyl function of product IV from step (a) to form V;

(c) treating the hydroxyl-deprotected product V from step (b) in an inert, anhydrous, non-hydroxylic solvent in the presence of both oxalyl chloride and dimethyl sulfoxide under an inert atmosphere at −78° C. to 0° C. followed by triethylamine for a sufficient time to effect formation of the 2,3-diketocarboxylate compound I; wherein: R is substituted or unsubstituted linear or branched $C_1$–$C_{40}$ alkyl, wherein the substituents can be OH, $C_1$–$C_4$ alkoxy, $C_6$–$C_8$ phenoxy, SH, $C_1$–$C_4$ alkylthio, $C_6$–$C_8$ arylthio, $NH_2$, $N(C_1$–$C_4$ alkyl$)_2$, the $C_{11}$–$C_{34}$ carbon framework of FK-506; $P^3$ is linear or branched $C_1$–$C_{10}$ alkyl, $C_6$–$C_{10}$ aryl or benzyl, which can be substituted by halo or $C_1$–$C_4$ alkoxy; trihydrocarbosilyl, wherein said hydrocarbosilyl groups are independently chosen from $C_1$–$C_4$ linear or branched alkyl, phenyl or benzyl; X is $NR_1R_2$, $OR_1$,

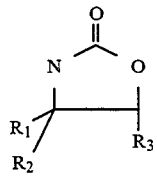

pipecolinic acid or ester, where $R_1/R_2/R_3$ are independently chosen from: $C_1$–$C_4$ linear or branched alkyl, benzyl, phenyl, which may be substituted with halo or $C_1$–$C_4$ alkoxy; and wherein cation M is Li, Na, K, Cs, Ca, Al, Zn, Ti, Sn and B(alkyl)$_2$, wherein the alkyl is $C_1$–$C_4$ linear or branched.

2. The process of claim 1 wherein R is the $C_{11}$–$C_{34}$ carbon framework of FK-506.

3. The process of claim 1 wherein R is

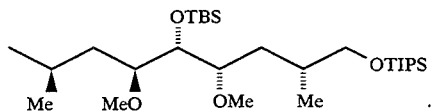

4. The process of claim 1 wherein $P^3$ is benzyl, substituted with $C_1$–$C_4$ alkoxy, or B($C_1$–$C_4$alkyl)$_2$ and X is

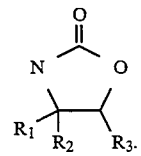

5. The process of claim 4 wherein $P^3$ is p-methoxybenzyl, M is dibutylboron and X is

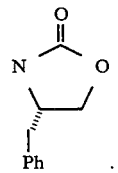

6. The process of claim 1 wherein step (a) said temperature is in the range of −50° C. to 0° C. and said solvent is methylene chloride.

7. The process of claim 1 wherein step (c) said temperature is about −78° C. and said solvent is methylene chloride.

8. The process of claim 1 wherein step (a) further comprises the reaction:

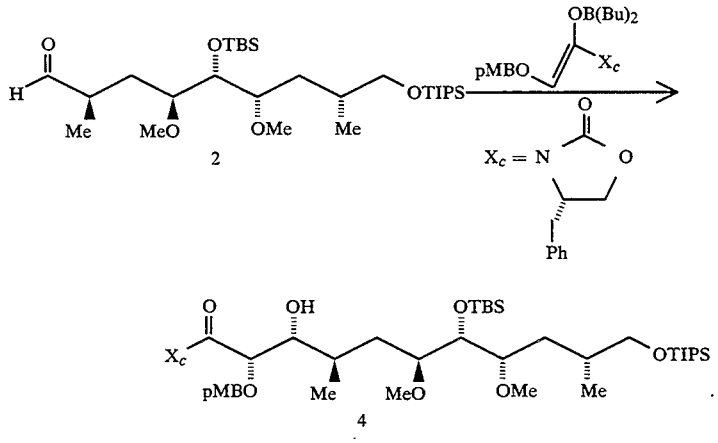

9. The process of claim 1 wherein step (b) further comprises the steps:

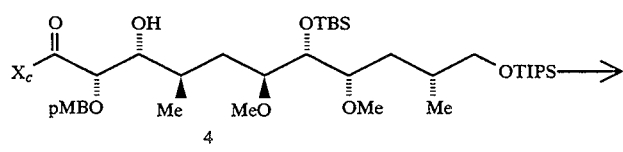

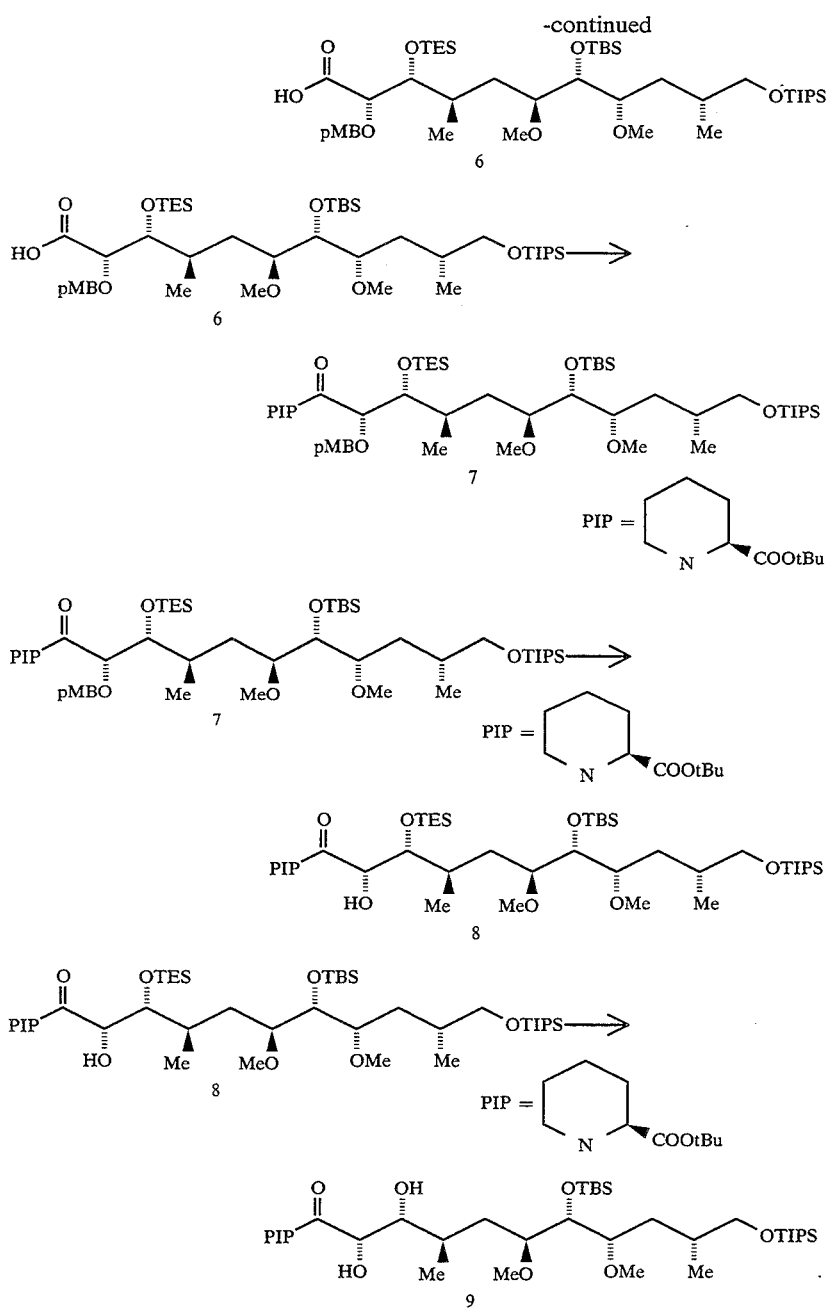
10. The process of claim 1 wherein step (c) further comprises:
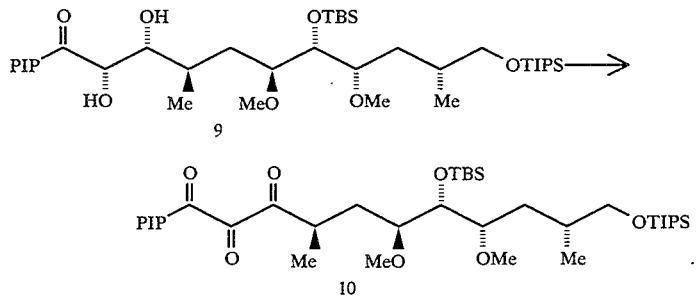
* * * * *